United States Patent
Neal et al.

(10) Patent No.: US 12,329,514 B2
(45) Date of Patent: Jun. 17, 2025

(54) METHODS FOR DYNAMIC POSITION MEASUREMENT OF OCULAR STRUCTURES USING PURKINJE REFLECTION SPOTS

(71) Applicant: Wavefront Dynamics, Inc., Albuquerque, NM (US)

(72) Inventors: Daniel R. Neal, Albuquerque, NM (US); R James Copland, Albuquerque, NM (US)

(73) Assignee: WaveFront Dynamics, Inc., Albuquerque, NM (US)

( * ) Notice: Subject to any disclaimer, the term of this patent is extended or adjusted under 35 U.S.C. 154(b) by 900 days.

(21) Appl. No.: 17/145,335

(22) Filed: Jan. 9, 2021

(65) Prior Publication Data

US 2021/0212601 A1   Jul. 15, 2021

Related U.S. Application Data

(60) Provisional application No. 63/085,391, filed on Sep. 30, 2020, provisional application No. 62/959,127, filed on Jan. 9, 2020.

(51) Int. Cl.
*A61B 3/113* (2006.01)
*A61B 3/02* (2006.01)
(Continued)

(52) U.S. Cl.
CPC ............ *A61B 5/1128* (2013.01); *A61B 3/113* (2013.01); *A61B 3/14* (2013.01); *A61B 5/0059* (2013.01); *A61B 3/102* (2013.01)

(58) Field of Classification Search
CPC ......... A61B 3/107; A61B 3/103; A61B 3/113; A61B 3/14; A61B 3/1225; A61B 3/024;
(Continued)

(56) References Cited

U.S. PATENT DOCUMENTS

| 3,536,383 A | 10/1967 | Cornsweet |
| 4,287,410 A | 9/1981 | Crane |

(Continued)

FOREIGN PATENT DOCUMENTS

| JP | 2005198851 A | * | 7/2005 |
| JP | 2005199851 A | * | 7/2005 |

(Continued)

OTHER PUBLICATIONS

Translation of JP2005198851 (Year: 2005).*
(Continued)

*Primary Examiner* — Dawayne Pinkney
(74) *Attorney, Agent, or Firm* — Quinn IP Law

(57) ABSTRACT

This invention, a Purkinjenator™ optical system, is an eye-tracker and methodology for tracking Purkinje reflection images from a human eye in real-time, which allows for the XYZ position and tip/tilt of structures inside the eye to be determined in real-time. When used in combination with programmable groups of IR LED light sources, unique patterns of Purkinje reflections from internal surfaces (and corneal surfaces) can be identified. Thus, XYZ positioning and tip/tilt of internal structures can be accurately and rapidly determined. An Optical Coherence Tomography (OCT) optical system can be combined with the Purkinjenator™ optical system to provide Z-axis distance information.

24 Claims, 43 Drawing Sheets

(51) Int. Cl.
*A61B 3/10* (2006.01)
*A61B 3/12* (2006.01)
*A61B 3/14* (2006.01)
*A61B 5/00* (2006.01)
*A61B 5/11* (2006.01)

(58) Field of Classification Search
CPC ......... A61B 3/032; A61B 3/18; A61B 3/1015; A61B 3/0025; A61B 3/102; A61B 3/1173; A61F 9/00804; A61F 9/00827; A61F 2009/00848
USPC ................ 351/209, 200, 205–206, 210, 212, 351/221–223, 245–246
See application file for complete search history.

(56) References Cited

U.S. PATENT DOCUMENTS

| | | |
|---|---|---|
| 4,373,787 A | 2/1983 | Crane |
| 4,834,528 A | 5/1989 | Howland |
| 4,836,670 A | 6/1989 | Hutchinson |
| 5,430,505 A | 7/1995 | Katz |
| 7,572,008 B2 | 8/2009 | Elvesjo |
| 7,963,652 B2 | 6/2011 | Vertegaal |
| 8,360,578 B2 | 1/2013 | Nummela |
| 8,678,591 B2 | 3/2014 | Zhou |
| 9,167,965 B2 | 10/2015 | Jaeken |
| 9,301,675 B2 | 4/2016 | Kiderman |
| 9,649,029 B2 | 5/2017 | Blixt |
| 9,918,873 B2 | 3/2018 | Woodley |
| 9,949,636 B2 | 4/2018 | Kersting |
| 9,999,348 B2 | 6/2018 | Gao |
| 10,080,493 B2 | 9/2018 | Reimer |
| 10,188,287 B2 | 1/2019 | Copland |
| 10,251,784 B2 | 4/2019 | Woodley |
| 10,278,576 B2 | 5/2019 | Hwang |
| 10,420,466 B2 | 9/2019 | Cornsweet |
| 10,463,248 B2 | 11/2019 | Cornsweet |
| 10,579,141 B2 | 3/2020 | Aleem |
| 10,606,072 B2 | 3/2020 | Aleem |
| 10,664,049 B2 | 5/2020 | Kim |
| 10,694,938 B2 | 6/2020 | Janunts |
| 10,718,942 B2 | 7/2020 | Egea |
| 10,726,257 B2 | 7/2020 | Ollila |
| 10,813,550 B2 | 10/2020 | Copland |
| 2004/0021826 A1 | 2/2004 | Sarver |
| 2006/0007108 A1* | 1/2006 | Utsumi ................. G09G 3/342 345/102 |
| 2010/0134760 A1* | 6/2010 | Salvati ..................... A61F 2/16 351/246 |
| 2011/0273669 A1* | 11/2011 | Abitbol ................ A61B 3/1015 351/212 |
| 2012/0172854 A1* | 7/2012 | Raymond ................ A61F 9/008 606/5 |
| 2015/0150448 A1* | 6/2015 | Takii ....................... A61B 3/152 351/208 |
| 2016/0074125 A1 | 3/2016 | Raymond |
| 2017/0095147 A1 | 4/2017 | Copland |
| 2017/0112376 A1* | 4/2017 | Gill ......................... H04N 23/23 |
| 2018/0003981 A1 | 1/2018 | Urey |
| 2018/0129041 A1 | 5/2018 | Aleem |
| 2018/0129279 A1 | 5/2018 | Melman |
| 2018/0207031 A1 | 7/2018 | Woodley |
| 2018/0249906 A1 | 9/2018 | Gramatikov |
| 2018/0344157 A1 | 12/2018 | Ng |
| 2019/0156100 A1 | 5/2019 | Rougeaux |
| 2019/0204913 A1 | 7/2019 | Sarkar |
| 2019/0231590 A1 | 8/2019 | Woodley |
| 2019/0235624 A1* | 8/2019 | Goldberg ........... G02B 27/0179 |
| 2020/0154996 A1 | 5/2020 | Blixt |
| 2020/0335032 A1 | 10/2020 | Kiik |

FOREIGN PATENT DOCUMENTS

| | | |
|---|---|---|
| WO | WO2004084719 | 7/2004 |
| WO | WO2012130818 A1 | 4/2012 |

OTHER PUBLICATIONS

H.D. Crane & C.M. Steele, "Generation-V Dual-Purkinje-Image Eyetracker", Applied Optics, vol. 24, No. 4, pp. 527-537, Feb. 1985.
H. Duebel, B. Bridgeman, "Fourth Purkinje Image Signals Reveal Eye-Lens Deviations and Retinal image Distortions During Saccades", Vision Res., vol. 35, No. 4, pp. 529-538, 1995.
M. Almeida, "Detection of Purkinje Images for Automatic Positioning of Fixation Target and Interferometric Measurements of Anterior Eye Chamber", Master Dissertation, University Nova de Lisboa, Spain, Apr. 2012.
P. Santos, et al., "System based on the contrast of Purkinje images to measure corneal and lens scattering", Biomedical Optics Express, vol. 9, No. 10, Oct. 2018, pp. 4907-4918.
"Cassini Ambient"—product brochure, multi-color (700 LED's) Total Corneal Astigmatism LED topography based on 2nd Purkinje raytracing technology, Oct., 2020.
M.R. Clark, "A two-dimensional Purkinje eye tracker using the first and fourth Purkinje images", Behavior Research Methods & Instrumentation, vol. 7 (2), pp. 215-219, 1975.
D.H. Chang, "Centering IOLs Using Purkinje Images", Cataract & Refractive Surgery Today, pp. 35-38, Jun. 2011.
Unknown author, "Technical Challenges in Eye Tracking", pp. 1-43, ESSEM, 2014.
E. Abdulin, et al.,"Custom Video-Oculography Device and its Application to Fourth Purkinje Image Detection during Saccades", 2018.
J. Tabernero, P. Artal, "Lens Oscillations in the Human Eye: Implications for Post-Saccadic Suppression of Vision", PLOS ONE, vol. 9, Issue 4, e95764, Apr. 2014.
S. Manzanera, et al., "Location of Achromatizing Pupil Position and First Purkinje Reflection in a Normal Population", Investigative Ophthalmology & Visual Science, vol. 56, pp. 962-966, Feb. 2015.
T.N. Cornsweet & H.D. Crane, "Accurate two-dimensional eye tracker using first and fourth Purkinje images", Journal of the Optical Society of America, vol. 63, No. 8, pp. 921-928, Aug. 1973.
P. Santos, et al., "System based on the contrast of Purkinje images to measure corneal and lens scattering", Biomed Opt. Express, vol. 9(10), pp. 4907-4918, Oct. 2018.
J. Tabernero, et al., "Instrument for measuring the misalignment of ocular surfaces", Optics Express, vol. 14(22), pp. 10945-10956, Oct. 2006.
M. Bueno, et al., "Purkinje imaging system to measure anterior segment scattering in the human eye", Optics Letters, vol. 32(23), pp. 3447-3449, Dec. 2007.
D. W. Hansen, and Q. Ji, "In the Eye of the Beholder: A Survey of Models for Eyes and Gaze", IEEE Transactions on Pattern Analysis and Machine Intelligence, vol. 32(3), pp. 478-500, Mar. 2010.
M. Sun, et al., "Intraocular lens alignment from an en face optical coherence tomography image Purkinje-like method", Optical Engineering, vol. 53(6), pp. 061704-061708, Jun. 2014.
A. Chamberlain, "Dural Purkinje-Image Eyetracker", United States Naval Academy Trident Scholar Report 238, 65 pages, (1996).
H.L. Hall, "Purkinje images for optical assessment of lenticular surfaces", Univ. of Arizona, Ph.D. Dissertation, 2001.
J. Tabernero, et al., "The accommodative ciliary muscle function is preserved in older humans", www.nature.com/scientificreports/, 6:25551 | DOI: 10.1038/srep25551, pp. 1-7, May 2016.
M. Cognolato, et al., "Head-mounted eye gaze tracking devices: An overview of modern devices and advances", Wearable Technologies for Active Living and Rehabilitation, Creative Commons, https://doi.org/10.1177/2055668318773991, Apr. 2018.
E. R. Abdulin & O.V. Komogortsev, "Study of Additional Eye-Related Features for Future Eye-Tracking Techniques", CHI 2017, May 6-11, 2017, pp. 1457-1463, Denver, CO.

(56) References Cited

OTHER PUBLICATIONS

A. Nolan, et al., "Model eye measurement with novel device combining Purkinje reflections and OLCR", Investigative Ophthalmology & Visual Science, vol. 56(7), Jun. 2015.
Duchowski A. (2007) Eye Tracking Techniques. In: Eye Tracking Methodology. Springer, London. https://doi.org/10.1007/978-1-84628-609-4_5.

* cited by examiner

Ref: [22]

Ref: [16]

Ref: [63]

Ref: [27]

Ref: [1]

Ref: [8]

(*PRIOR* ART)

Ref: [14]

*Ref: [10]*

Ref: [14]

(PRIOR ART)   Ref: [14]

*(PRIOR ART)*
*Ref. [20]*

*(PRIOR ART)*
*Ref. [20]*

*(PRIOR ART)*
*Ref. [20]*

*(PRIOR ART)*
*Ref. [20]*

*(PRIOR ART)*
*Ref. [20]*

*(PRIOR ART)*
*Ref. [20]*

Ref. [20]

*Ref: [11]*

(*PRIOR* ART)

Ref: [5]

Ref: [58]

*Ref: [4]*

(*PRIOR* ART)

Ref: [65]

FIG. 28A (PRIOR ART) Ref: [17]

FIG. 28B (PRIOR ART) Ref: [17]

FIG. 28C (PRIOR ART) Ref: [17]

METHODS FOR DYNAMIC POSITION MEASUREMENT OF OCULAR STRUCTURES USING PURKINJE REFLECTION SPOTS

CROSS-REFERENCES TO RELATED APPLICATIONS

This application claims a priority benefit of U.S. Provisional 62/959,127 filed Jan. 9, 2020; and U.S. Provisional 63/085,391 filed Sep. 30, 2020, both of which are incorporated herein by reference in their entirety.

FIELD OF THE INVENTION

The general field of the invention includes ophthalmology and optometry; and, in particular devices and methods (i.e., eye-trackers) that dynamically tracks the motion and gaze of a human eye in real-time during an ophthalmologic procedure. For example, an eye-tracker can be combined with laser keratotomy (e.g., "LASIK") to improve the placement accuracy and ultimate vision of patients with intraocular optical lens (IOL's) implanted in the eye after removal of the natural crystalline lens (e.g., due to a cataract). Also, new techniques have been developed that modify the refractive/diffractive material properties of an IOL (intraocular lens) or ICL (implantable contact lens) in vivo by changing the index of refraction by applying a focused, pulsed, small-spot scanning laser beam (e.g., femtosecond laser). The beam must be precisely positioned and controlled, which requires real-time measurement to direct and monitor beam delivery. The process of writing a desired optical pattern with a laser on an IOL typically takes tens of seconds. During that time, the IOL may move inside the eye, even if the eyeball itself has been applanated (fixed in place) by external means. A method is needed to track the XYZ position and tip/tilt of the IOL in the eye during such a procedure.

BACKGROUND OF THE INVENTION

There are a number of treatments of an eye that require precise knowledge of the position and arrangement of its internal structures. These include implantation of interocular lenses (IOL) as part of cataract surgery, but may also include ICLs (implanted contact lens, or phakic intraocular lenses), refractive surgery, or even contact lenses. New techniques provide a way to modify the refractive/diffractive characteristics of various optical materials by changing the index of refraction with a femtosecond laser. In nearly all these cases, the treatment in the eye must be precisely positioned and controlled, using dynamic (real-time) position measurement to determine the appropriate place for the laser treatment and to monitor the delivery in real-time.

A number of optical techniques have been developed to measure internal structures in the eye, including: wavefront aberrometry, corneal topography, ultrasound, and OCT (optical coherence tomography). However, these techniques are usually aimed at a more general diagnosis of the eye, and generally lack the combination of accuracy, dynamic range, and speed to actively control surgical procedures in real-time.

Some eye-trackers make use of "phakometry", which is the study of the natural crystalline lens in an eye. In some types of phakometry, OCT is used. OCT consists of performing laser interferometry measurements using a Hartmann-Shack (HS) wavefront sensor to measure the physical dimensions and positioning of a natural lens (or an implanted IOL lens, for example) from signals generated by the HS sensor (i.e., in-situ calibration). See references [3, 17, 23, 35, 36, 39, 43, 54, 60, 61]. OCT can be used to measure: (1) the positional tip and tilt of a lens (natural or IOL); (2) decentration offsets in the X- or Y-direction from the center of the eyeball's optical axis; (3) axial misalignments along the length of the optical axis in the Z-direction, or (4) all of these misalignments.

An OCT system gives a fairly direct measurement of the internal structures of the eye and has been employed to determine the 3D position of IOLs [65]. The overall accuracy is generally limited to 5-7 um, and it involves a complicated system with an X-Y scanner, ray-tracing through the cornea, calibration, and other optical elements. Another difficulty is that the optical materials used in IOLs are low-scatter, so that the OCT signal is weak. This requires slower scan rates to obtain good signal-to-noise ratios (needed to achieve accurate position measurement). There are many trade-offs in the design of OCT systems, such as: wavelength, system type (spectral domain, swept-source, time domain), scanning speed, depth range, axial and lateral resolution, detector efficiency, and source power.

Data processing is an issue for real-time OCT. Processing the cross-sectional images to determine the location of each surface is time-consuming. From the update speed, the required scan times can be calculated. It may be possible to reduce the data size and scan time by only scanning cross-sections in X and/or Y directions. Highly-efficient processing algorithms can be used for position-finding in real-time.

An OCT system can also be combined with a dedicated optical system that detects and monitors "Purkinje" reflections from the eyeball [3, 25]. In another system, the OCT interferometry arm of the instrument can comprise an Optical Low Coherence Reflectometry (OCLR) system [25]. Other systems that have been used include: (1) a time domain optical coherence tomography system; (2) a spectral domain optical coherence tomography system; (3) a Scheimpflug tomography system; (4) a confocal tomography system; (5) a low coherence reflectometry system; and (6) a corneal topography system combined with an OCT system [60]. Note: Purkinje reflections will be discussed in detail later on.

A wide-variety of methods and devices have been used to track movements of the eye, including (but not limited to): (1) IR Limbal Reflections; (2) Yarbus camera-based systems; (3) Chantus tracking systems; (4) Electro-Oculography (EOG); (5) electromagnetic methods; (6) contact lens techniques; (7) scleral contact lens with an attached electromagnetic search coil; (8) limbus/iris-sclera boundary video-imaging systems; (9) Photo-Oculography (POG) systems, and (10) Video-Oculography (VOG) systems with motion-capture [8, 16, 21, 22]. Eye-tracking devices can be built into "heads-up" displays (HUDs) [8, 22, 37, 47, 48, 49], or they can be miniaturized even further and built into eyeglasses (spectacles) [8, 41, 44, 51, 52]. Eye-trackers that track the 2-D gaze point where the eye is looking at a specific location on a computer display screen (e.g., LCD) are also popular [4, 8, 9, 33, 37, 53].

Eye-tracking instruments can be made as compact, desktop devices [5, 8, 46, 56]. They can be operated in a bright-pupil detection mode [55], or in a dark-pupil mode [38], or in both modes [38, 58].

Refractometers (optometers) have been developed that use similar Purkinje imaging techniques as eye-trackers [26, 42, 47, 48, 49]. Multiple-color LEDs (including IR wavelengths) can be used to illuminate the eyeball, which provides certain advantages over single-color LEDs, or tungsten or xenon lamps can be used [5, 47, 48, 49]. An "infrared retinoscope" has been developed that uses a ring of LED lights to illuminate the eye at different angles and monitors the subsequent reflections of light reflecting off of the retina [29]. A similar retinal "Retro-Reflector" instrument has been developed [38, 55, 58]. The use of infrared light to illuminate the eye also provides more light output from the eye because the retina reflects a much higher proportion of infrared light than it does of visible light incident thereon [26]. A "behind-the-eye" monitoring device has also been described, which detects light reflected off the inner surfaces of eyeglass lens [44]. Some eye-trackers include a telecentric optical element in the main optical path to provide greater depth of field [4, 10, 11, 13, 14, 20, 56] along the optical axis (Z-direction).

An eye-tracking instrument has been developed that uses an optical waveguide for illuminating the eyeball with light from at least two different directions [31, 34]. The waveguide can comprise a free-form, folded prism optical element that is used for illuminating the eyeball [41]. In another device, a spatial light modulator (SLM) is used to control the intensity of light in the main optical path, and a pico-projector (micro-CCD display) is used to provide a rapidly-adjustable 'fixation' target for the patient to look at during the procedure (rather than looking at a few LED point-sources as the fixation target) [11, 34, 52]. A related technique called "LED topography" has been used [5].

An "ocular fundus" camera system has been described the visualizes the interior of the eyeball during ophthalmologic procedures [45]. An IR "gaze monitor" has been described that tracks a moving eyeball using IR light [59]. A "Dynamic Purkinje-Meter" has been described in [11, 50, 56]. In another reference, a "3-D Purkinje Meter" is used as an eye-tracker [28]. Specialized "Scheimpflug" camera techniques have also been used for eye-tracking [56, 62].

These optical instruments typically use a single-pass through their optical system (optical path) [62]. Many of these optical instruments use a full-ring or semi-circle ring (e.g., U-shape) of LED light sources to illuminate the eyeball [10, 14, 20, 29, 32, 50, 60]. The ring can be a semi-circle of LED illumination sources that are constantly "On" during the data collection step [10, 14, 20]. Alternatively, the illumination light source(s) can be alternatively flashed On and Off [29, 45].

Infrared light (IR) LEDs can be used so as to not bother the patient with bright lights from ordinary visible LEDs or other bright visible sources (e.g., tungsten or xenon lamps) [6, 9, 13, 14, 17, 20, 26, 29, 30, 33]. Another system uses a "Placido Disk" (e.g., as used in a Keratoscope) to project a series of concentric rings of alternating light and dark circles onto the eyeball [60]. Alternatively, a matrix of LED or LCD lights can be activated in a time-sequenced fashion (i.e., sequentially activated over time), and the reflections from the eye captured with a high-speed, time-synchronized digital CCD camera [60].

"Video-Oculography" (VOG) is a methodology that tracks an eyeball in real-time using "Purkinje" reflections from reflective surfaces of the eyeball (also called "purkinjemetry" [9, 24]). In VOG, an image of the eye from a television or CCD camera is processed by a computer to determine the horizontal and vertical positions of the pupil within the image, and these linear positions are subsequently converted to an angular orientation of the optical axis using geometrical relationships.

Purkinje images are reflections of objects from the structure of the eye. They are also known as "Purkinje reflexes" or "Purkinje-Sanson images". Purkinje—Sanson images are named after the Czech anatomist Jan Evangelista Purkyne (1787-1869) and after French physician Louis Joseph Sanson (1790-1841).

Studies of eye movement have been made since the mid-1800's. For example, the Frenchman Louis Emile Javal observed in 1879 that the process of reading does not comprise a continuous sweeping of words at a uniform speed across a page, but, rather, it consists of an alternating series of stationary "fixations" that last for a few hundreds of milliseconds, followed by multiple, quick "saccades" (rapid rotation of both eyeballs in-between the stationary fixations) that last 30-50 milliseconds. For example, a sudden 10° rotation of an eyeball has a peak angular velocity of 300 degrees/second (one of the fastest reflexes in the body). During a saccadic episode, it is believed that a person's vision is suppressed (possibly to reduce deleterious effects of blurring during the saccade).

Accurate tracking of the eyeball's gaze using an eye-tracker device is complicated by these naturally-occurring saccadic motions happening in-between periods of fixation. Properly accounting for them generally improves the accuracy of ophthalmologic procedures. Current generations of eye-trackers generally have sufficiently fast temporal response and spatial accuracy to track oscillations of the lens (natural or IOL) during "micro-saccades", where the eye makes (on-average) about three saccadic movements per second [46].

At least four Purkinje images are typically visible (although some images may require image intensification to be seen). The first Purkinje image, $P_1$, is a reflection from the outer surface of the cornea. The $P_1$ corneal reflection is a virtual source generally known as "glint" because it has the greatest intensity of the four reflections. Purkinje reflections from IOLs are also strong because of the large difference of index of refraction between the eye vitreous and aqueous humours and the IOL's polymeric material. The strong reflection signal (reflex) makes Purkinje imaging suitable for high-speed tracking of IOL positioning.

The second Purkinje image, $P_2$, is a reflection from the inner surface of the cornea. It is significantly less intense than $P_1$, and can significantly overlap $P_1$ images. The third Purkinje image, $P_3$, is a reflection from the outer (anterior) surface of the lens (natural or IOL). Finally, the fourth Purkinje image, $P_4$, is the reflection from the inner (posterior) surface of the lens (natural or IOL). Unlike the first three reflections, which are upright images, $P_4$ is an inverted image. $P_1$ and $P_2$ images have similar size and are usually overlapped due to the small corneal thickness. $P_3$ images have the largest size (approximately twice that of $P_1$); and $P_4$ images are usually slightly smaller in size than $P_1$ [14].

Some examples of these four reflection paths are shown in FIGS. 1, 2, and 3 [16, 22]. An excellent overview about Purkinje images is provided by Chang [7]. When measuring or monitoring implanted IOLs, the locations of Purkinje images are linear combinations of IOL tilt, IOL decentration, and eye rotation [17]. In other words, the relative positions of the $P_1$, $P_3$, and $P_4$ images, with respect to the pupil center, are proportional to the eye rotation, IOL tilt, and IOL decentration [17]. As the eye rotates, the first Purkinje ($P_1$) image moves in the same direction as the eye's motion, while the fourth image ($P_4$, from the concave surface of the back of the lens), moves in the direction opposite the eye's motion (relative to the optical axis). Thus, coincident movement of both $P_1$ and $P_4$ images indicates head motion (translation), while the difference between the $P_1$ and $P_4$ image motions indicates eye rotation within a non-moving (fixed) head [2, 14].

Note that the third and fourth Purkinje images ($P_3$ and $P_4$) can be visible from within the eye itself. Light reflected away from the surfaces of the lens can in turn reflect back into the eye from the rear surface of the cornea. Note also that light from the second, third, and fourth Purkinje images ($P_2$, $P_3$, $P_4$) is approximately 100 times less intense than that from a first Purkinje image ($P_1$), which makes it more difficult to easily identify these weaker images $P_2$, $P_3$, and $P_4$ [19]. The least intense Purkinje image is the second image, $P_2$, which is the most difficult to see clinically [7]. $P_3$ is larger than the other images, while $P_4$ is smaller but with a brighter intensity than $P_3$. The differences in sizes are because the curve of the lens is larger on the front (anterior side) of the lens versus the back (posterior side) of the lens (see FIG. 2).

For reference, the eye's anatomy is shown in FIGS. 4 and 5.

Most prior art eye-trackers use the first and fourth Purkinje images ($P_1$ and $P_4$). Dual-Purkinje trackers (e.g., DPI, "$P_1$-$P_4$ trackers"), first developed in the early 1970's by Crane, Cornsweet, & Steele, measure the difference in relative motion between the $P_1$ and $P_4$ images (which are usually "spots", or collection of spots, when the light sources are spot LEDs or other point sources of light) on the eyeball when the eye rotates a pre-determined amount (as guided by a "fixation" target) in its socket [1, 2, 6, 7, 9, 10, 12, 14, 16, 17, 18, 20, 26, 27, 28, 29, 33, 34].

FIGS. 6 and 7 show two prior art optical systems that make-up a Dual-Purkinje (DPI) eye-tracker by Crane and Steele [1, 27]. It is a very complex optical system, with approximately 35 optical elements. Dual-Purkinje trackers can have as many as 2-4 individual pairs of electro-mechanical servo-motors that adjust the angles of 2-4 mirrors so that the two different Purkinje images ($P_1$ and $P_4$) are superimposed on top of one another in essentially real-time. The amount of angular movement that the mirrors have to rotate to cause superposition of the two Purkinje images is then used to calculate the gaze angle(s) [8]. Another example of a DPI system is shown in FIG. 8. The patient is biting on a bite-bar in order to hold her head in a stable, stationary position while being monitored.

FIGS. 9A and 9B compare two "dark-pupil" photographs of an eyeball taken with a DPI system, including both $P_1$ and $P_4$ Purkinje reflections, where the pupil shown in FIG. 9A is much larger than the pupil shown in FIG. 9B. A full, circular ring of LED lights was used to illuminate the eye, with the ring being centered on the optical axis. The separation distance, s, between $P_1$ and $P_4$ is significantly larger with the larger pupil diameter (FIG. 9A), than the separation distance, s, for the smaller diameter pupil (FIG. 9B). Note that the location of $P_1$ is relatively fixed, while $P_4$ moves closer to $P_1$ in response to changes in the eye's properties (e.g., pupil size, rotation angle, etc.).

Dual-Purkinje eye-trackers, such as those shown in FIGS. 6, 7, and 8, have: (1) very high spatial and temporal resolution; (2) are very accurate for X and Y directions; and (3) can accurately detect micro-saccades in essentially real-time [8]. Disadvantages include: (1) DPI trackers can be very "fiddly" to operate; (2) the head must be restrained with a bite-bar; (3) the device is very expensive; (4) the device is basically made by only one company; and (5) gaze signals contain post-saccadic oscillations [8]. DPI trackers have largely been replaced by video-based techniques (e.g., VOG).

FIGS. 10, 11, and 12 show a more recent, improved Purkinje-based eye-tracker system by Tabernero, et al. called a "Dynamic Purkinje-Meter (DPM)" [10, 14, 20]. The DPM device consists of a high-speed, high-resolution, IR-sensitive CCD camera (278 frames/sec) and a semi-circular ("U"-shaped) ring of white or IR LED illumination lights arranged uniformly around the optical axis of the camera. The eye is focused on one of two fixation targets ("stimuli"), which are placed off to a side (i.e., off-axis). Each fixation target is separated apart by a 9° arc. The fixation target can also comprise a square matrix (grid) of nine red (visible) LED lights mounted on a flat board (see FIG. 11). $P_1$ and $P_4$ Purkinje reflections from the U-shaped pattern of IR LED lights from the eye reflect off a dichroic (beamsplitter) mirror (M1) when the mirror is oriented in position "A" and enter the high-speed IR CCD camera, where the deflected/distorted U-shaped images ($P_1$ and $P_4$) are recorded by the camera. Saccadic movements of the eye are generated in response to alternatively flashing the red LED lights on the fixation target from a central position to a peripheral position at a rate of 0.5 to 1 Hz. The IR camera is optically conjugated with the iris plane of the eye. The dichroic mirrors have the property of reflecting IR light to the Hartmann-Shak (HS) sensor or to the CCD camera (depending on its position "A" or "B"), while visible light is transmitted through the mirror to the eye. The method of measuring IOL wobbling (after a saccade) is based on recording the oscillations of Purkinje images after the subject performs a forced saccadic eye movement. Alternatively, in place of using nine flashing red LED lights for the fixation target, the stimuli (e.g., a pair of Left/Right Maltese Crosses drawn on a board) can be retro-illuminated by white LED's that alternatively flicker ON/OFF with a frequency of 0.5 to 1 Hz (see FIG. 10).

FIGS. 10, 11, and 12 show a second optical pathway mounted on the same optical bench. The same fixation stimuli can be used to measure the subject's refraction (or aberrations) when the first dichroic beamsplitter mirror M1 is moved to position "B". In this case, IR light from a 1050 nm IR source is directed towards the retina of the eye, which reflects off of the retina and is directed back towards to a Hartmann-Shack (HS) wavefront sensor via a second dichroic beamsplitter mirror, M2, and a telecentric element (teleobjective). The pupil and the plane of the microlenses of the HS sensor are optically conjugated with a telecentric teleobjective (i.e., telescope), as shown in FIG. 12. The HS sensor performs ocular wavefront measurements of the eye's surfaces (aberrometry). Also, the pupil can be directly monitored in real-time with a second, "pupil monitoring" camera, using the second optical pathway and a Long-Pass Dichroic Mirror (LP-DM), M3, acting as a beamsplitter.

FIGS. 13A and 13B show an example of three different Purkinje reflections from a subject's eye, as measured by a Dynamic Purkinje-meter (DPM) [14]. As expected, $P_1$ is the brightest image, and is upright. $P_2$ is obscured by $P_1$. $P_3$ is the largest image, and is upright. $P_4$ is the smallest image, and is inverted.

FIGS. 14A, 14B, and 14C show examples of computer simulations of $P_1$ and $P_4$ Purkinje reflections from a subject's eye with an implanted IOL lens reacting to various simulated eyeball motions, as modelled by a ray-tracing computer program, Zemax [20]. In FIG. 14A, the IOL is centered about the optical Z-axis of the eye. In FIG. 14B, the IOL has been displaced upwards by 0.5 mm (i.e., vertical decentration). In FIG. 14C, the IOL has been further displaced upwards by 1.0 mm. In steady-state, the Zemax computer simulation shows that the location of the first Purkinje image, $P_1$, stays constant for all three different positions of the misaligned IOL. The location of the fourth Purkinje image, $P_4$, moves to the left (along the X-axis) a distance that is proportional to the amount of misalignment (decentration) of the IOL lens in the Y-direction. Note that the direction of motion of the $P_4$ image (i.e., horizontally along the negative X-axis) is rotated 90° from the direction of motion of the IOL decentration (i.e., vertically along the positive Y-axis), which is a non-intuitive result.

FIG. 16 shows an example of typical oscillations of the eye's lens during, and after, an initial forced saccade, as measured with Tabernero's Dynamic Purkinje-Meter (DPM) [10, 20]. Due to the elastic attachment of the eye lens with stretchy (elastic) ligaments, movement of the lens lags the initial rotation of the eyeball at the beginning of a saccade, and then overshoots at the end of a saccade (which last about 50-100 milliseconds) [2]. After the initiating the saccade motion at time=50 msec, the eye rotates to its new position in about 30 msecs, and then the lens oscillates ("wobbles") as a damped oscillator for about 3-4 cycles of oscillation, which last about 100 msec in total. Tabernero et al. also measured the IOL's position and tilt [14]. However, they were not able to determine an accurate Z-axis position of either the natural lens or IOL, and thus were not able to completely measure all the parameters necessary to control a scanning laser beam in real-time during a surgical procedure.

FIG. 17 shows a different eye-tracking system comprising two, co-aligned light paths, which allows for simultaneous measurement of the $P_1$ image and the Achromatic Point (AcP) of the eye [11]. One optical path captures an image of the real pupil of a subject (optical path), while the other path presents the eye with a visual chromatic test (visual path). The eye is illuminated with a circular array of IR LEDs (850 nm). The pupil plane is optically conjugated with a transmissive Spatial Light Modulator (SLM) for light intensity control. A telescope is formed with lenses L2 and L3, and the CCD camera is equipped with a telecentric teleobjective lens (working distance=11 cm). The corneal Purkinje reflex (reflection) produced by a semicircular array of IR LEDs is recorded by means of a CCD camera with a telecentric objective through a cold mirror (CM). The visual path consists of a pico-projector for generation of a chromatic visual test; a collimating lens (L1), and a cold mirror (CM) to direct the chromatic test toward the eye coaxially to the optical path.

FIG. 18 shows an eye-tracking system called "Cassini Ambient" [5]. This is a compact eye-tracker designed to study astigmatism in a patient's eyes. The Cassini Ambient device: (1) assesses ocular surface stability; (2) measures the posterior cornea; and (3) detects corneal irregularities using "LED topography". Multiple colors are used for the 700 visible illumination LED's, including green, red, and yellow. Point-to-point ray tracing is used to track the $2^{nd}$ Purkinje reflection ($P_2$). The device is useful for planning implantations of toric IOLs. The central corneal measurements are superior to Placido and Scheimpflug methods in cases of high irregularities. The system has seamless connectivity and integration for Femtosecond Laser Assisted Cataract Surgery (FLACS) techniques. Essentially, the system creates a unique algorithm address for each colored spot relative to neighboring spots of different colors (as compared to a design that may use adjacent white lights).

Some eye-tracking devices use other differences between Purkinje images to monitor eye movement, including: ($P_1$-$P_2$) tracking [5]; ($P_1$-$P_3$) tracking [3, 19]; and ($P_3$-$P_4$) tracking [4, 13, 15, 16]. Other "single-glint" eye-trackers track the motion of a single bright spot (reflection) on the eyeball's cornea including: $P_1$ tracking [11, 30, 58]; and $P_4$ tracking [15, 17].

FIG. 19 shows an eye-tracking system based on a single-glint tracking ($P_1$ tracking) [58]. The system can use multiple cameras, placed at different angles to the main optical path, in order to capture both bright-pupils and dark-pupils. Images from the two different pupil modes are compared for quality purposes.

FIG. 20 shows another eye-tracking system based on a single-glint ($P_1$) tracking [4]. The system comprises a xenon lamp illuminator (XL), long-pass filters (F1 and F2), opaque plate [OP] with small slits; telecentric objective lens (TO), electron multiplying CCD camera (EMCCD), and a fixation target (FT). Because the first Purkinje image ($P_1$) is much brighter than the others, it becomes saturated when the dynamic range of the camera is optimized to record the other three (less-intense) Purkinje images ($P_2$, $P_3$, and $P_4$). A number of different artificial eyes were used to help calibrate the tracking device. Some test subjects wore scatter-customized contact lenses to simulate different levels of corneal opacification (e.g., cataracts) [4].

Purkinje reflections from an IOL can create complicated images on a camera. Especially with some categories of PCIOLs, the images may spread out and overlap. The reason is that to enable easy insertion of the IOL (or ICL) into the eye through a small incision, IOLs are made thin and nearly flat so they can be inserted while rolled up. Once in the eye, the surgeon manipulates them to unfold them. The thin and nearly flat construction of the IOLs make it so that the Purkinje reflections are much more spread out than those reflecting from a natural lens. And the reflections are likely to overlap.

FIG. 21 shows a magnified photograph of a normal phakic eye with a natural lens and dilated pupil displaying 1st and 4th Purkinje images ($P_1$ reflecting from the front surface of the cornea, and $P_4$ reflecting from the posterior surface of the lens), taken with a Purkinjenator™ eye tracking device according to the present invention. Purkinje images $P_3$ and $P_4$ from a natural lens are much weaker, and appear underneath the first Purkinje image ($P_1$). Note that $P_4$ is only partially visible (lower right).

FIG. 22 shows a magnified photograph of an eye with a diffractive, multi-focal IOL (MF-IOL) implanted within the eye (photograph taken by a Purkinjenator™ eye-tracker). The large "spot" nearly filling the pupil is the third Purkinje image, $P_3$ (reflection from the front surface of the MF-IOL). $P_1$ images can be seen, as well, in addition to a series of concentric Fresnel Rings from the multi-focal IOL. The large spot of the $P_3$ image obscures the $P_4$ reflections from the backside of the MF-IOL. Note: Purkinje reflections from polymeric IOLs are much brighter than reflections from natural lens due to large differences in the indices of refraction of the different materials.

FIG. 23 shows a magnified photograph of an eye with an implanted, single-focus (monofocal) IOL (with the photograph taken by a Purkinjenator™ device). The LED illumination lights are arranged in a semi-circular U-shape. The front and back surface reflections ($P_3$ and $P_4$) from the monofocal IOL can be readily distinguished as U-shapes. The upright-U $P_3$ image comes from the front surface of the IOL, and the inverted-U $P_4$ image comes from the back surface of the IOL. In this example, the reflections from the different internal and external structures of the eye are fairly well isolated, so determining the pattern using image correlation techniques is straightforward. However, this is not always the case, and accurate results depends on knowing the precise tip/tilt and XYZ position of the IOL.

When the Purkinjenator™ optical device turns on one LED light source at a time, only two dots appear as images on the cornea, and it is not possible to determine which dot came from which reflecting surface from a single light source. However, with multiple light sources, for example, 6 lights sources, the device can capture six images. Software can then analyze them as a set to assign specific spots to the correct IOL reflecting surfaces.

In FIG. 23 the sizes of the U-shaped images are different from each other. That means the magnifications are different. So, if one moves the semi-circular LED illumination ring sideways, the two U-shaped images will move relative to each other. In other words, as the projecting light sources are moved horizontally, the two images move at different rates. So, one means of providing for separation of reflected spots is to move the lights horizontally to a position where the U-shaped images do not overlap. In fact, that is most likely what the instrument operator did to create the configuration shown in FIG. 23.

In a practical instrument, instead of physically moving the light sources horizontally, it is more convenient and flexible to have additional adjacent light sources that are sequentially activated. So, for example, instead of using a single ring of external LEDs, a second or third ring of external LEDs can be used (see the Detailed Description of the Invention).

Copland et al. in U.S. Pat. No. 7,967,440, and Campbell et al. in U.S. Pat. No. 7,976,163, disclose methods for mapping corneal topography using a pattern of light spots, which are incorporated herein by reference. Copland '440 discloses methods for reducing the reflection from the second surface of the cornea in order to measure the first surface accurately, or to suppress the reflection from first surface in order to measure the second surface accurately. However, these instruments are not aimed at measuring the internal structures of the eye, but rather at measuring the corneal surfaces. Campbell '163 disclose the use of a centrally-projected set of light spots from a Helmholtz Source (HHS) that is used to determine the distance between the instrument and the eye. This is only used to provide information about the outer corneal surface. There is no description in either U.S. Pat. No. 7,976,163 or U.S. Pat. No. 7,967,440 of varying the light spots dynamically in space or time, or of dynamically measuring internal structures within the eye.

Korb et al. in U.S. Pat. Nos. 10,413,174; 9,545,197; 8,915,592; 9,642,520; 8,545,017; 8,746,883; and 8,092,023 describe an apparatus for measuring the tear film of the eye using color interferometry. They are faced with the problem of specular reflections from the illumination system. In order to remove these unwanted specular reflections, they switched on/off left/right lighting systems and acquired multiple images. Their purpose was to subtract and eliminate unwanted reflections. However, in the present invention, these specular reflections from the eye, and/or reflections from internal structures or elements inside the eye, are used to measure and monitor the optical element's position and angle.

Against this background, the present invention was developed.

SUMMARY

This invention, a Purkinjenator™ optical device, is an eye-tracker and associated methodology for tracking Purkinje images on human eyes in real-time, which allows for the XYZ positions and tip/tilt angles of structures inside the eye to be determined in real-time. When used in combination with programmable groups of LED light sources, unique patterns of Purkinje reflections from internal surfaces (and corneal surfaces) can be identified by synchronizing the projected light with an IR CCD camera. Thus, XYZ positioning and tip/tilt of internal structures can be accurately and rapidly determined. An Optical Coherence Tomography (OCT) optical system can also be combined with a Purkinjenator™ optical system to provide accurate and rapidly-determined Z-axis distance information.

Some novel aspects of a Purkinjenator™ optical system methodology include, among other things: (1) synchronizing the LED illumination with a CCD camera so that only one LED (or only one selected set of LEDs) is imaged at a time; and (2) projecting a pattern of light through a lens to compute Z-axis positioning of an internal element inside the eye (such as an IOL).

In principle, it would be sufficient to only use Purkinje-based image analysis to monitor the Z-axis position of an IOL. However, such a data analysis is rather involved, and it might be difficult to do the analysis of the Z-location sufficiently fast for practical use in a real-time system. As an alternative option, the system can combine performing an Optical Coherence Tomography (OCT) analysis, alternated with doing Purkinje-based motion-capture analysis. The OCT analysis easily and rapidly gives Z-distance in real-time during the entire data capture sequence, while the Purkinje image analysis easily gives the XY positioning (decentration) and tip/tilt values (also in real-time).

DETAILED DESCRIPTION OF THE INVENTION

Figure 24:
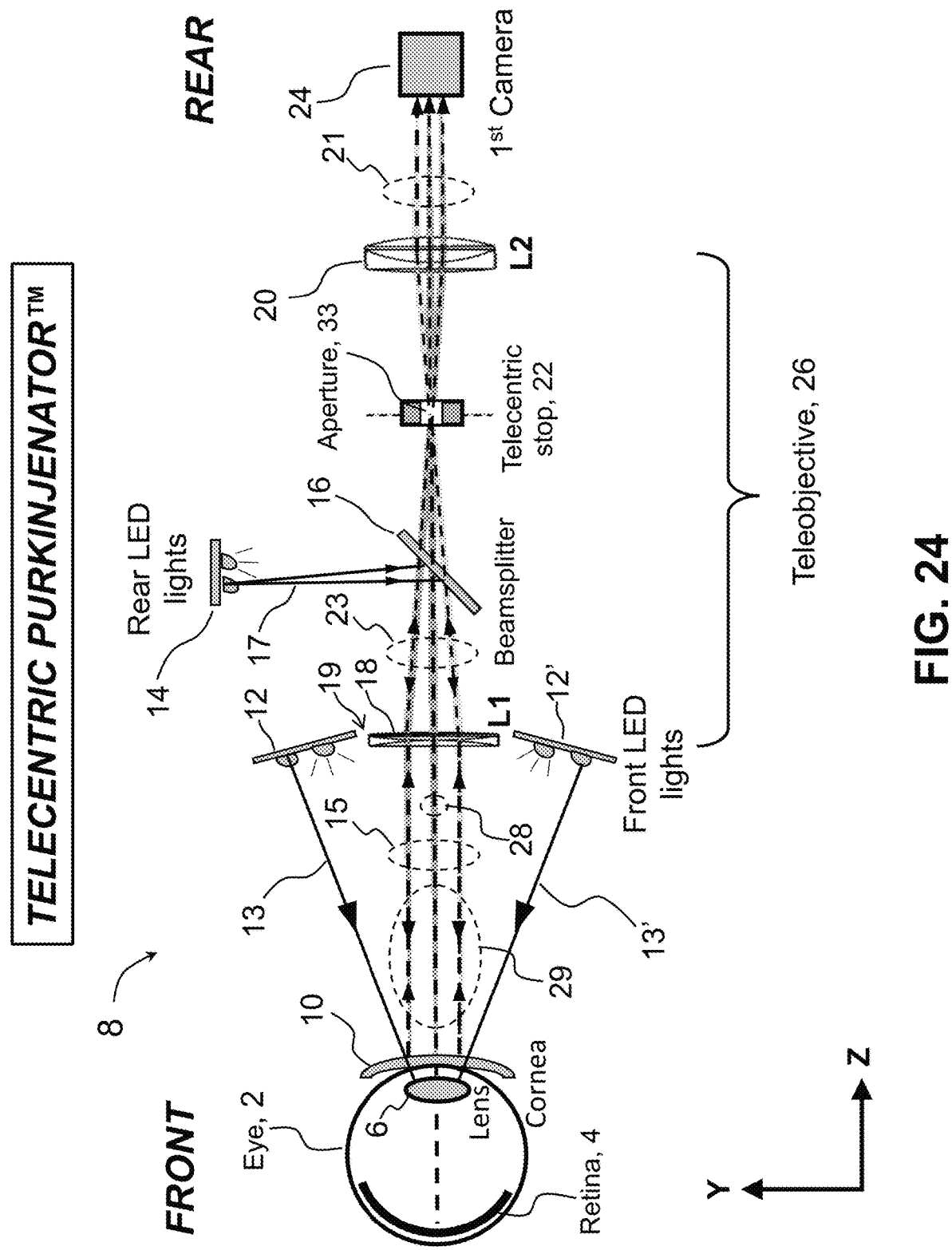
FIG. 24 shows a first embodiment of a schematic optical layout of a Purkinjenator™ eye-tracking device, according to the present invention.

FIG. 24 shows a schematic layout of a first embodiment of an optical system 8 of a Purkinjenator™ optical device, according to the present invention. Optical system 8 comprises means and a methodology for dynamically controlling the illumination in real-time during the light acquisition process, and for separating any overlapping Purkinje images, even in the presence of complicating reflections. The Purkinjenator™ optical system comprises a telecentric image relay element 24, similar to the "Dynamic Purkinje-Meter" instrument used by Tabernero and Artal [10, 14, 20]. However, there are additional elements in the present invention that are different than the system taught by Tabernero, et al. Note: the words "optical device", "optical instrument", "optical system", and "optical set-up" are interchangeable and mean the same thing. Also, the phrases "eye-tracking" and "gaze tracking" are interchangeable and mean the same thing. The word "IOL positioning", as it refers to in-vivo movement of an implanted IOL, generally includes both position misalignments along the X, Y, or Z-axes, and/or any excess tip/tilt of the IOL.

In FIG. 24, the Purkinjenator™ optical system 8 comprises a first (front) set of LED light sources 12, 12', that are arranged in a first pattern or configuration around the objective lens 18 (L1). The LED lights can be controlled so that they may be individually programmed, or programmed in groups or patterns. The first (front) set of LED lights 12, 12' can be arranged as a semi-circular ring (which forms "U"-shaped Purkinje images on the cornea). In another embodiment, front LED lights 12, 12' may be arranged on the surface of a support cone (not shown). The LED lights 12, 12' can be visible or infrared (IR) LEDs (preferably IR LEDs). The front set of illumination LED's 12, 12' is controlled with a micro-controller (not shown) and firmware, which may be synchronized to a high-speed, global shutter camera 24. This can allow the individual Purkinje reflections to be identified and separated from each other (if overlapping), thus enabling a rapid analysis that will identify the IOL's XY position and tip/tilt angles.

Continuing with FIG. 24, light rays 13, 13' emitted by the front set of LEDs 12, 12' pass through the cornea 10 and into the lens 6 of the subject's eye. Then, Purkinje images ($P_1$, $P_2$) are reflected from the cornea 10, and ($P_3$, $P_4$) images are reflected from the lens 6, to form a bundle of light rays 15 that pass through the front lens 18 (L1) of telecentric teleobjective 26. The light rays 15 continue along the optical path 28 through dichroic beamsplitter 16, and then focus at the telecentric stop 22. Finally, light rays 15 continue through the rear lens 20 (L2) and into high-speed CCD camera 24, where the Purkinje images are captured in essentially real-time.

The present inventive optical system 8 has many novel features not found in Tabernero's DPM instrument, or any other known prior art. As shown in FIG. 24, a second (rear) set of LED light sources 14 is disposed relatively close to the optical axis 28, which projects light 17 onto beamsplitter/dichroic mirror 16 and then onto the central portion of the eye by passing through the front objective lens 18 (L1). Note that beamsplitter 16 is disposed in-between the front objective lens 18 (L1) and the rear lens set 20 (L2). Lenses 18 and 20 are typically simple, achromatic doublets, although slightly more complicated triplets or four-element lenses can be used if higher image quality is desired. The rear set of LEDs 14 (which can be visible LEDs, or IR LEDS emitting IR light at 800 nm) can be arranged as a ring, a semi-circular ring, a regular XY grid, or periodic array or matrix of LEDs. Likewise, camera 24 can be a high-speed (e.g., 121 or 278 fps) IR CCD camera operating at, for example, 800 nm. Light 17 emitted from rear LEDs 14 reflects off of beamsplitter 16, and then illuminates the eye 2. The light then reflects off cornea 10 and internal structures of the eye, including lens 6 and the retina 4, thereby forming multiple Purkinje-type images. Then, light reflected from the cornea 10 and internal structures of the eye (e.g., lens 6 and retina 2) then takes a double-pass 29 through optical system 8 as it travels along optical path 28 back through teleobjective 26 and into CCD camera 24. This is different than Tabernero's DPM device (see, e.g. FIG. 10), which uses only a single-pass optical path from the front set of IR LEDs back to the IR CCD camera 24. The use of non-visible IR light for illuminating the eye is desirable because it prevents the subject from being bothered or disturbed by bright visible lights while making critical measurements. The rear LEDs 14 be arranged in a semi-circular or circular ring, but a preferred pattern is an XY grid.

Figure 25:
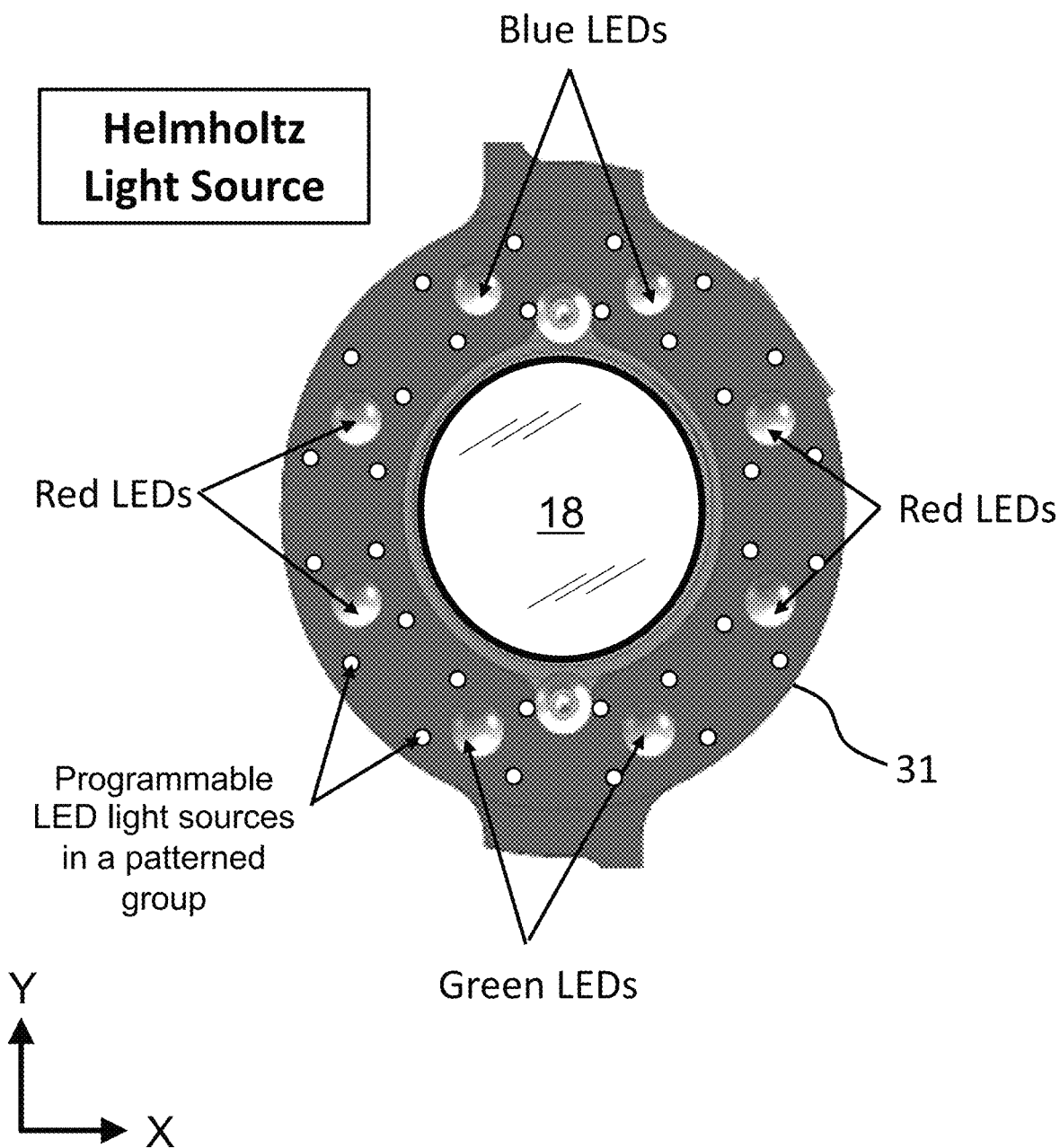
FIG. 25 shows a front elevation view of an example of a Helmholtz light source (HHS) with programmable LED light sources arranged in a multiple patterns or groups, according to the present invention.

The rear set of LEDs 14 can also be configured as a Helmholtz light source (HHS) 31, an example of which is shown in FIG. 25. Helmholtz light source 30 can comprise an annular plate 30 centered on the optical axis 28 (not shown), which closely surrounds the front objective lens 18 (L1), and contains a variety of multi-colored LEDs, including green, red, and blue LEDs. Helmholtz light source 31 can also include a matrix of individually-addressable (programmable) LED light sources arranged in a patterned set, according to the present invention.

Optionally, with respect to FIG. 24, an aperture 33 can be located at the intermediate focus position (telecentric stop 22) to restrict the amount of light 15 that is transmitted to camera 24 to be light that is collimated in the object space. The aperture diameter can be fixed or adjustable. A typical stop size is between 1 and 5 mm in diameter, with the smaller size having an advantage of giving the system a longer depth of focus. A disadvantage of an aperture less than 1 mm diameter is the need for using very bright LEDs. Another advantage of the stop is it restricts the numerical aperture of the light bundles from the LED that make it onto the camera. Some inventors mention that LEDs that emit light in a narrow angle and pointed at the eye are advantageous for producing clean Purkinje images. Creating and aiming such LEDs is a difficult task, and it creates the need to place the eye at a location where the multiple light beams from the LEDs cross. A simpler approach is to use conventional LEDs that emit light into a broad range of angles and then to use the aperture at telecentric stop 22 to only pass desirable light rays from the eye 2 to the camera 24.

As the eye (or optical element within the eye, such as an IOL) moves along the optical axis 28 in the Z-direction, the single-pass vs. double-pass reflected Purkinje images move differently from each other. The double-pass images (generated by the rear LEDs 14) only respond to the curvature of the reflecting surface and not to the path's distance.

The light from the single-pass portion, by contrast, responds to both Z-axis motion of the optical element and to changes in curvature. Thus, by comparing between the two regions (single-pass and double-pass), the absolute Z-axis distance from the eye to the first lens 18 (L1), and the curvature of the internal structure (IOL) or cornea, can be completely determined.

For assumed simple spherically-curved surfaces, the well-known thin-lens equation can be written to solve for the exterior cornea surface shapes, distance of the cornea from the front lens 18 (L1), and the internal lens front and back curvatures, lens thickness and distance of the lens from the back of the cornea. A thin-lens equation is written for each combination of light source and surface of the eye and then solution is calculated by the method of simultaneous equations. For more complicated shapes, such as ellipses or aspheres, with decentrations or tilts, optical raytracing can provide more accurate results.

Using this concept in the Purkinenator™ allows for XY and Z position to be determined. When used in combination with the dual-set of front and rear programmable LED light patterns, the corneal reflections can be identified and, thus, the XYZ position and tip/tilt of internal elements can be determined.

Figure 1:
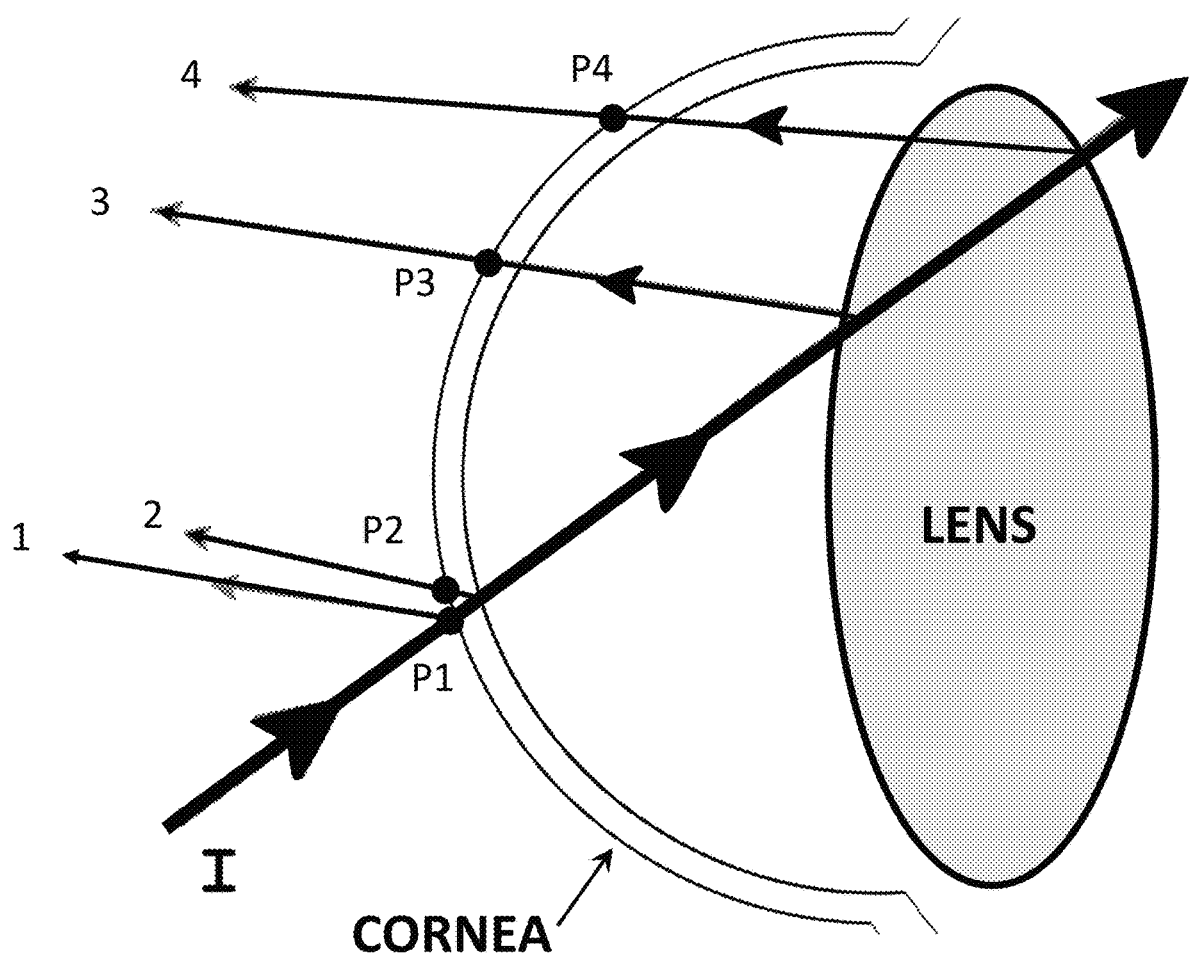
FIG. 1 shows a schematic cross-section view of an eye illustrating the light rays that generate the four Purkinje images [22].
Figure 2:
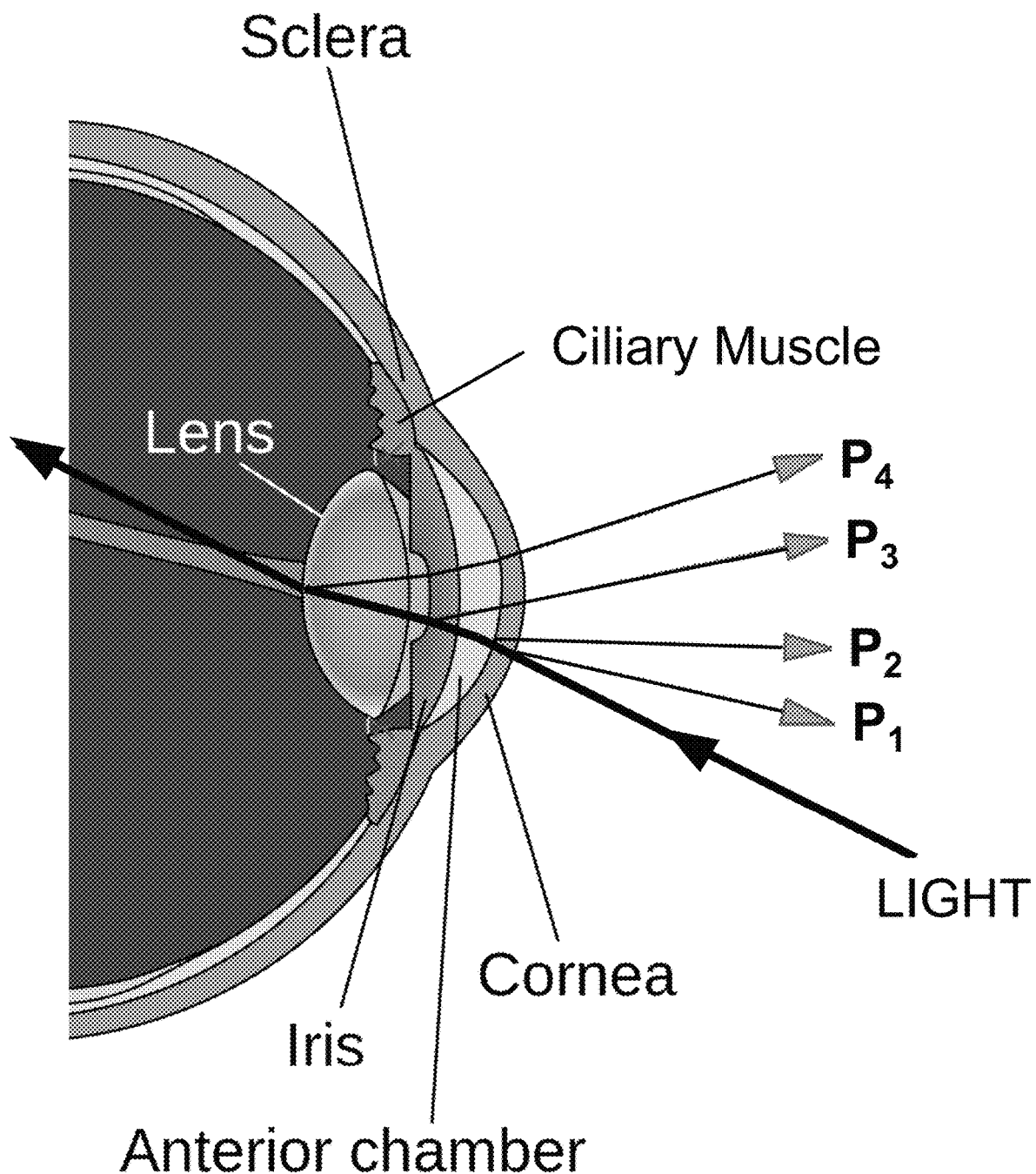
FIG. 2 shows a schematic cross-section view of an eye illustrating the light rays that generate the four Purkinje images.
Figure 3:
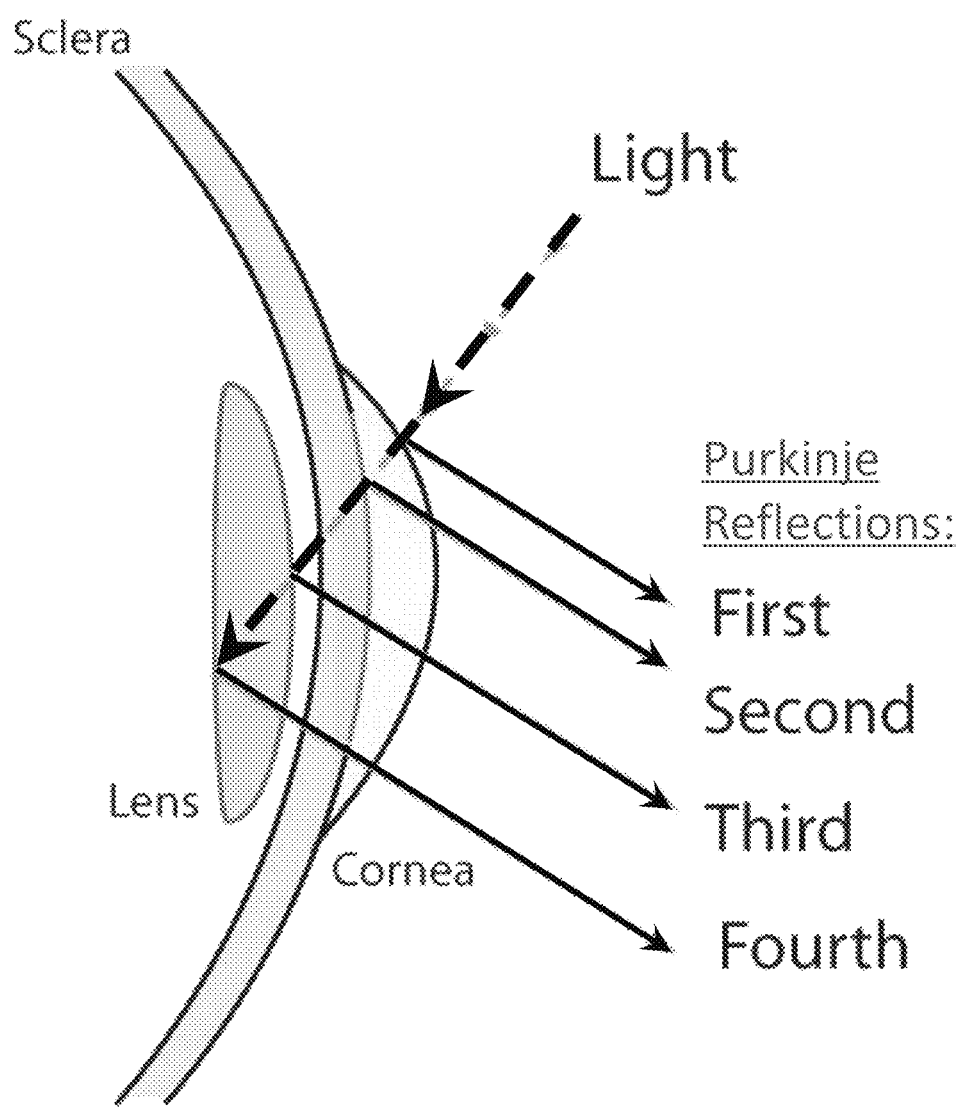
FIG. 3 shows a schematic cross-section view of an eye illustrating the light rays that generate the four Purkinje images [16].
Figure 4:
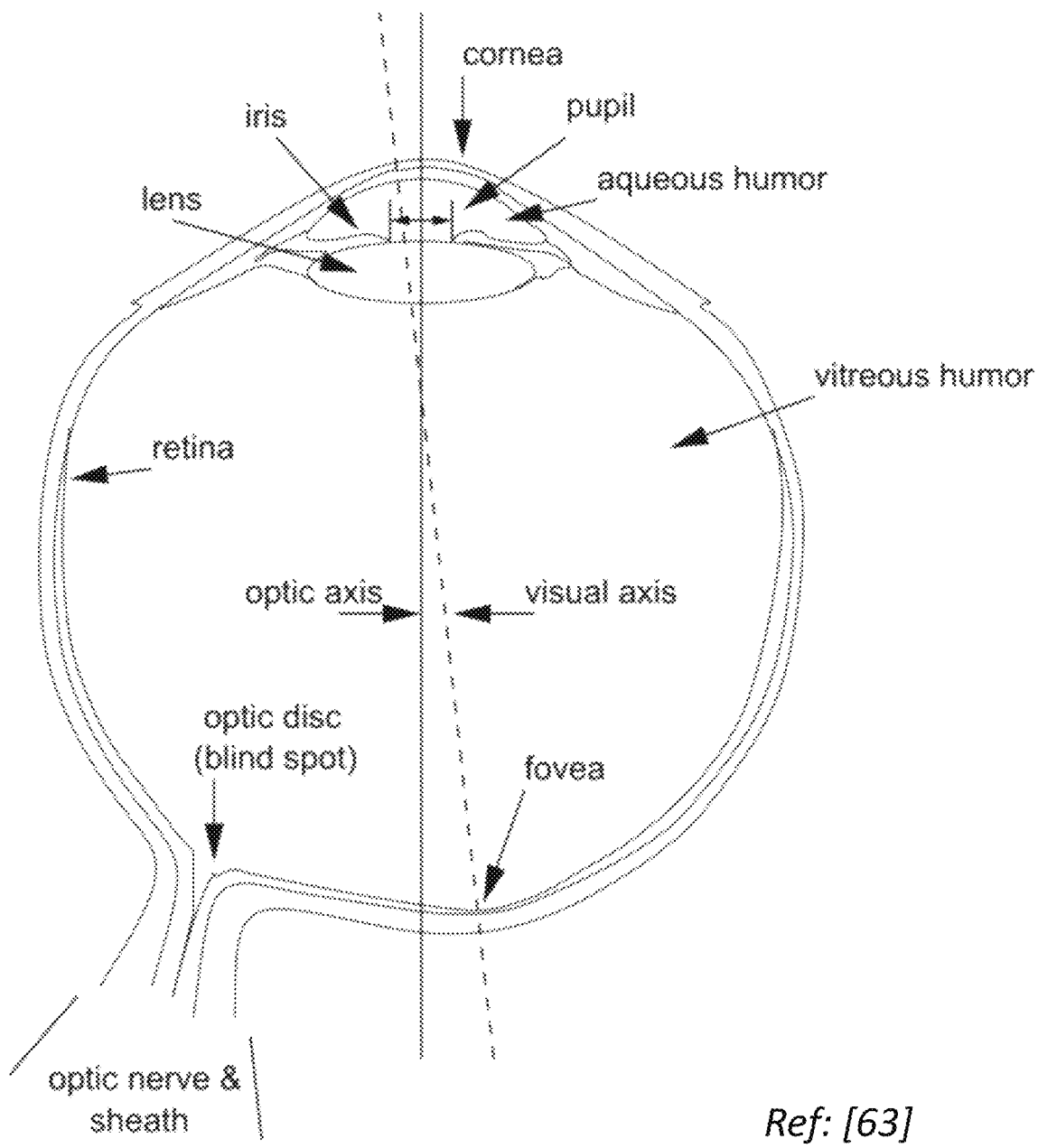
FIG. 4 shows a schematic cross-section view of an eye illustrating the anatomy of the eye [63].
Figure 5:
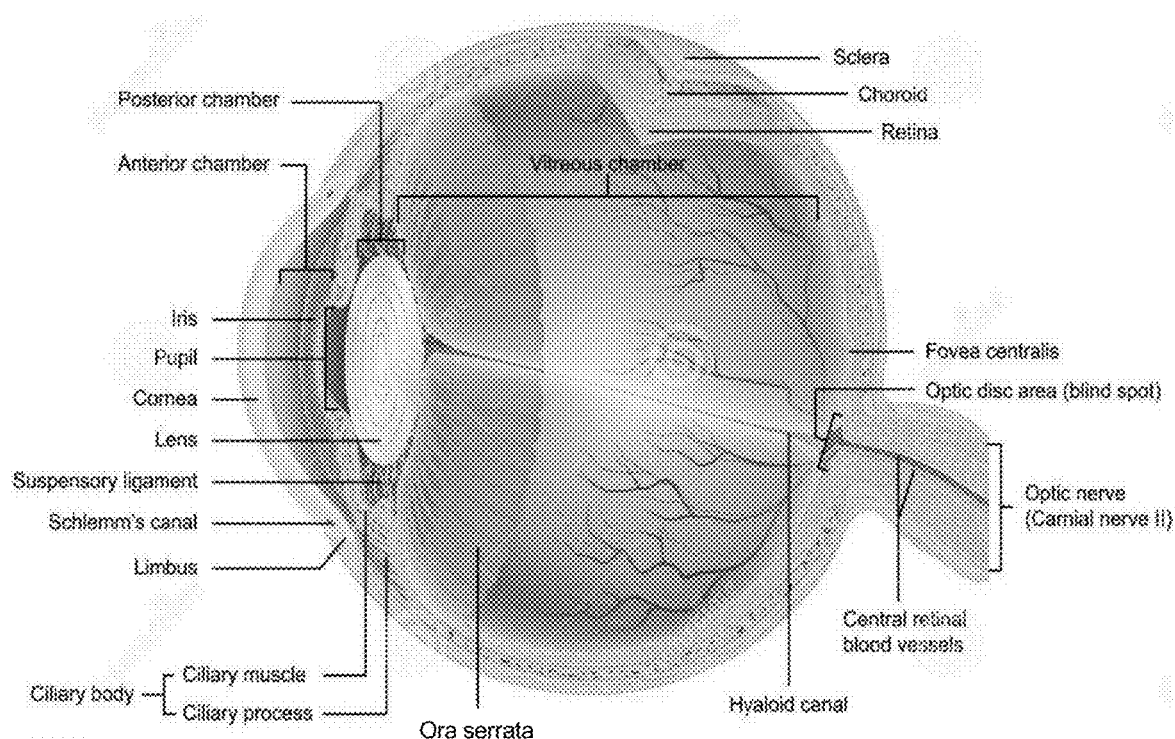
FIG. 5 shows a schematic cross-section view of an eye illustrating the anatomy of the eye [63].
Figure 6:
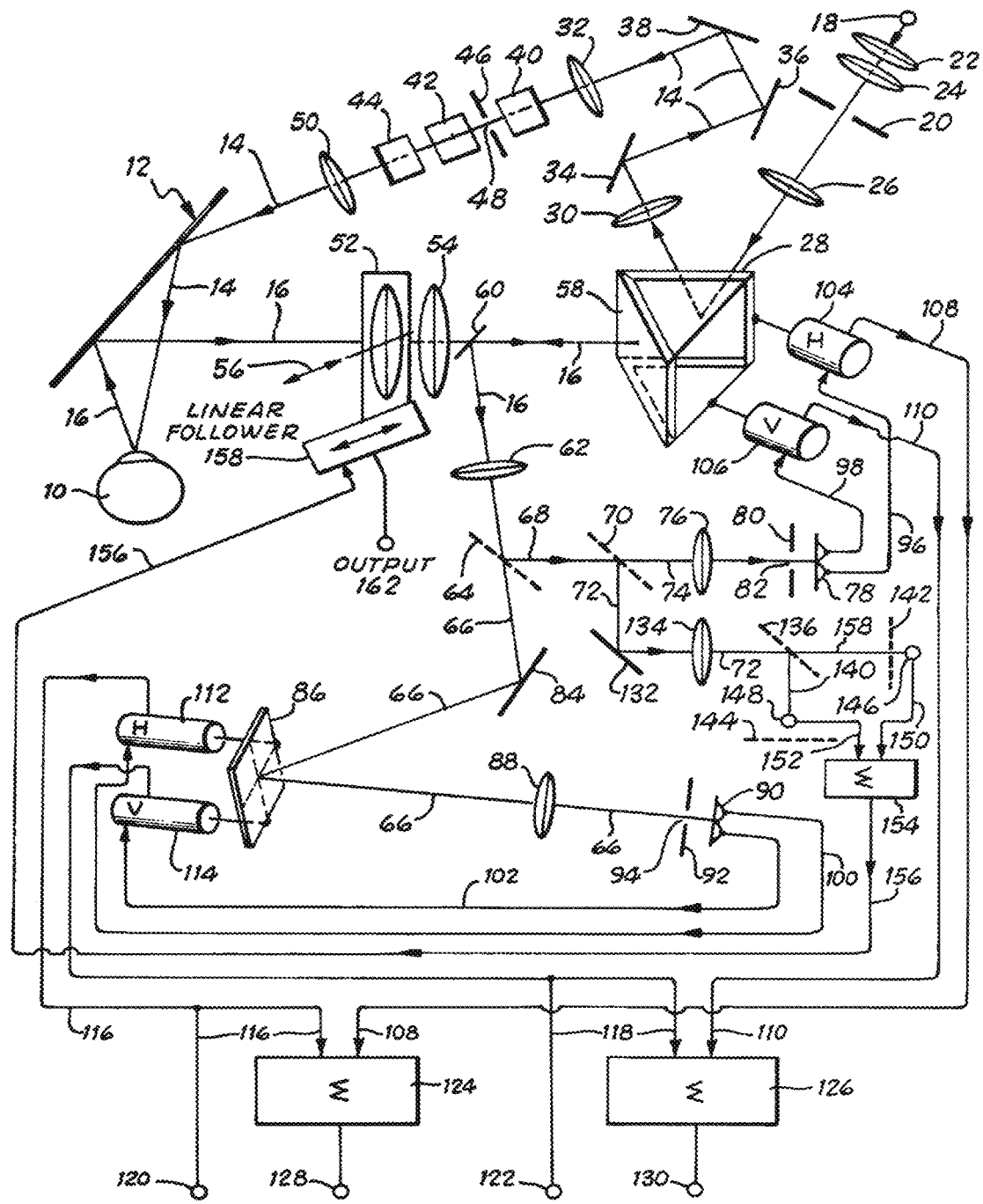
FIG. 6 shows a schematic view of a Dual-Purkinje eye-tracker optical system [27].
Figure 7:
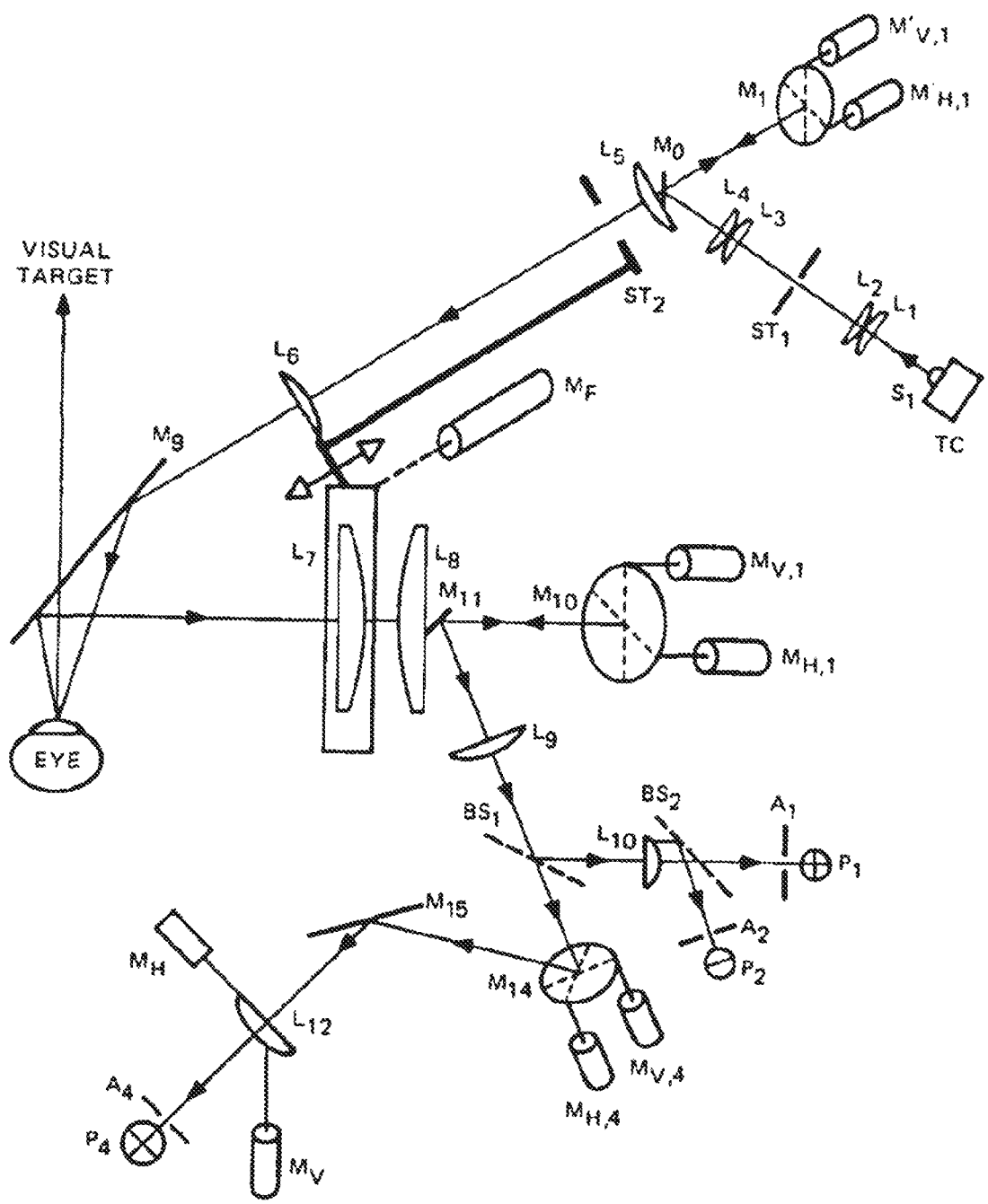
FIG. 7 shows a schematic view of a Dual-Purkinje eye-tracker optical system [1].
Figure 8:
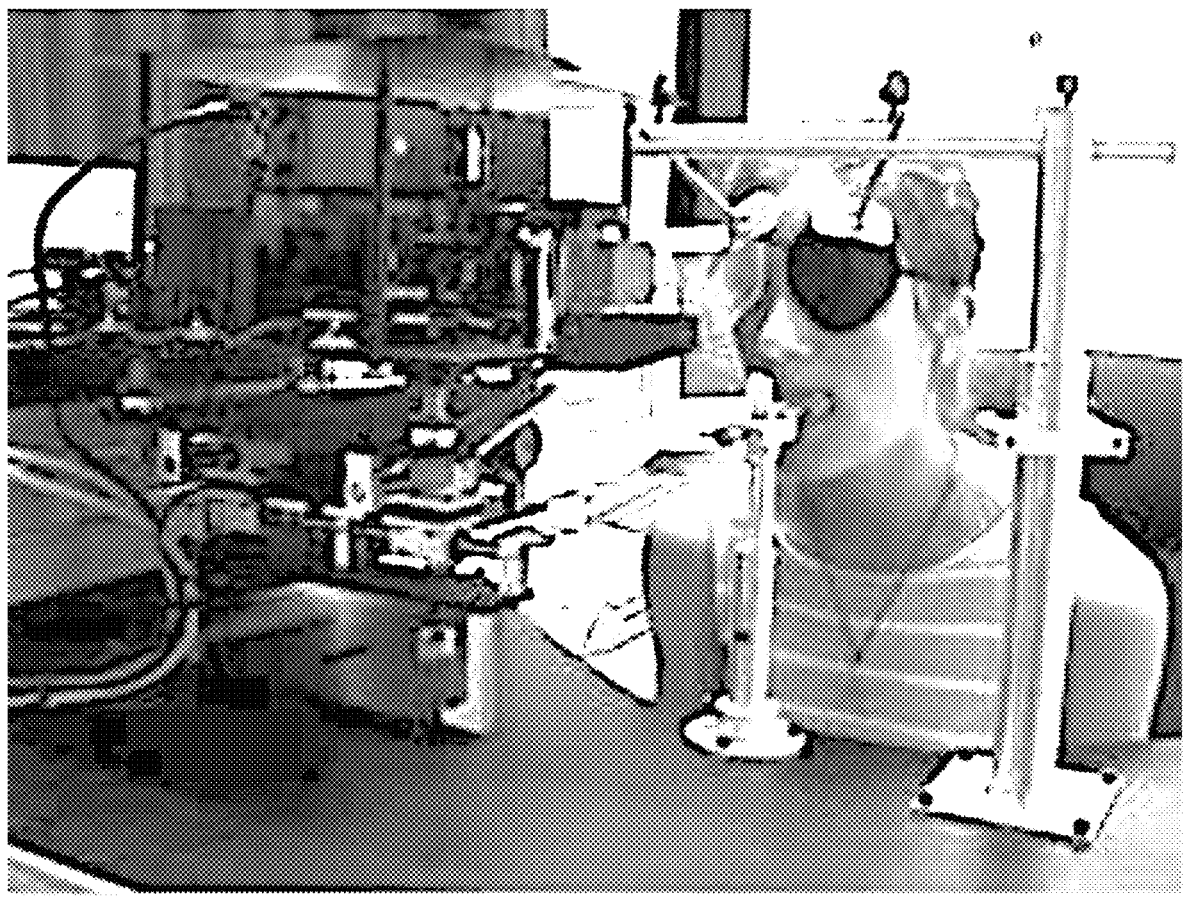
FIG. 8 shows a photograph of a Dual-Purkinje eye-tracker system by Crane & Steele [8].
Figure 9A:
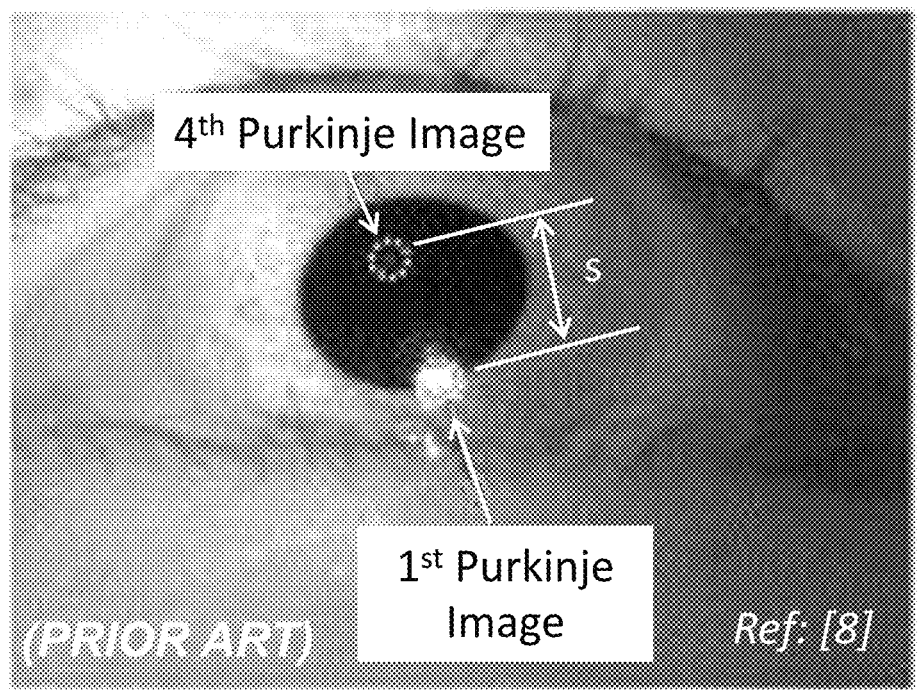
FIG. 9A shows a photograph of an eye and pupil with 2 different types of Purkinje images [8].
Figure 9B:
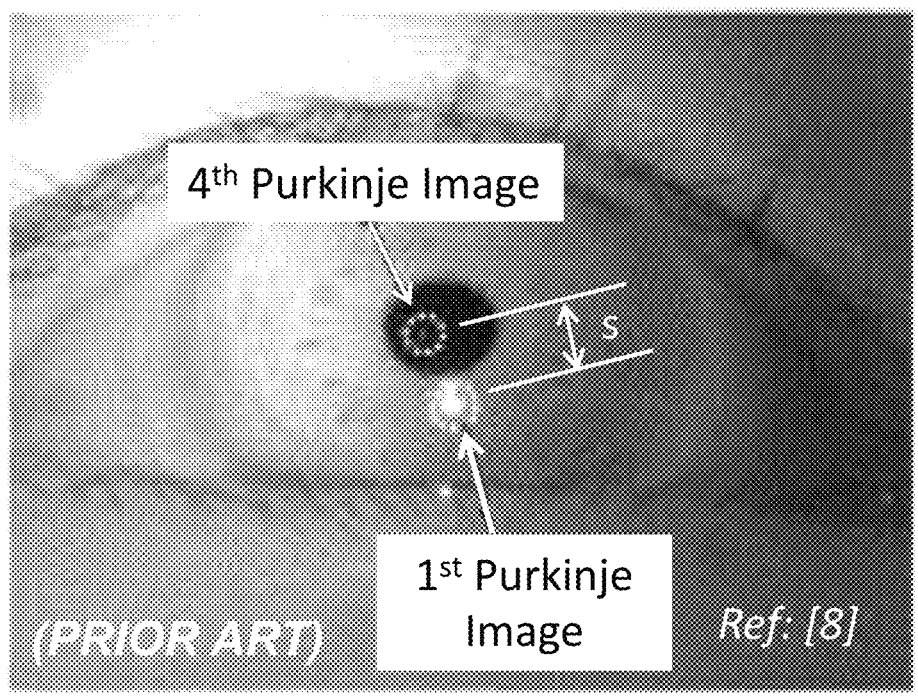
FIG. 9B shows a photograph of an eye and dilated pupil with 2 different types of Purkinje images, $P_1$ and $P_4$ [8].
Figure 10:
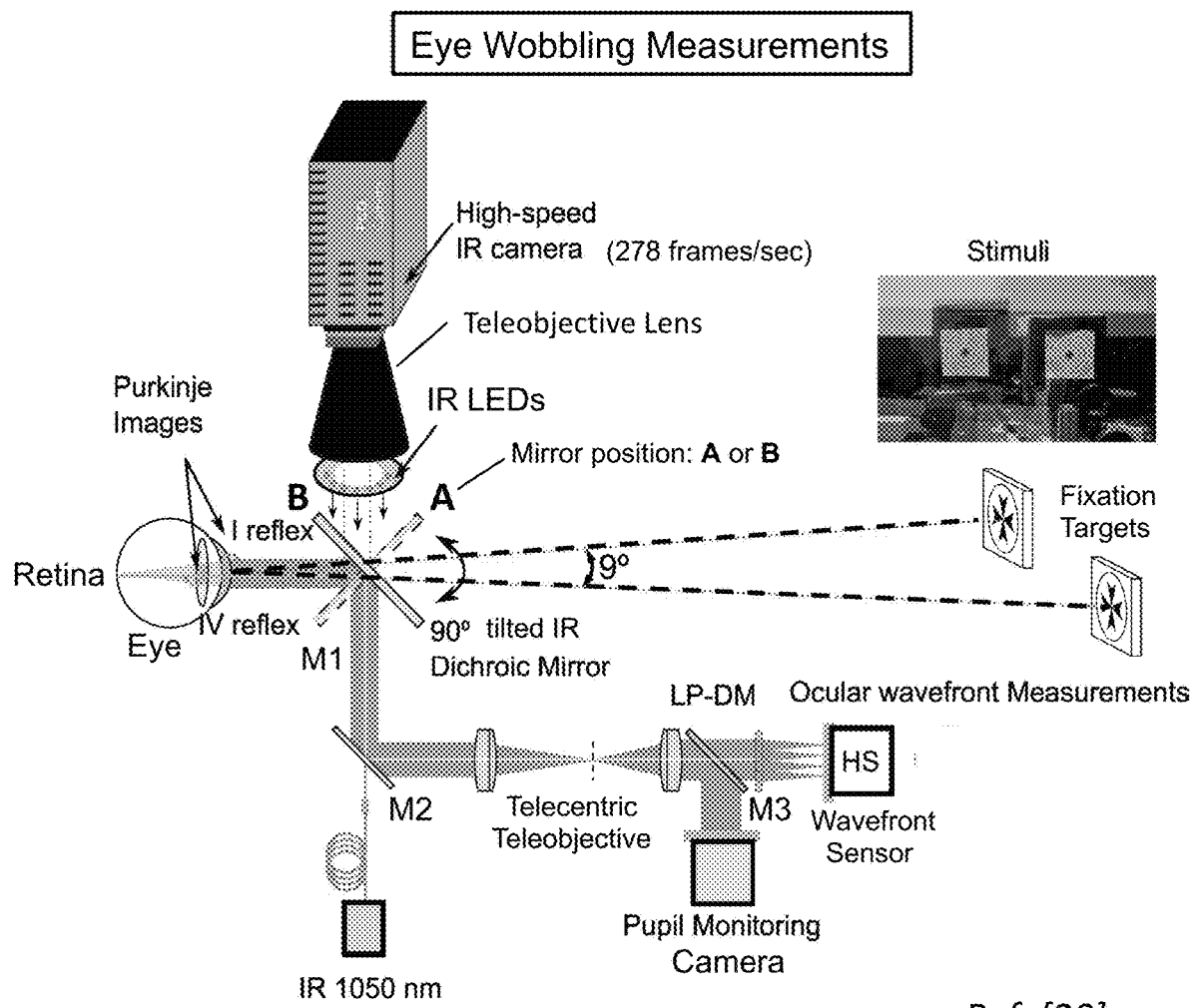
FIG. 10 shows a schematic view of a Dynamic Purkinje-Meter (DPM) optical eye-tracking system, by Tabernero, et al. [20].
Figure 11:
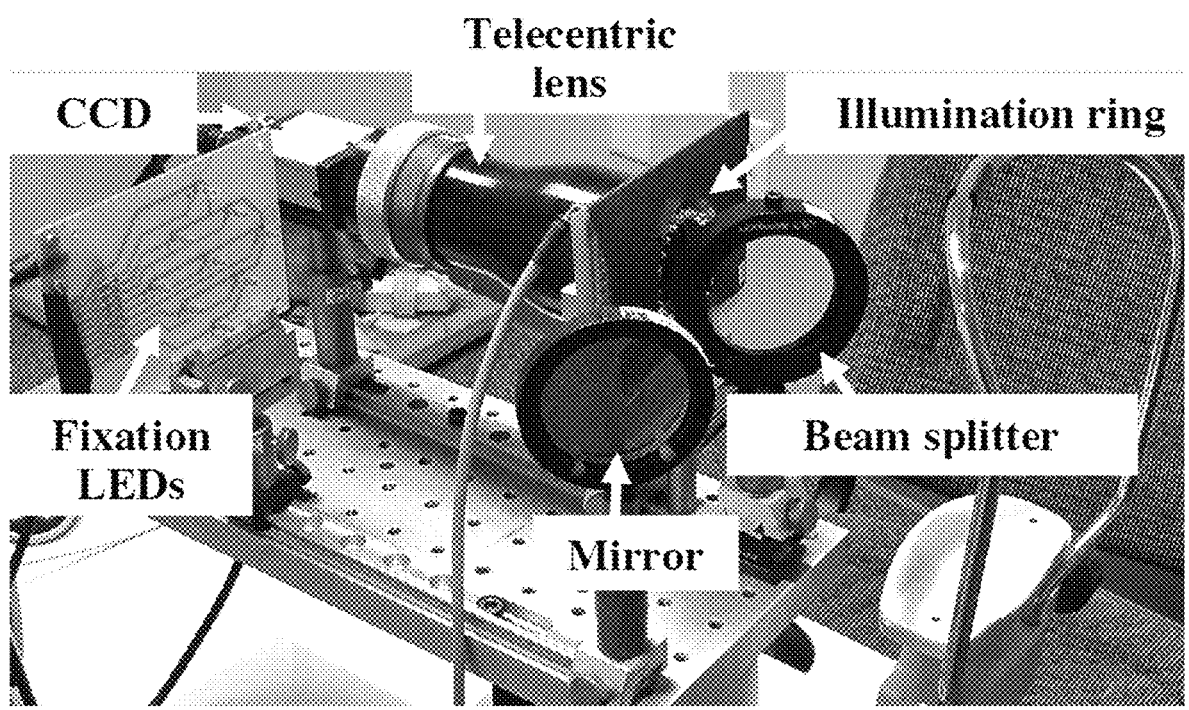
FIG. 11 shows a photograph of a Dynamic Purkinje-Meter (DPM) optical eye-tracking system by Tabernero, et al. [14].
Figure 12:
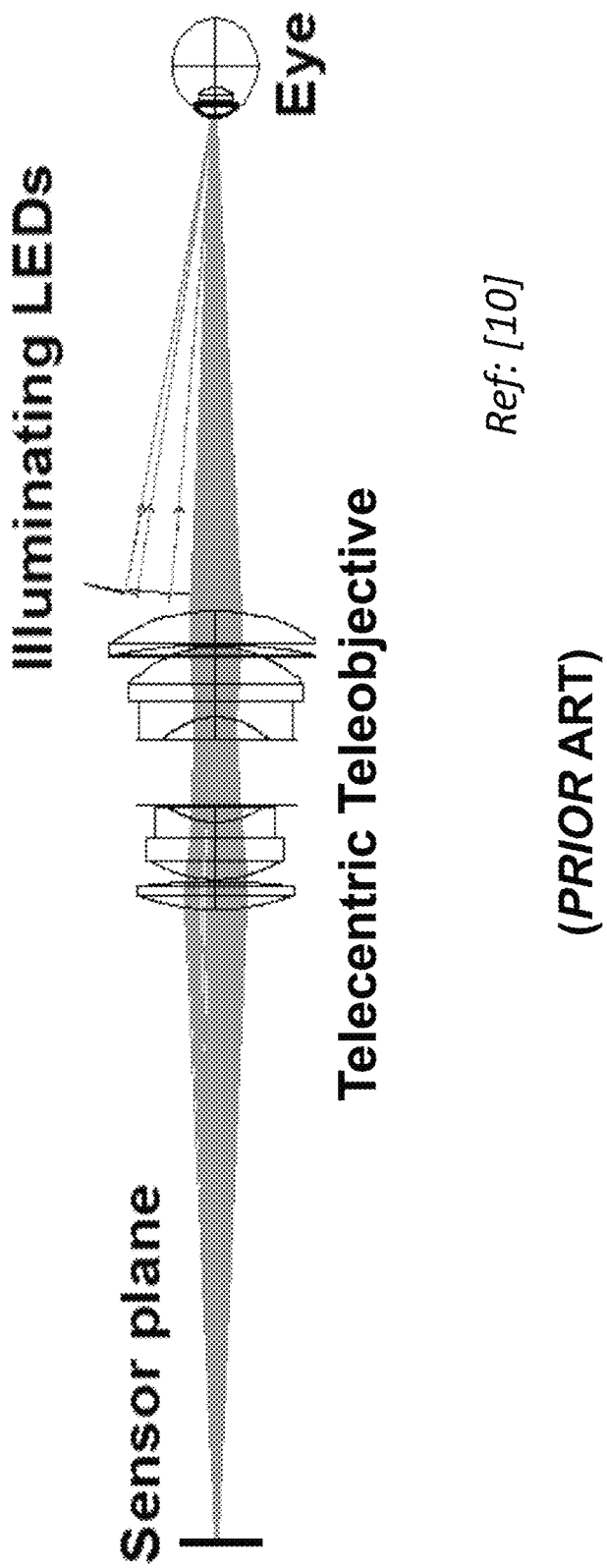
FIG. 12 shows a schematic view of a Dynamic Purkinje-Meter (DPM) optical eye-tracking system by Tabernero, et al. [10].
Figure 13A:
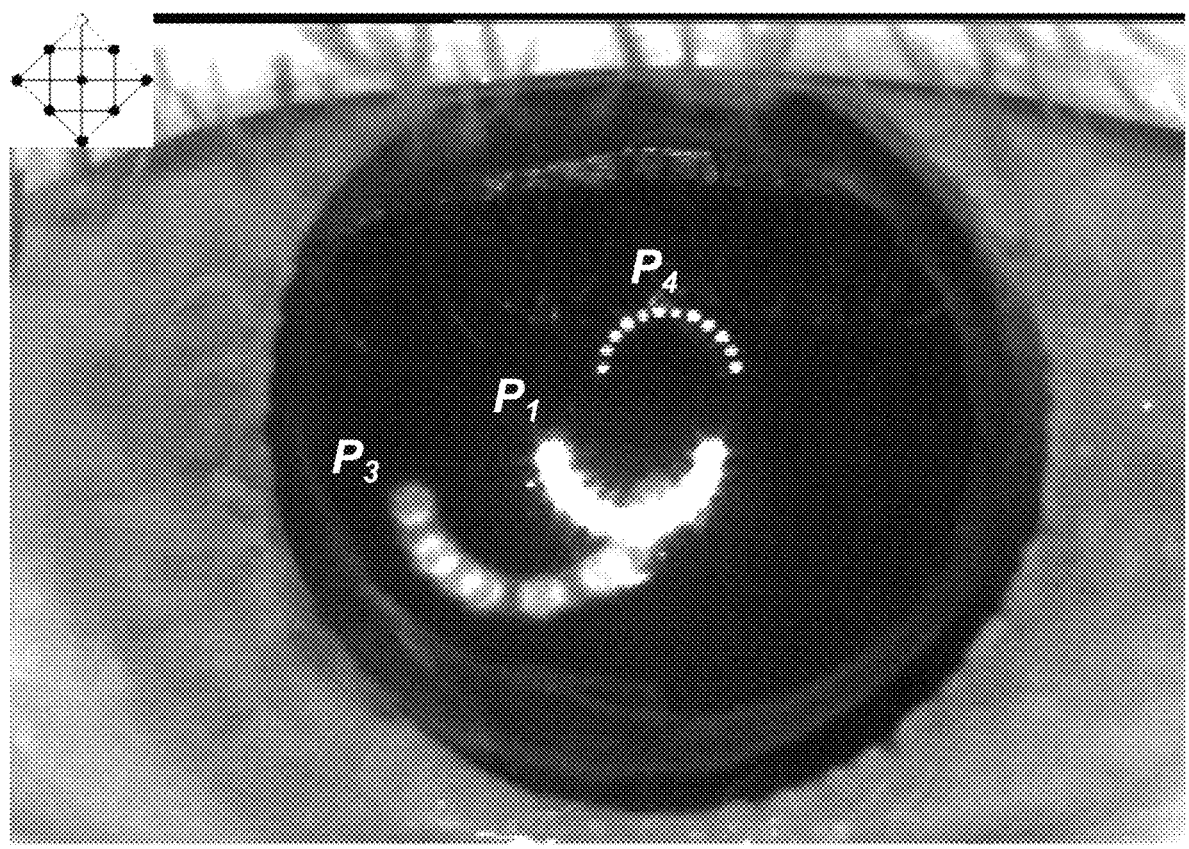
FIG. 13A shows a photograph of a dilated pupil with 3 different Purkinje images reflected in the cornea [14].
Figure 13B:
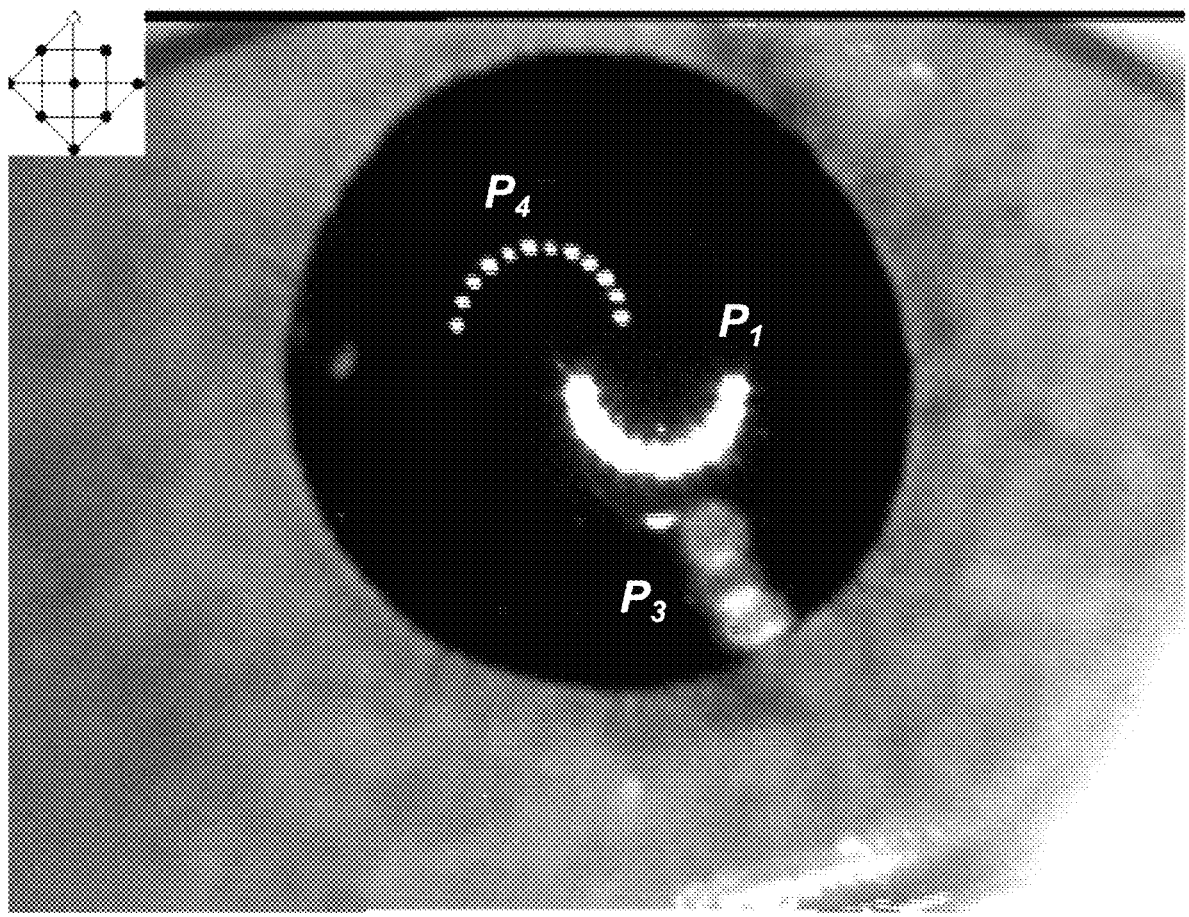
FIG. 13B shows a photograph of a dilated pupil with 3 different Purkinje images reflected in the cornea [14].
Figure 14A:
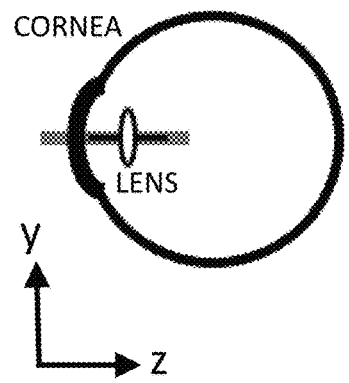
FIG. 14A shows a cross-section side view of computer simulation model of a human eye with a lens that has zero decentration offset of the lens [20].
Figure 14B:
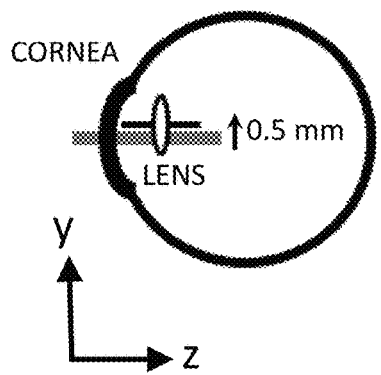
FIG. 14B shows a cross-section side view of computer simulation model of a human eye with a lens that has a 0.5 mm vertical decentration offset of the lens [20].
Figure 14C:
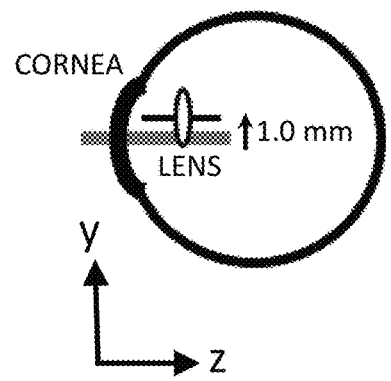
FIG. 14C shows a cross-section side view of computer simulation model of a human eye with a lens that has a 1.0 mm vertical decentration offset of the lens [20].
Figure 15A:
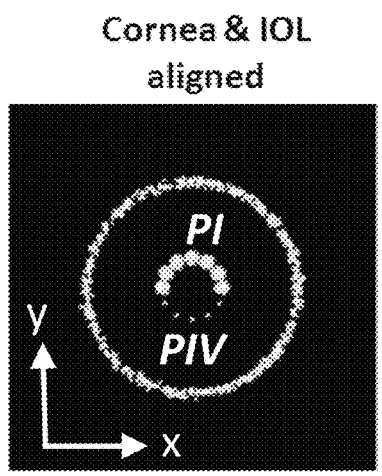
FIG. 15A shows a computer simulation of Purkinje images inside the pupil area with zero decentration offset of the lens [20].
Figure 15B:
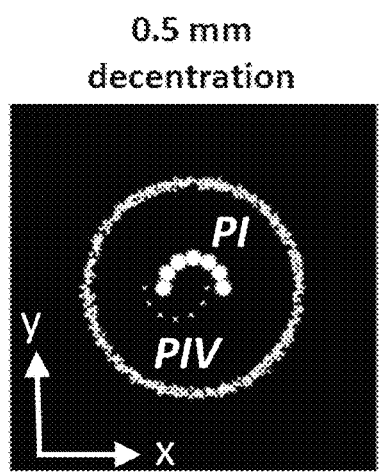
FIG. 15B shows a computer simulation of Purkinje images inside the pupil area with a 0.5 mm vertical decentration offset of the lens [20].
Figure 15C:
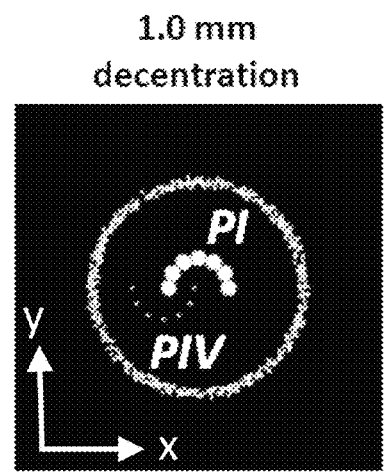
FIG. 15C shows a computer simulation of Purkinje images inside the pupil area with a 1.0 mm vertical decentration offset of the lens [20].
Figure 16:
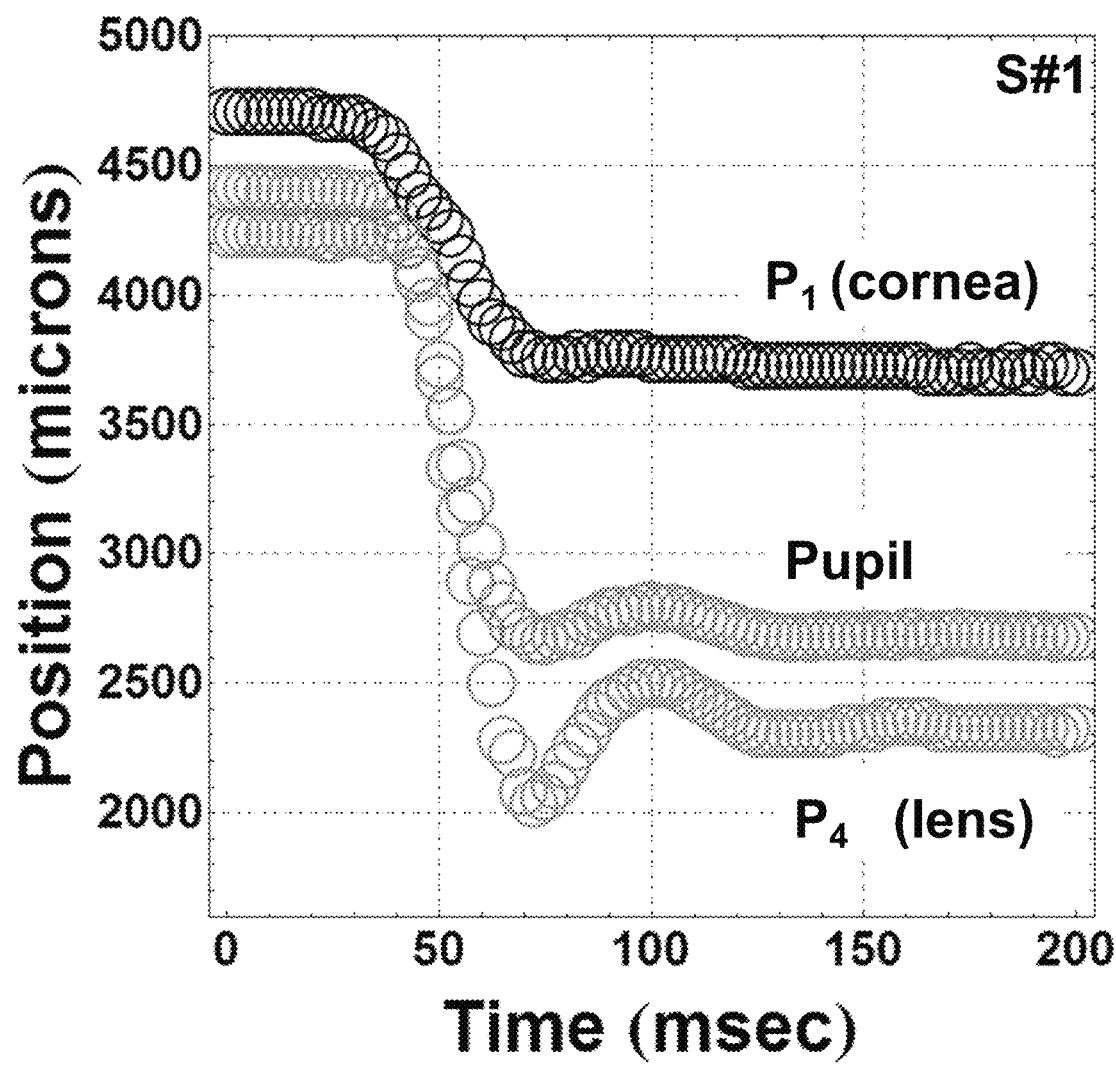
FIG. 16 shows a plot of the dynamic (temporal) response of the position of the pupil, cornea, and lens after a saccadic motion was initiated at t=40 msec, as measured with the Dynamic Purkinje-Meter eye-tracking system of Tabernero, et al. [20].
Figure 17:
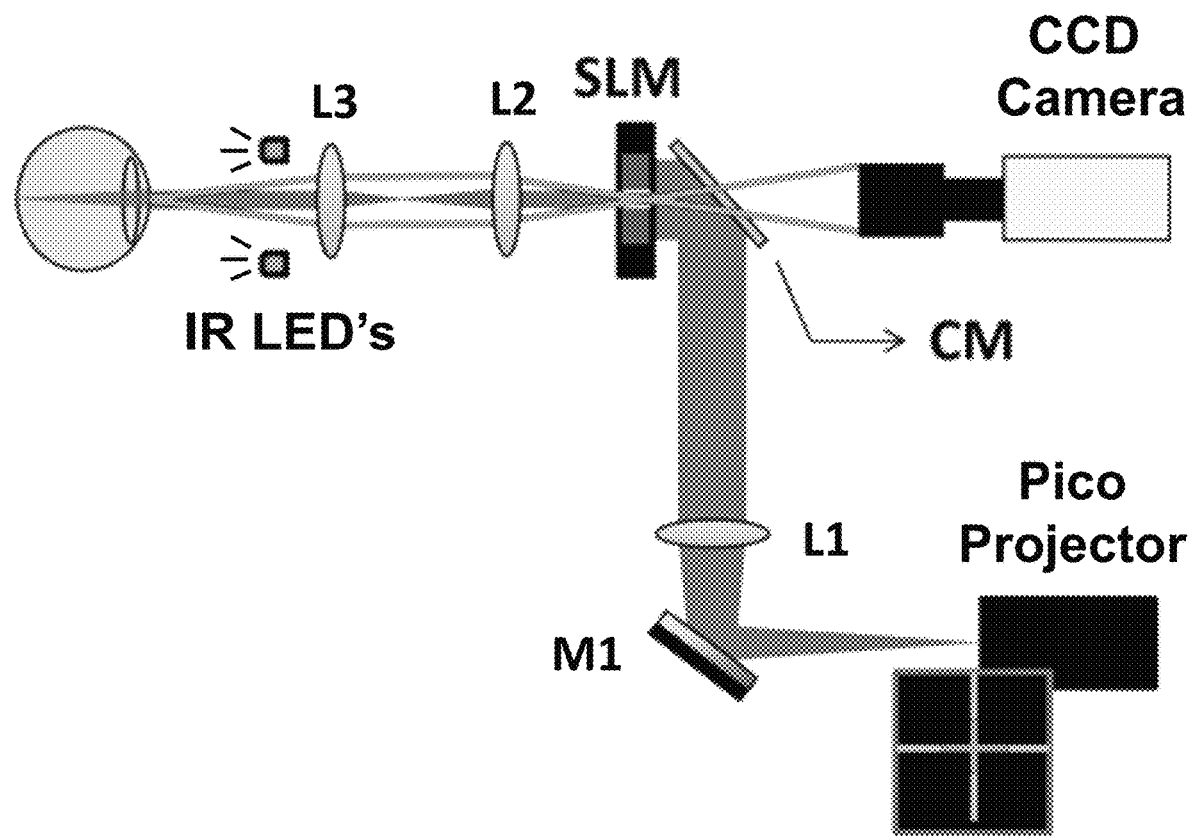
FIG. 17 shows a schematic view of an optical system for tracking eye motion using the first Purkinje image $P_1$ [11].
Figure 18:
FIG. 18 shows an isometric photograph of a compact eye-tracking instrument called "Cassini Ambient" [5].
Figure 19:
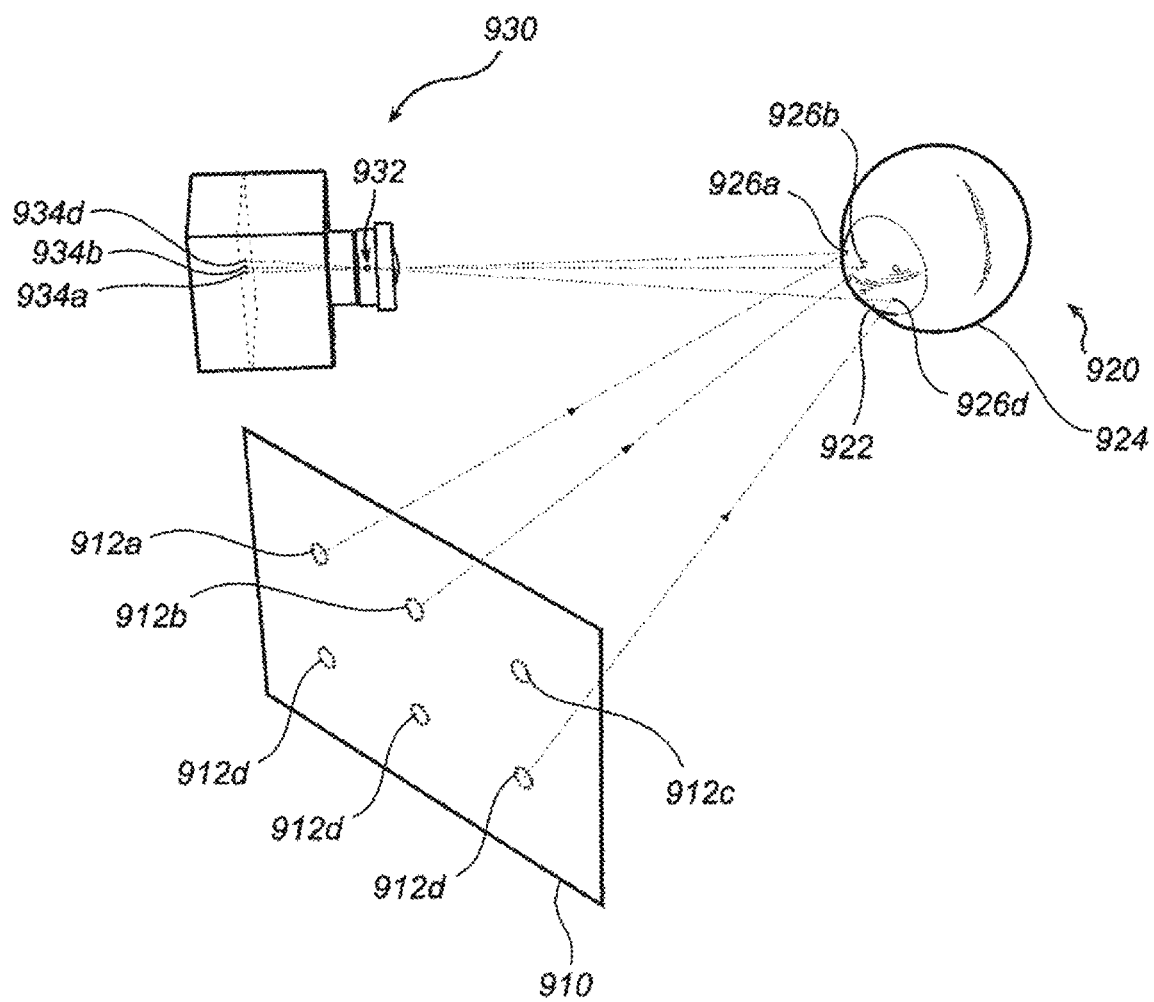
FIG. 19 shows a schematic view of an optical system for tracking eye motion using the first Purkinje image, $P_1$ [58].
Figure 20:
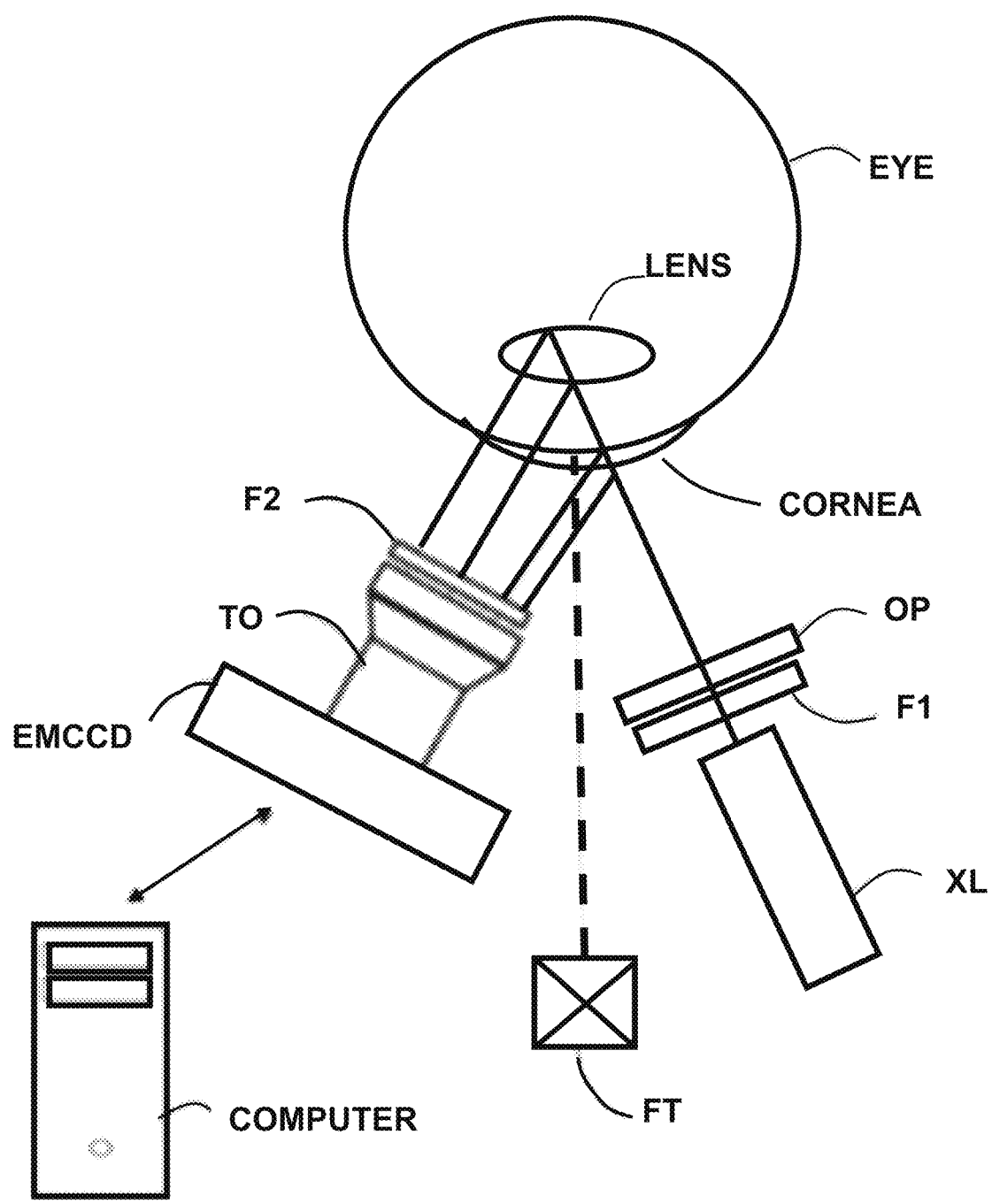
FIG. 20 shows a schematic view of an optical system for tracking eye motion using Purkinje images [4].
Figure 21:
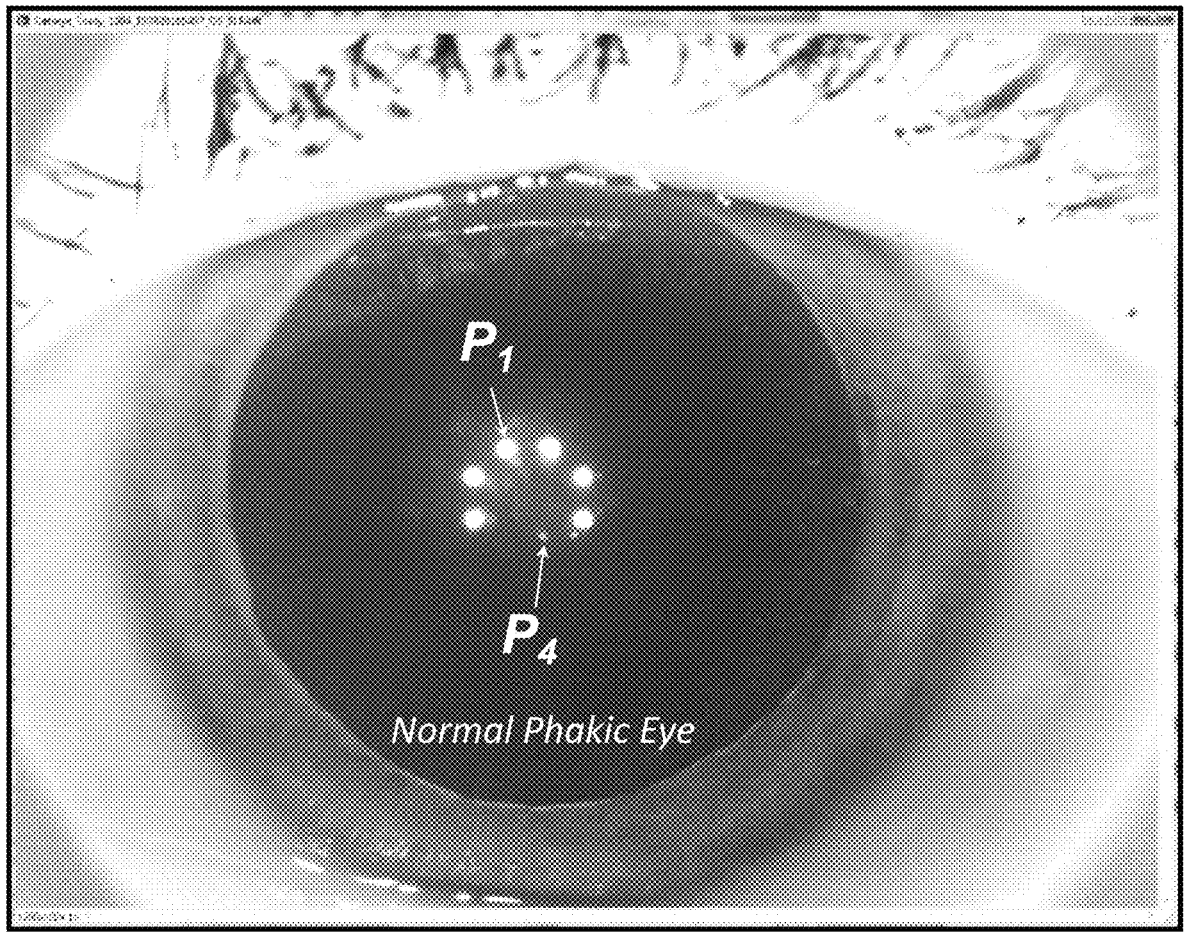
FIG. 21 shows a magnified photograph of a normal phakic eye with a natural lens and dilated pupil displaying $1^{st}$ and $4^{th}$ Purkinje images ($P_1$ reflecting from the front surface of the cornea, and $P_4$ reflecting from the posterior surface of the lens), taken with a Purkinjenator™ optical device, according to the present invention.
Figure 22:
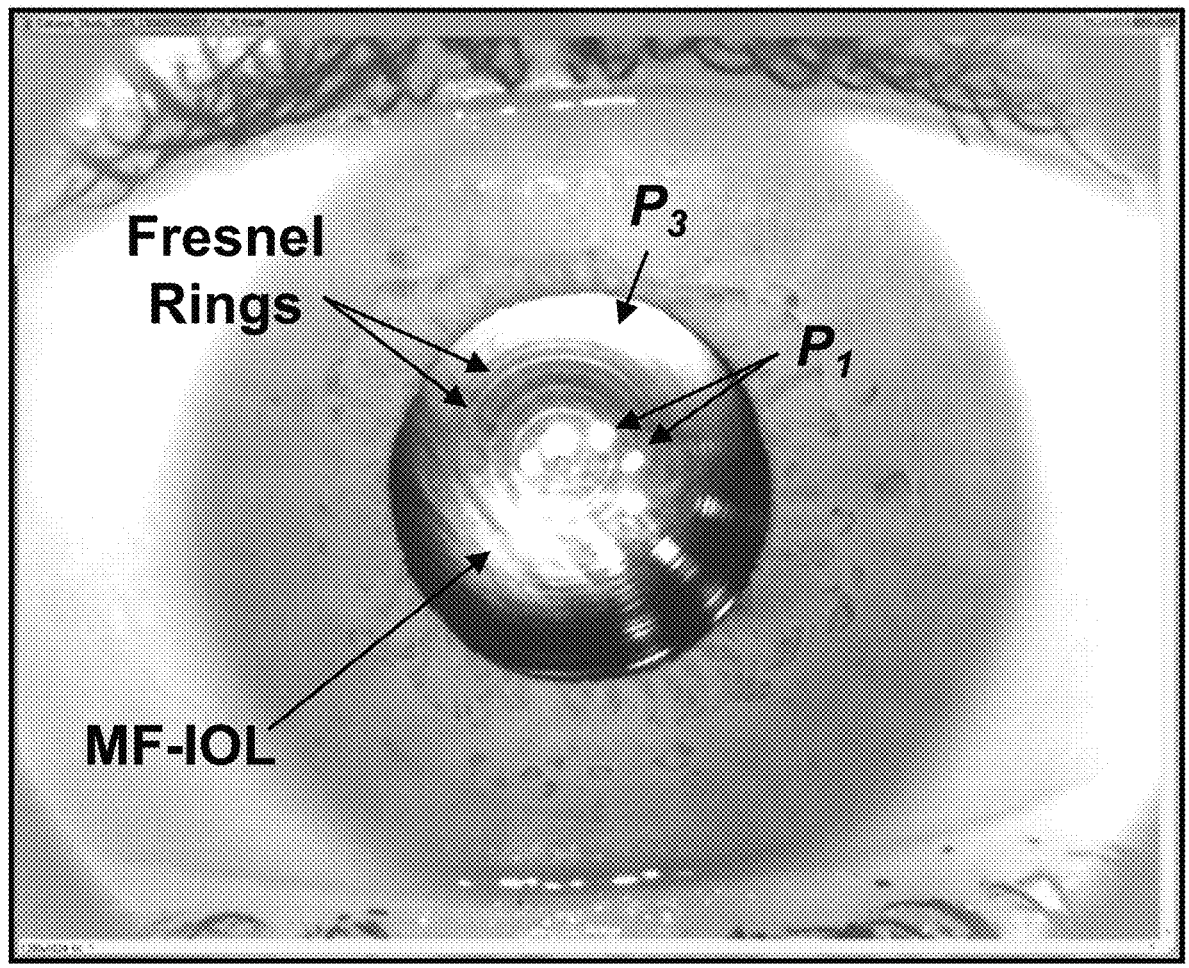
FIG. 22 shows a magnified photograph of an eye with a diffractive multi-focal IOL (MF-IOL) implanted within the eye, taken by a Purkinjenator™ optical device; where the large white spot nearly filling the pupil is the third Purkinje image, $P_3$ (reflection from the front surface of the IOL), according to the present invention.
Figure 23:
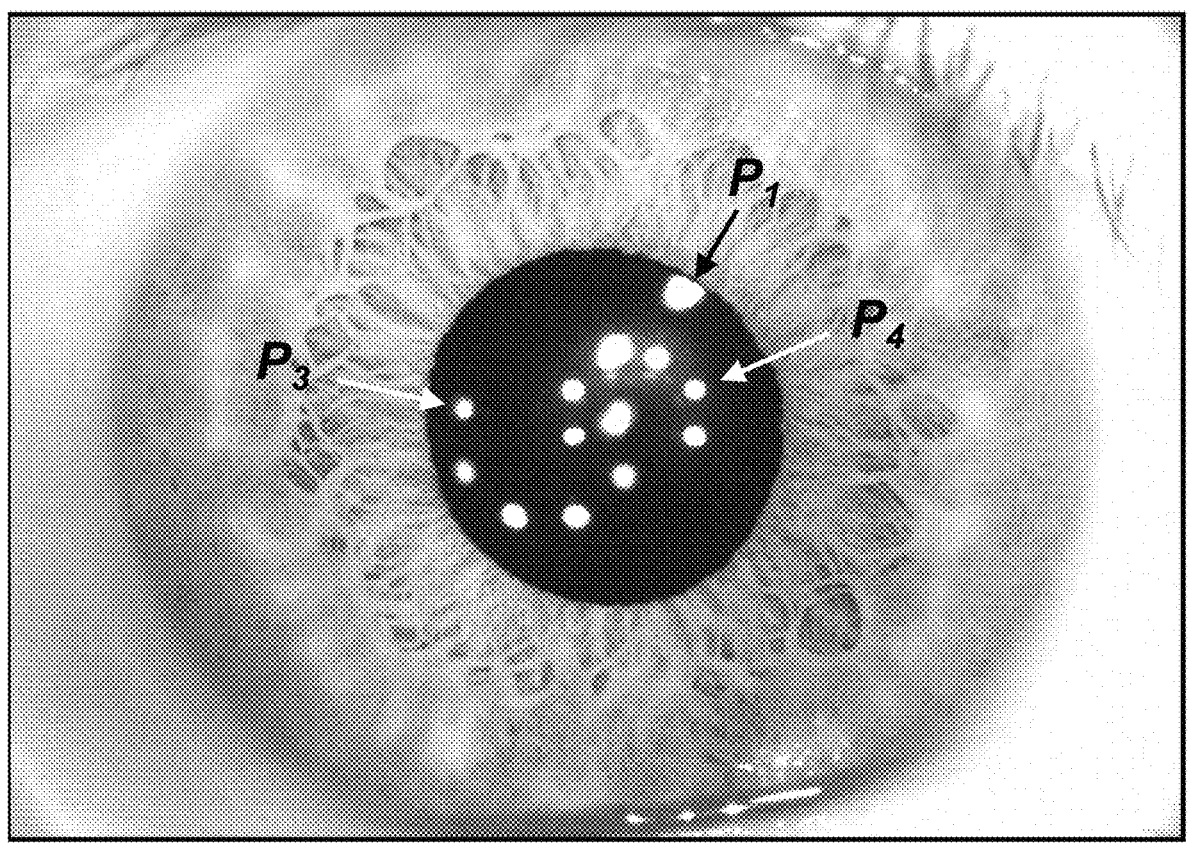
FIG. 23 shows a magnified photograph of an eye with an implanted, single-focus (monofocal) IOL, with the photograph taken by a Purkinjenator™ optical device, according to the present invention.

Helmholtz light sources 31 of the present invention can originate much closer to the optical axis of the instrument than the conventional outer ring of LED sources used by Tabernero and Artal (see FIGS. 10 and 11). This is beneficial for IOL measurement because the Helmholtz reflections will tend to provide more compact and better-defined Purkinje images than the complex $P_3$ reflections shown, for example, in FIG. 22. Firmware control of the LEDs can be used; either as individually-controlled and individually-addressable LEDs, or in specific groups or patterns.

The "U"-shaped semi-circular pattern is a useful and convenient pattern for explanations in this disclosure. However, a computer-controlled system does not need to be constrained to using such a U-shaped pattern. A regular (periodic or patterned) grid (which can be a rectangular or circumferential array) of LEDs may be used instead of a semi-circular ring of lights, with each LED lit up individually, or in multiple groups or patterns sequentially. Sequential camera-frames can be compared on the basis of relative spot motion between frames, and the front and back surfaces of the IOL discriminated on that basis, using well-known motion-capture software algorithms. To enable more robust calculation of relative spot motion, it may be desirable to arrange the additional light sources horizontally (i.e., along the X-direction).

The first step in the analysis methodology is associating each light spot in the image with a particular LED (Front and/or Rear LEDs). Each LED creates four light spots: two from the cornea ($P_1$ and $P_2$), one from the front of the IOL ($P_3$), and one from the back of the IOL ($P_4$). $P_3$ and $P_4$ can be distinguished by moving the entire instrument (camera and light sources) relative to the eye because they move different directions on the image. A second method is the camera can remain stationary and the light source pattern moved. A third method is as follows: the movement effect can be created by having two light sources near each other that are sequentially and alternately turned on and off and are observed in synchronization on sequential camera images. In one embodiment, the two light sources are displaced horizontally so it is easy to describe the apparent motion of P3 as being left-to-right (when P4 motion is right-to-left). However, in general the displacement can be along any axis, and the apparent motion can be described as radial displacement toward or away from the center of an image.

$P_1$ and $P_2$ overlap and cannot be easily distinguished from each other, so these will be referred to as "$P_1$&$P_2$". $P_1$ is especially bright because it is formed at an interface exposed to air, whereas $P_2$, $P_3$ and $P_4$ are dimmer because they come from interfaces immersed in fluid. This difference in reflected intensity makes it so $P_1$&$P_2$ can be easily distinguished from $P_3$ and $P_4$ by intensity if an instrument is properly configured. Most eye-tracking devices that illuminate the eye with LEDs are configured so all the Purkinje spots are saturated on the camera image. However, if the LED intensity is reduced, the apparent brightness of the $P_3$ and $P_4$ can be in the middle of the sensitivity range of the camera. For example, if the numerical maximum of a camera pixel is 256, the brightness of $P_3$ and or $P_4$ could be anywhere between 50 and 200. At the same time, the brightness of $P_1$&$P_2$ would read out as 256. So, the combination of appropriate LED brightness, along with sequential LED lighting, can uniquely identify each spot of light as being $P_1$, $P_2$, $P_3$ or $P_4$.

A disadvantage of using reduced LED brightness, however, is that the camera image will not capture the iris details of the eye, including the iris-pupil boundary. In some applications (but not all) it is desired to know the location of the Purkinje image, and hence the IOL, relative to the iris boundary. One solution that works in concert with the embodiment described above is to simply add an image capture in the sequence where the LED brightness is increased.

An alternate method is pupil retro-illumination, which is a well-known technique. It requires an additional LED to shine into the eye and focus on the retina so that light scattering back out of the pupil creates an illuminated disc. It is frequently used to evaluate IOL placement, particularly with a dilated pupil to reveal the IOL edges, support haptic, and fiducial marks of the IOL (if present). If such an LED is added to the system for pupil retro-illumination, it is simplest to add one more image capture in the entire capture sequence.

To calculate the tip or tilt angle of an IOL, at least two LEDs need to be used to generate Purkinje images. As discussed above, a first pair of adjacent LEDs can be used to differentiate $P_3$ and $P_4$, but if they are located near each other (so the region sampled on the IOL would be very close), it would be difficult to calculate the IOL tilt with a high degree of accuracy. A better measurement of tilt can be obtained with the inclusion of an analysis of the reflections from a second pair of LEDs that are separated some distance from the first pair of LEDs. Some of these LEDs are separated on the front set of LEDs. Others are separated on the rear set of LEDs.

It can sometimes happen that Purkinje images from a single LED can overlap. For example, the spot formed by the overlapping $P_1$ and $P_2$ may overlay $P_3$ on the image. When that happens, it is not possible to use that image for calculating the IOL position and tilt. With conventional clinical instruments, when that occurs, an operator would move the instrument sideways until a spot was found where those Purkinje images did not overlap. Similarly, in a preferred embodiment of this invention, there can be a multitude of light source pairs, perhaps somewhere between 10 and 100 pairs, each consisting of a pair of LEDs. The system would sequentially light up each LED. The ones that are useful have spots formed by $P_1$&$P_2$ and $P_3$ and $P_4$ that are clearly and cleanly separated (with no overlap). With a large number of LEDs, it will be assured that there will at least three or more pairs of spots that exhibit clearly-separated spots, so that accurate calculation of IOL position and tilt can be performed.

Further, real-time analysis of the images can be performed so the system learns which LEDs are providing useable images. The software can then adapt and only activate (light up) only those LEDs that are useful in order to improve the overall speed of the monitoring of the IOL's position in real-time.

A further optimization of the capture sequence can be achieved by recognizing that LEDSs on one side of eye only create Purkinje images on that side of the image. So widely separated LEDs can be turned ON at the same time and the analysis software can associate LEDs to spots on the eye without ambiguity.

For normal eyes, it is very distinct that LEDS on the one side of the eye only create Purkinje images on that side of the image. However, some eyes have a very large decentration of the natural lens or IOL relative to the corneal apex, resulting in Purkinje images that are widely spaced. Such eyes can be identified with the flash of a single LED and analysis of a single frame. When an unusual eye like that is encountered, the software can execute an option where the number of LEDs that are turned ON simultaneously is reduced, possibly down to a single LED per camera frame, to ensure unambiguous Purkinje spot identification and association to LEDs.

One useful arrangement of the Front and/or Rear LED sources (or both) would be in a regular XY grid, with each light source in the grid consisting of two LEDs, 200 and 202, that are each arranged to be on radial lines emanating from the center. However, it can be appreciated that when the XY grid becomes sufficiently dense, there could be a shortage of space for LED pairs for each grid location. In that case, the grid comes to resemble simply a dense XY grid of LEDs. The key inventive aspect of using that grid effectively is that sequential camera frames are taken with only a few distant LEDs lit up in any single frame, but in the following frame, the LEDs that are lit up are ones that are near neighbors to those in the previous frame. Then the software will analyze LED patterns with spot motion algorithms as previously mentioned, to differentiate between $P_3$ and $P_4$ spots.

In summary, tracking of Purkinje images using a Purkinjenator™ device allows for XY and Z positions to be determined in real-time. When used in combination with adaptable LED light source patterns, reflections from internal surfaces and corneal surfaces can be identified in real-time, and thus XYZ position and tip/tilt of internal structures can be determined using the thin-lens equations written for each surface and light source and then solved algebraically (or by using optical raytracing techniques).

Figure 32:
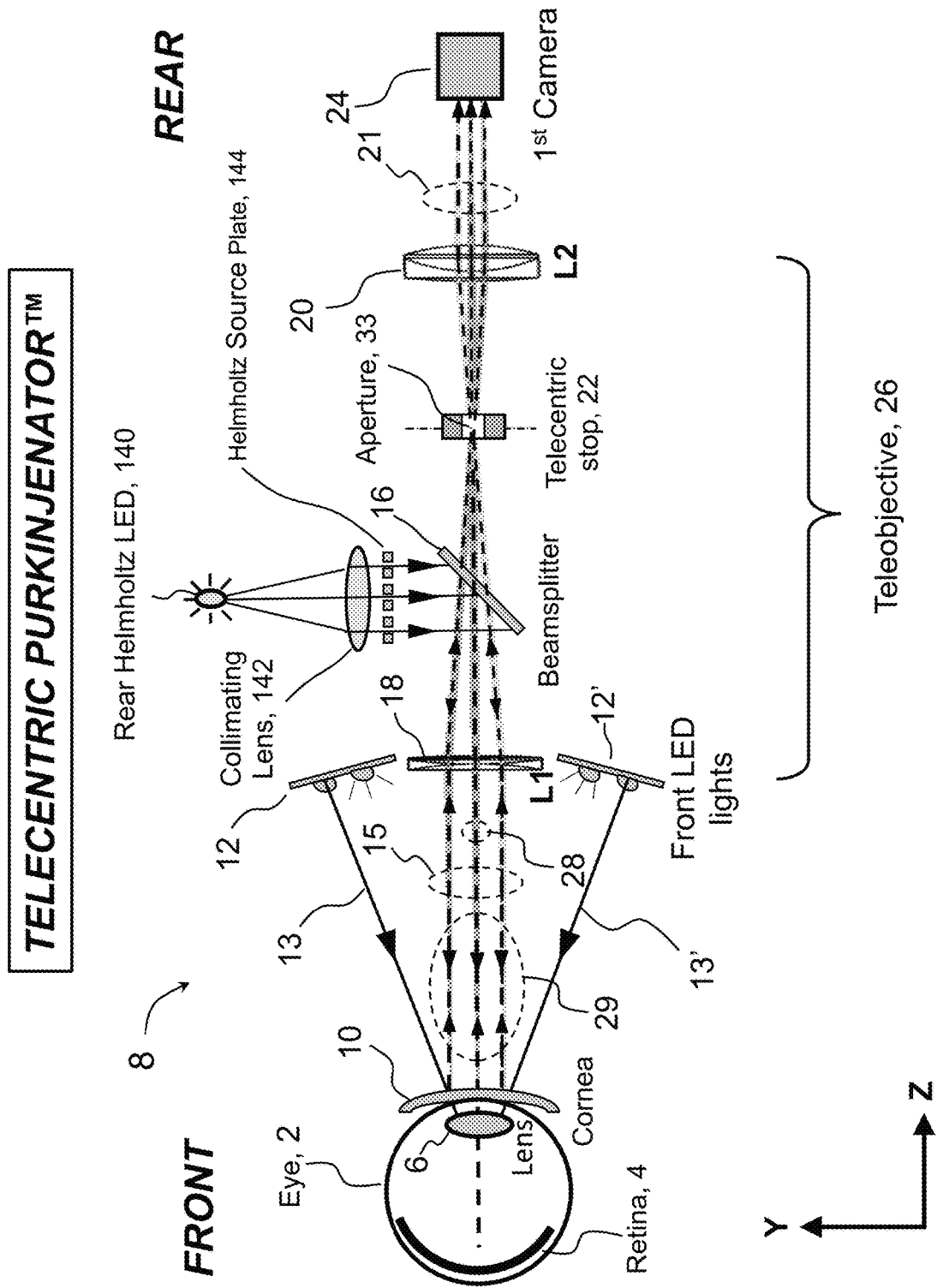
FIG. 32 shows a second embodiment of a schematic optical layout of a Purkinjenator™ eye-tracking device, according to the present invention.

FIG. 32 shows a second embodiment of a schematic optical layout of a Purkinjenator™ eye-tracking device, according to the present invention. In this version, the rear LEDs 14 are replaced with a Helmholtz LED Source 140. Light from source 140 is collimated by collimating lens 142, which then passes through a perforated Helmholtz aperture (source) plate 144 and on to beamsplitter 16, where it is re-directed through front lens 18 (L1) toward eye 2.

Figure 33:
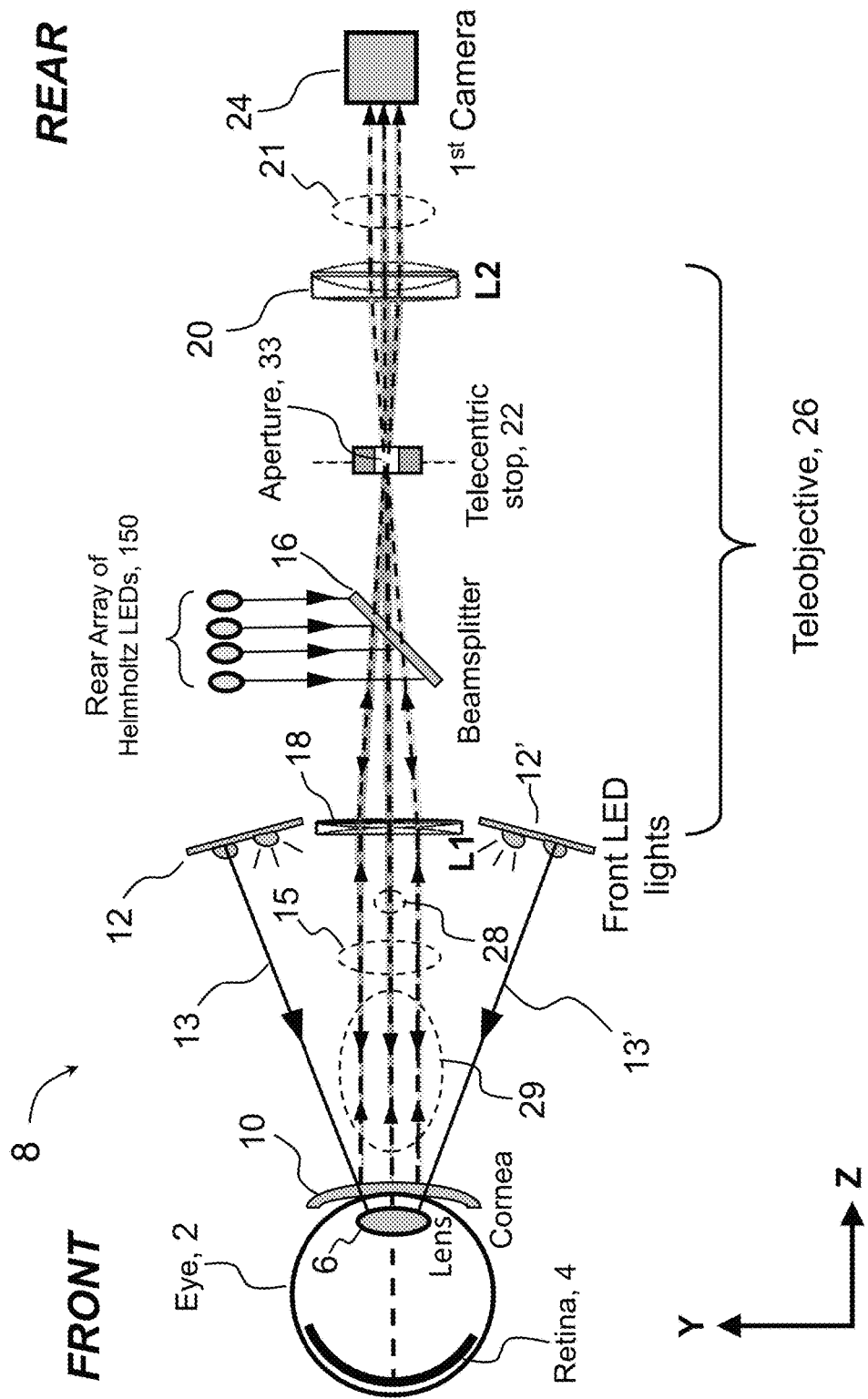
FIG. 33 shows a third embodiment of a schematic optical layout of a Purkinjenator™ eye-tracking device, according to the present invention.

FIG. 33 shows a third embodiment of a schematic optical layout of a Purkinjenator™ eye-tracking device, according to the present invention. In this embodiment, a linear array of rear Helmholtz LEDs 150 is located one focal length from the front objective lens 18 (thus, all rays are collimated in object space).

Figure 34A:
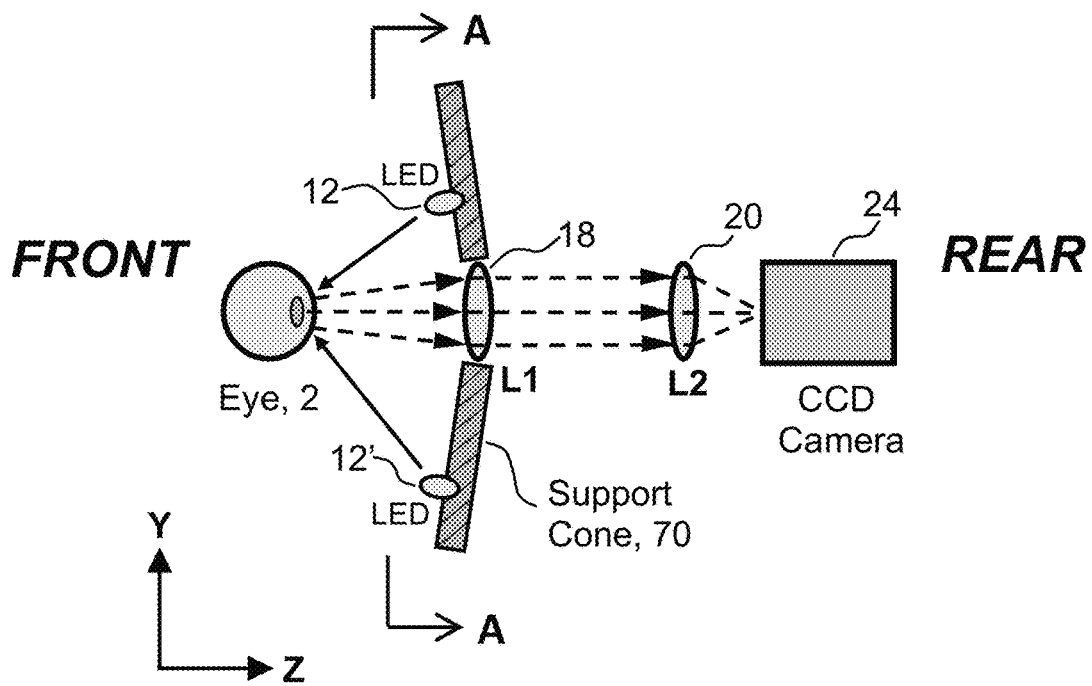
FIG. 34A shows a side elevation view of a fourth embodiment of a schematic optical layout of a Purkinjenator™ eye-tracking device, according to the present invention.

FIG. 34A shows a side elevation view of a fourth embodiment of a schematic optical layout of a Purkinjenator™ eye-tracking device, according to the present invention. Multiple Front LEDs are attached to a forward-facing support cone 70.

Figure 34B:
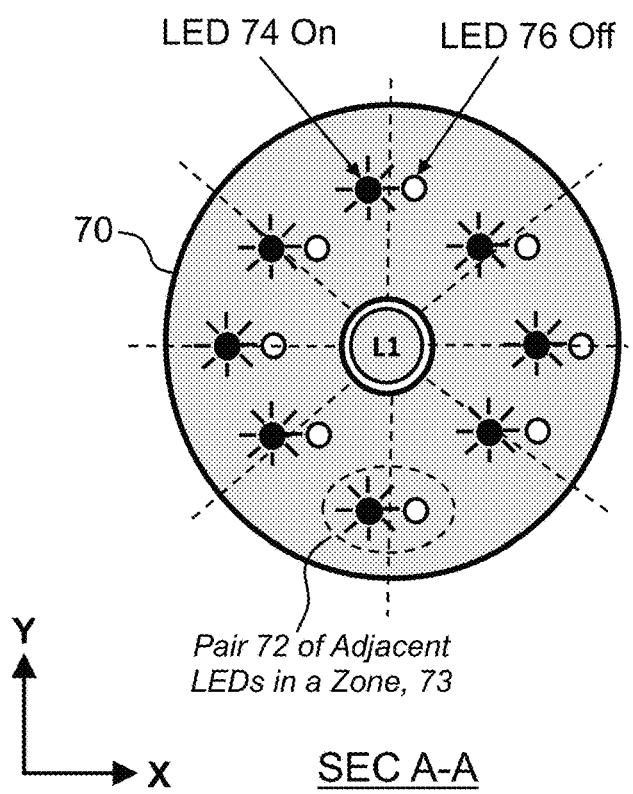
FIG. 34B shows a first example of a schematic layout of multiple pairs of adjacent LED light sources on a support cone, where each adjacent pair of LEDs in a Zone is arranged horizontally (side-by-side), and lying on a radial line originating from the origin of the support cone, according to the present invention.

FIG. 34B shows a first example of a schematic layout of multiple pairs 72 of adjacent LED light sources disposed on a support cone 70, where each adjacent pair of LEDs in a Zone 73 is arranged horizontally (side-by-side in the X-direction), and lays on a radial line originating from the origin of the support cone 70, according to the present invention. The eight radial lines are spaced apart 45 degrees in the circumferential direction. Since each LED can be individually addressed, some LEDs can be ON when some are OFF. In this example, LED 74 is turned ON, while closely-adjacent LED 76 is turned OFF.

Figure 35:
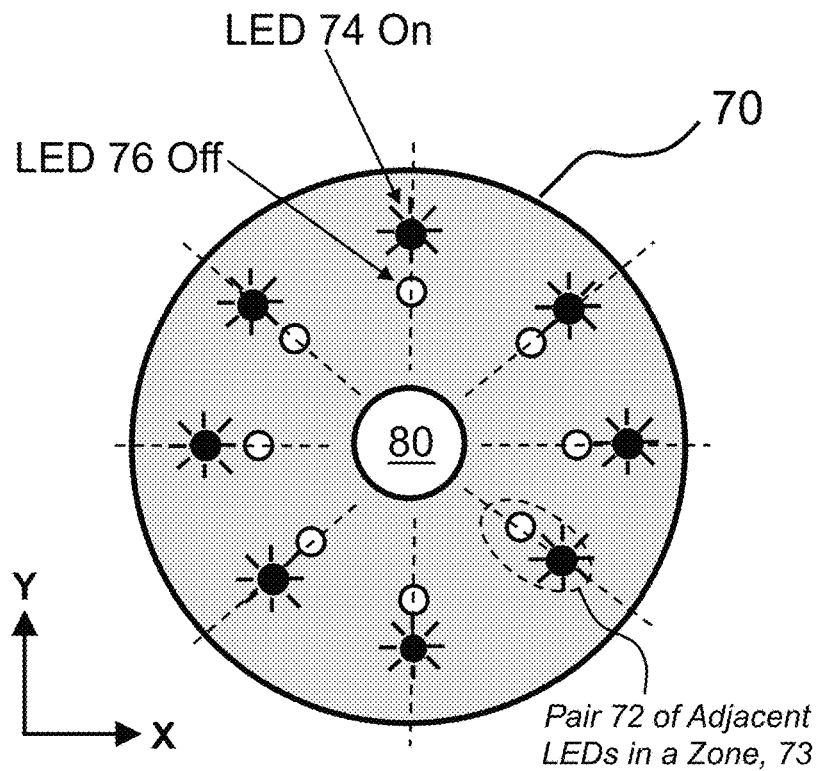
FIG. 35 shows a second example of a schematic layout of multiple pairs of adjacent LED light sources on a support cone, where each adjacent pair of LEDs in a Zone lays on a radial line originating from the origin of the support cone, according to the present invention.

FIG. 35 shows a second example of a schematic layout of multiple pairs of adjacent LED light sources on a support cone 70, where each adjacent pair 72 of LEDs in a Zone 73 lays on one of eight radial lines originating from the origin of the support cone 70, according to the present invention. In this example, LED 74 is turned ON, while closely-adjacent LED 76 is turned OFF. Aperture 80 is disposed in the center of support cone 70.

Figure 36:
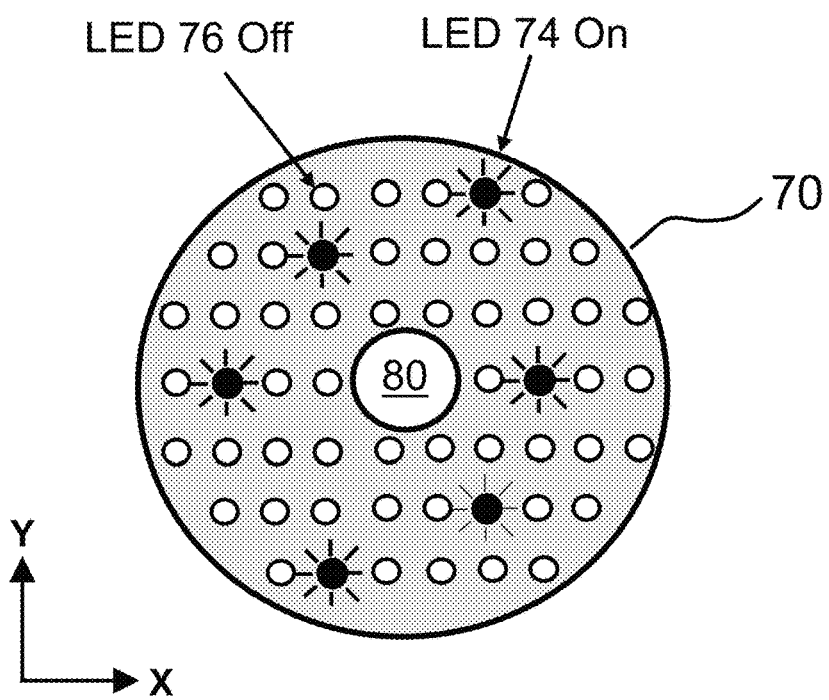
FIG. 36 shows a third example of a schematic layout of multiple LEDs arranged on a XY Cartesian grid on a support cone, where each LED is individually addressable.

FIG. 36 shows a third example of a schematic layout of multiple LEDs, arranged in a XY Cartesian grid on a support cone 70, where each LED is individually addressable. In this example, LED 74 is turned ON, while closely-adjacent LED 76 is turned OFF. Aperture 80 is disposed in the center of support cone 70.

Internal scatter of light emitted by a Helmholtz light source 31 (see FIG. 25) is high because the light from the LEDs is launched in all directions. Some of that light bounces around inside the optical device and becomes veiling glare on the CCD camera 24. As shown in FIG. 32, this problem can be eliminated by replacing the rear LEDs 14 with distinct bundles of semi-collimated rays. This can be done by using a single Helmholtz LED 140 located at a focal length distance away from a collimating lens 142, and then using an aperture plate (Helmholtz source plate 144) at the exit side of the lens 142. Then the spot pattern can be modulated using: a spatial light modulator (SLM) (see SLM 146 in FIG. 37), electrically addressable liquid cells (not shown), or by moving a blocking plate with a stepper motor (not shown).

Figure 37:
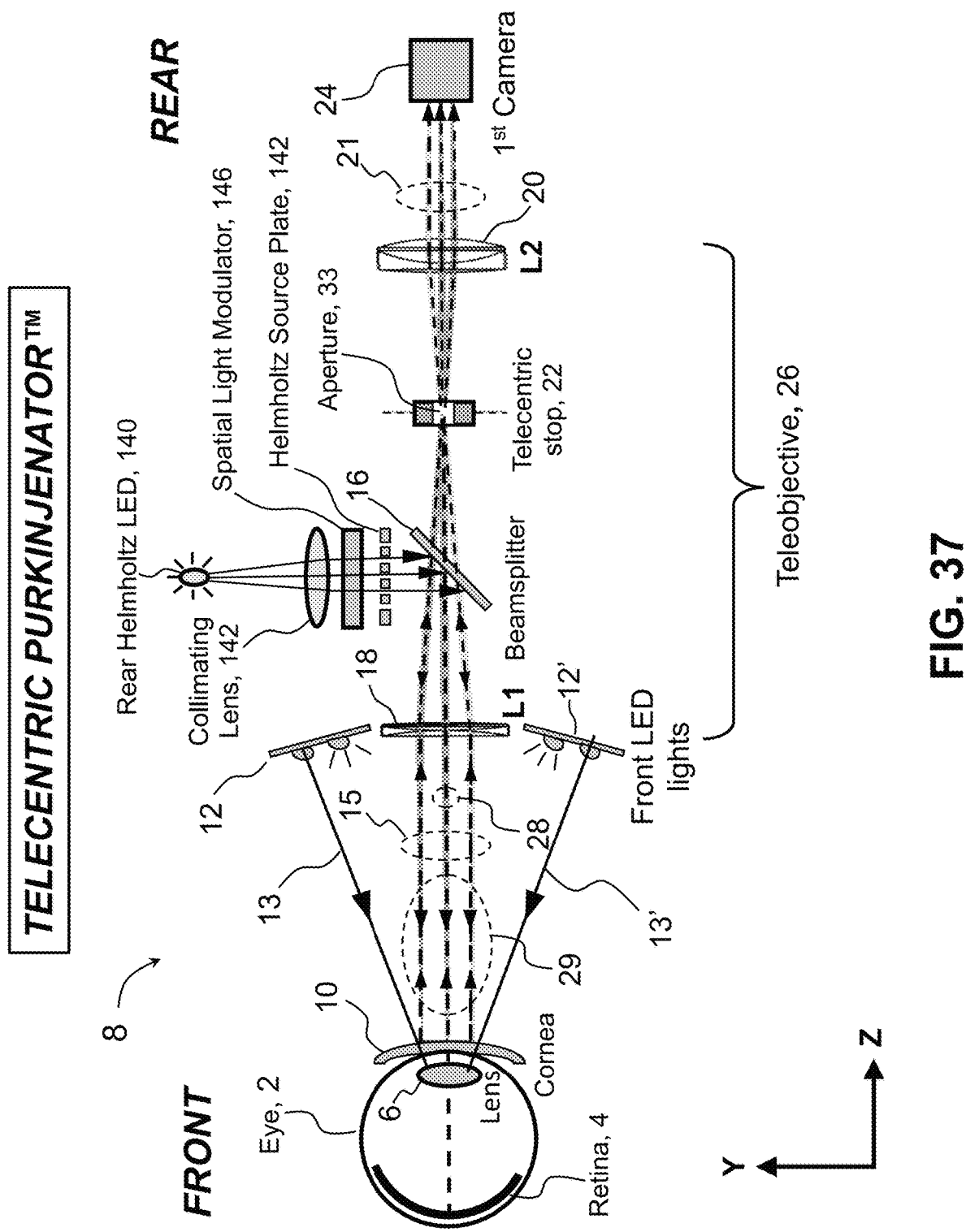
FIG. 37 shows a fifth embodiment of a schematic optical layout of a Purkinjenator™ eye-tracking device, according to the present invention.

FIG. 37 shows a fifth embodiment of a schematic optical layout of a Purkinjenator™ eye-tracking device, according to the present invention. Here, the rear LEDs 14 are replaced with distinct bundles of semi-collimated rays from a single Helmholtz LED 140. This can be done by using a single Helmholtz LED 140 located at a focal length distance away from a collimating lens 142, and then using an aperture plate (Helmholtz source plate 144) at the exit side of the lens 142. Then the spot pattern can be modulated using: a spatial light modulator (SLM) 146, electrically addressable liquid cells (not shown), or by moving a blocking plate with a stepper motor (not shown).

Figure 40:
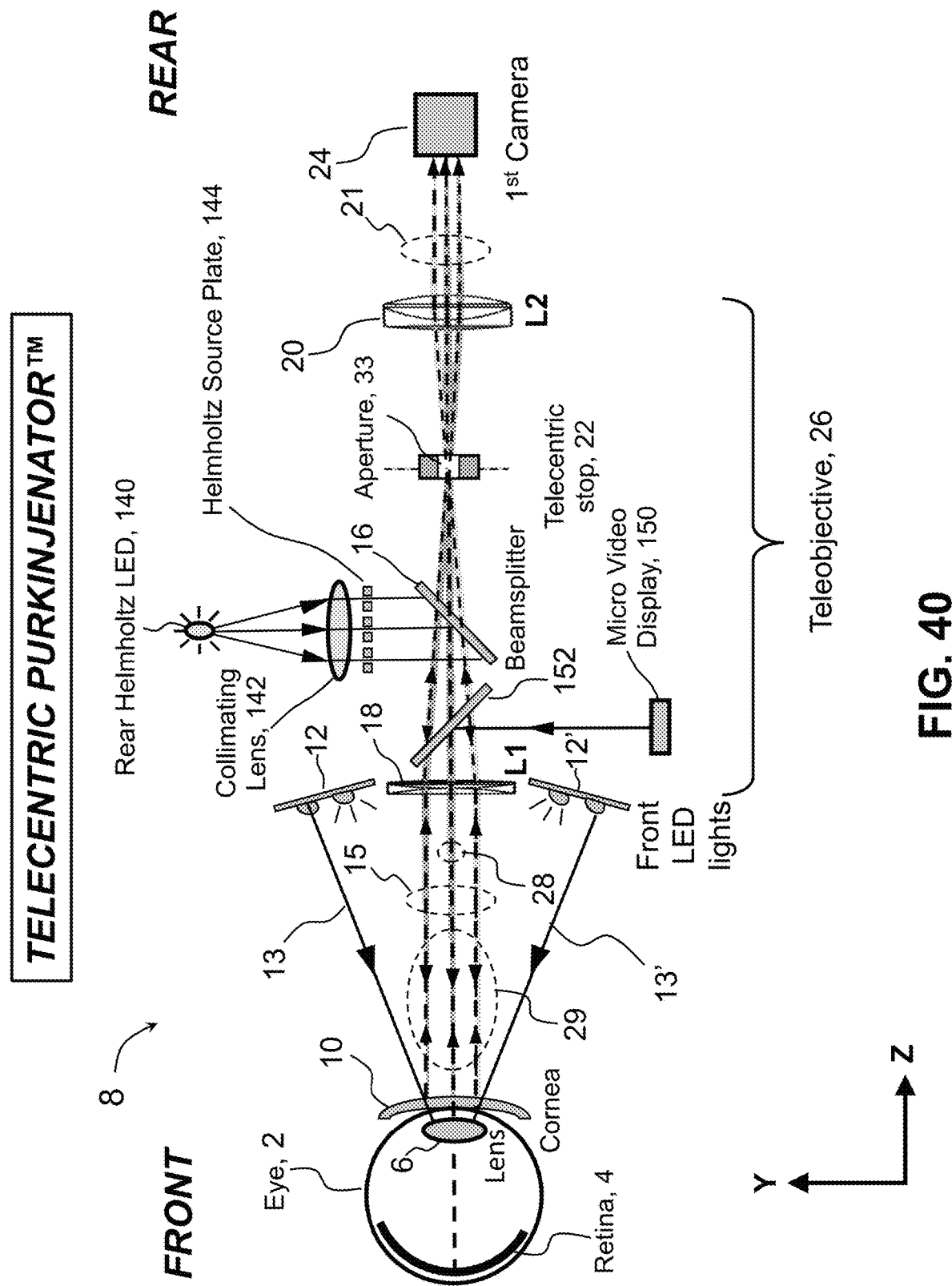
FIG. 40 shows an eighth embodiment of a schematic optical layout of a Purkinjenator™ eye-tracking device, according to the present invention.

In most of these embodiments, the front (and rear) array of point light sources that illuminate the eye are LEDs, which can be individually activated (addressable). Alternatively, as shown in FIG. 40, the front array of light sources can comprise a Micro Video Display (MVD) 150 (e.g., mini-computer screen, micro-display, or pico-projector with LED or LCD display pixels), with a continuously-ON display [11]. These components can be used for replacing a Helmholtz source 31, or, instead, for replacing the front LEDs 12, 12'. An advantage of the mini/micro display is an extremely high number of patterns can be rapidly generated and easily controlled in a small enclosure.

Figure 26:
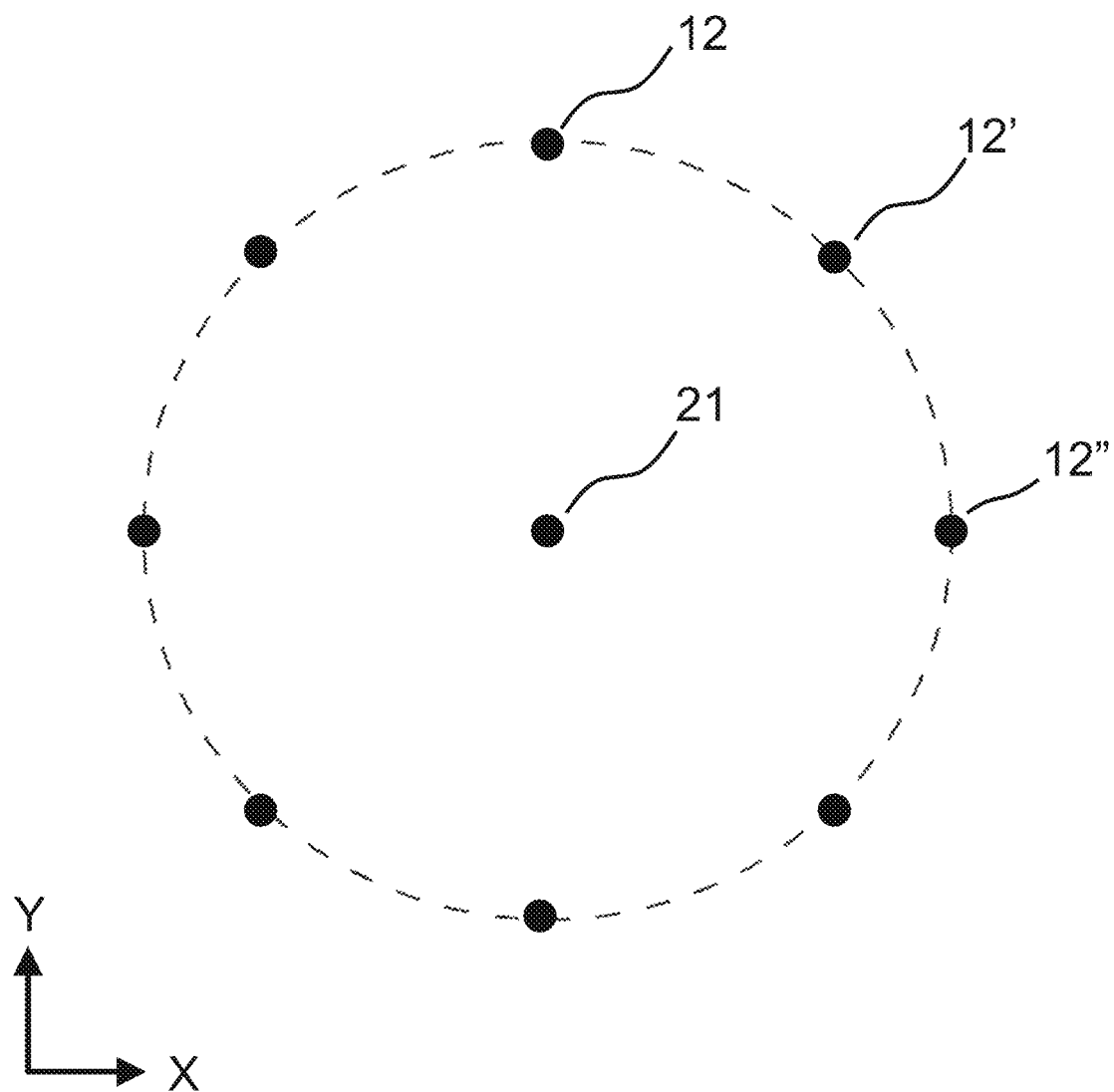
FIG. 26 shows an elevation view of an example of a front set of LED light sources that comprises eight external LEDs arranged uniformly around a circle, with a ninth LED light source located at the origin of the circle, according to the present invention.

FIG. 26 shows an example of a front set of LED sources 12, 12' that comprises eight external LEDs 12, 12', etc. arranged uniformly around a circle, with a ninth LED 21 located at the origin of the circle.

Another option is to discriminate images by their color using a color CCD camera 24. Some LEDs are green. Some are red. Some are infrared. On most color cameras, if the infrared cutoff filter is removed, deeply infrared LEDs (900 to 1100 nm) light up pixels equally brightly because of the nearly equal infrared transmission of the red, green and blue dyes in a color filter array. For some color cameras, with particular color filter arrays, it is possible to distinguish LEDs that are 700, 750 or 800 nm. In all cases, infrared LEDs are also distinguishable from Red, Green or Blue LEDs. Even in the presence of overlap, it is possible to discriminate reflections when they have different colors.

An ideal eye-tracking system would be adaptively programmed. During a first scan pattern after applanation, LEDs that create overlaps of Purkinje images would be identified. Then, on subsequent scans, those problematic LEDS would be omitted (manually, or automatically). Also, two LEDs that produce spots that are well-separated could be lit up together. Ideally, the system would identify a minimum number of LEDs that would enable accurate position and tip/tilt tracking. Once determined, the reduced set would enable faster real-time control.

The main optical path in FIG. 24 is drawn as being telecentric using two lenses (L1 and L2) in the imaging path 28. An alternate embodiment can be non-telecentric in the imaging path, and can use a single lens in the imaging path. In that case, a Helmholtz source could still be inserted using a beam splitter. In that situation, the lens that collimates the beam from the Helmholtz source will be out of the main optical path.

Figure 38:
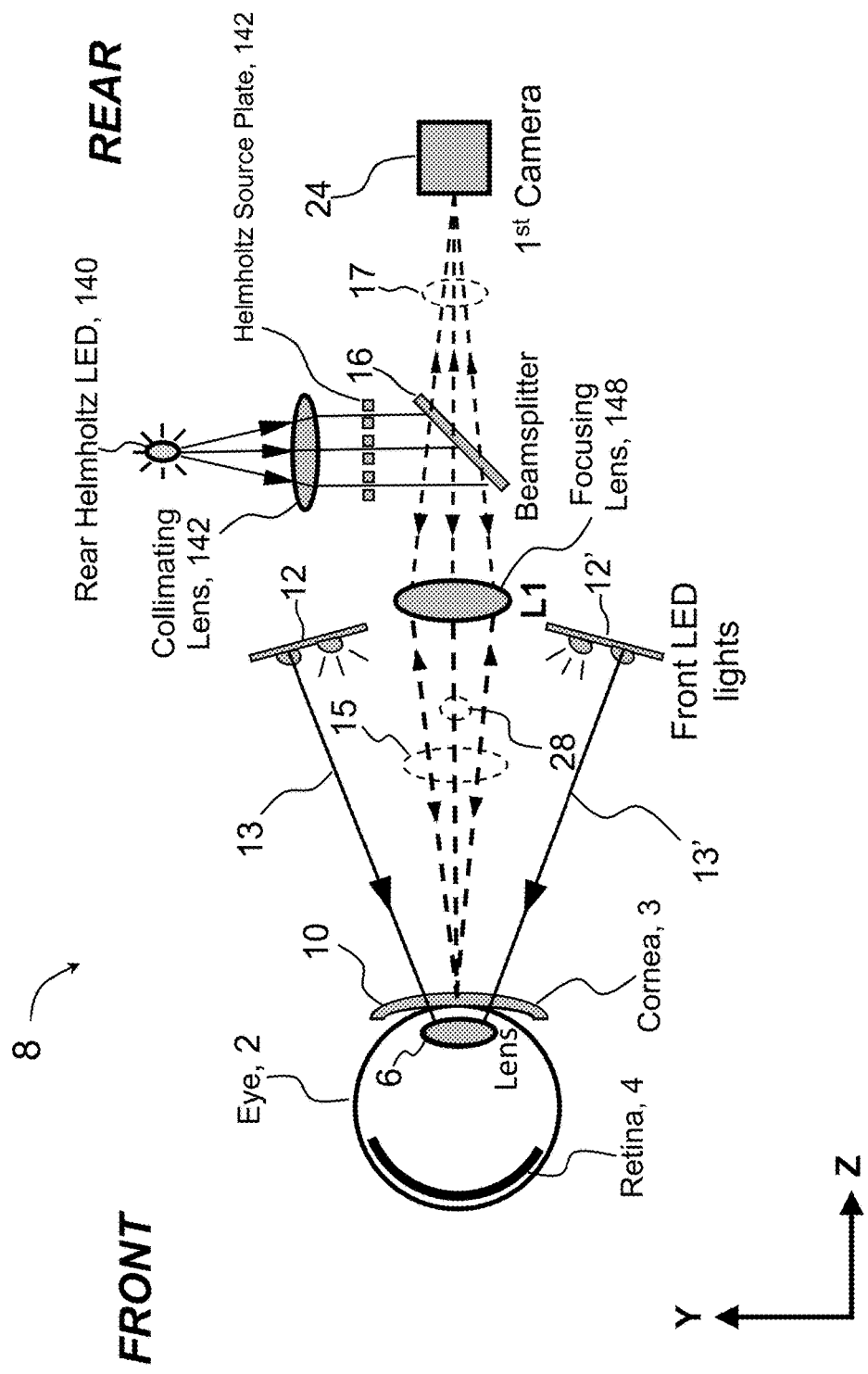
FIG. 38 shows a sixth embodiment of a schematic optical layout of a Purkinjenator™ eye-tracking device, according to the present invention.

FIG. 38 shows a sixth embodiment of a schematic optical layout of a Purkinjenator™ eye-tracking device, according to the present invention. In this embodiment, the rear lens 20 (L2) has been removed (which makes the optical layout non-telecentric). Light from the rear Helmholtz LED 140 passes through a collimating lens 142 and then through a perforated Helmholtz aperture plate 142 (source plate 142), and then on to beamsplitter 16, where the light is directed towards the eye 2 via lens 18 (L1). CCD camera 24 is located at one focal length from the front lens L1. In this setup, beamsplitter 16 is located in-between front lens L1 and rear CCD camera 24.

Figure 39:
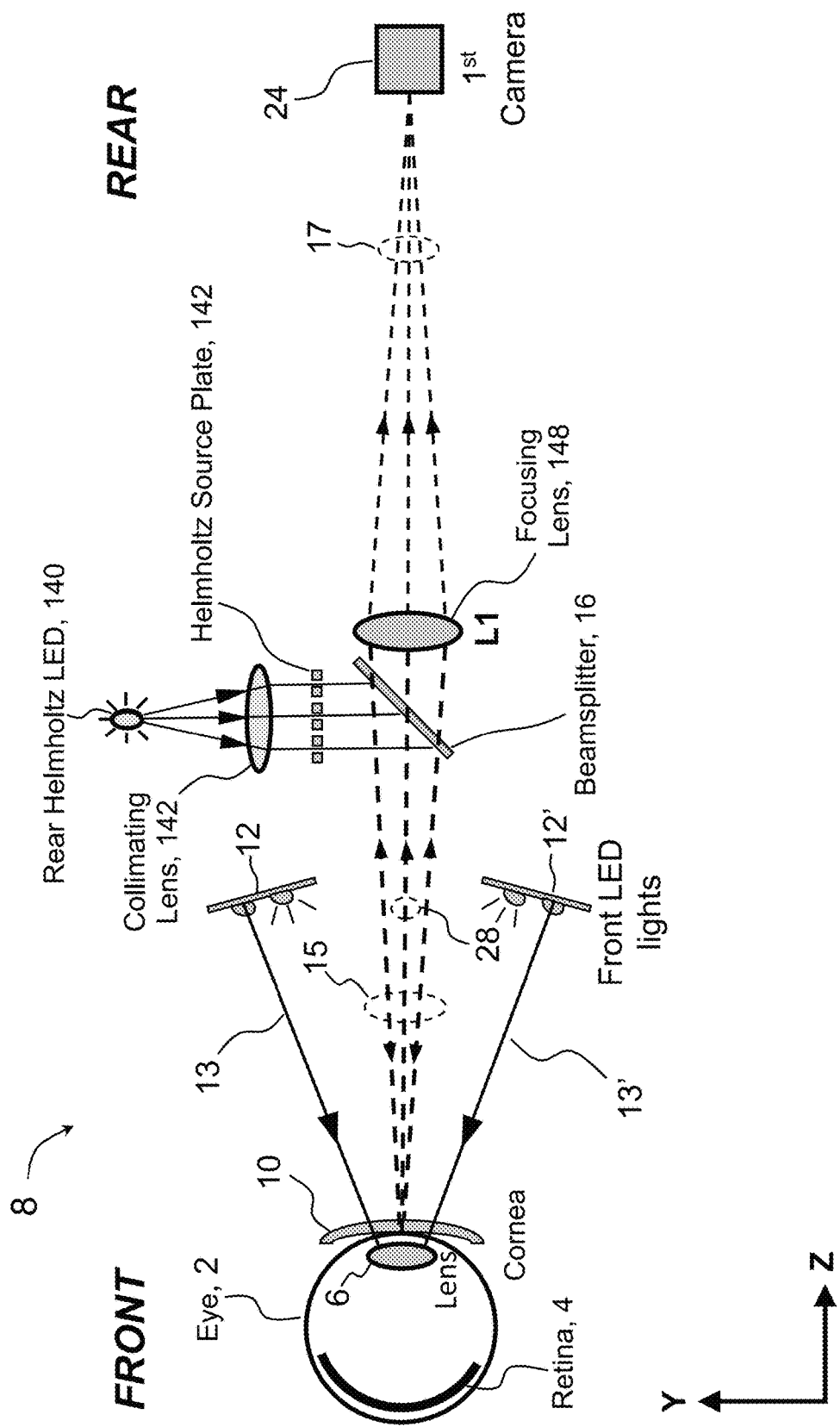
FIG. 39 shows a seventh embodiment of a schematic optical layout of a Purkinjenator™ eye-tracking device, according to the present invention.

FIG. 39 shows a seventh embodiment of a schematic optical layout of a Purkinjenator™ eye-tracking device, according to the present invention. In this embodiment, the rear lens 20 (L2) has been removed (which makes the optical layout non-telecentric). Light from the rear Helmholtz LED 140 passes through a collimating lens 142 and then through a perforated Helmholtz aperture plate 142 (source plate 142), and then on to beamplitter 16, where the light is passes directly towards eye 2 (i.e., without passing through lens L1). CCD camera 24 is located at one focal length from the lens L1. In this embodiment, beamsplitter 16 is located in-between lens L1 and Eye 2 (which is different that the embodiment shown in FIG. 38).

FIG. 40 shows an eighth embodiment of a schematic optical layout of a Purkinjenator™ eye-tracking device, according to the present invention. If the person changes their gaze angle into the instrument, the reflected pattern of external light sources will also shift. Analysis of the shifted patterns can be done to determine internal eye structures. A video-based fixation target 150 can be included in the optical system 8 to direct the patient's gaze, where the flashing of the fixation target 150 is synchronized with the CCD camera 24 and the data collection system (not shown). The patient views a micro-display 150, typical with about an 0.5 inch diagonal length of the screen, through front lens 18 (L1), which serves as a magnifying glass. Such an arrangement is common in instruments like autorefractors and aberrometers, or in clinical practice.

Figure 41:
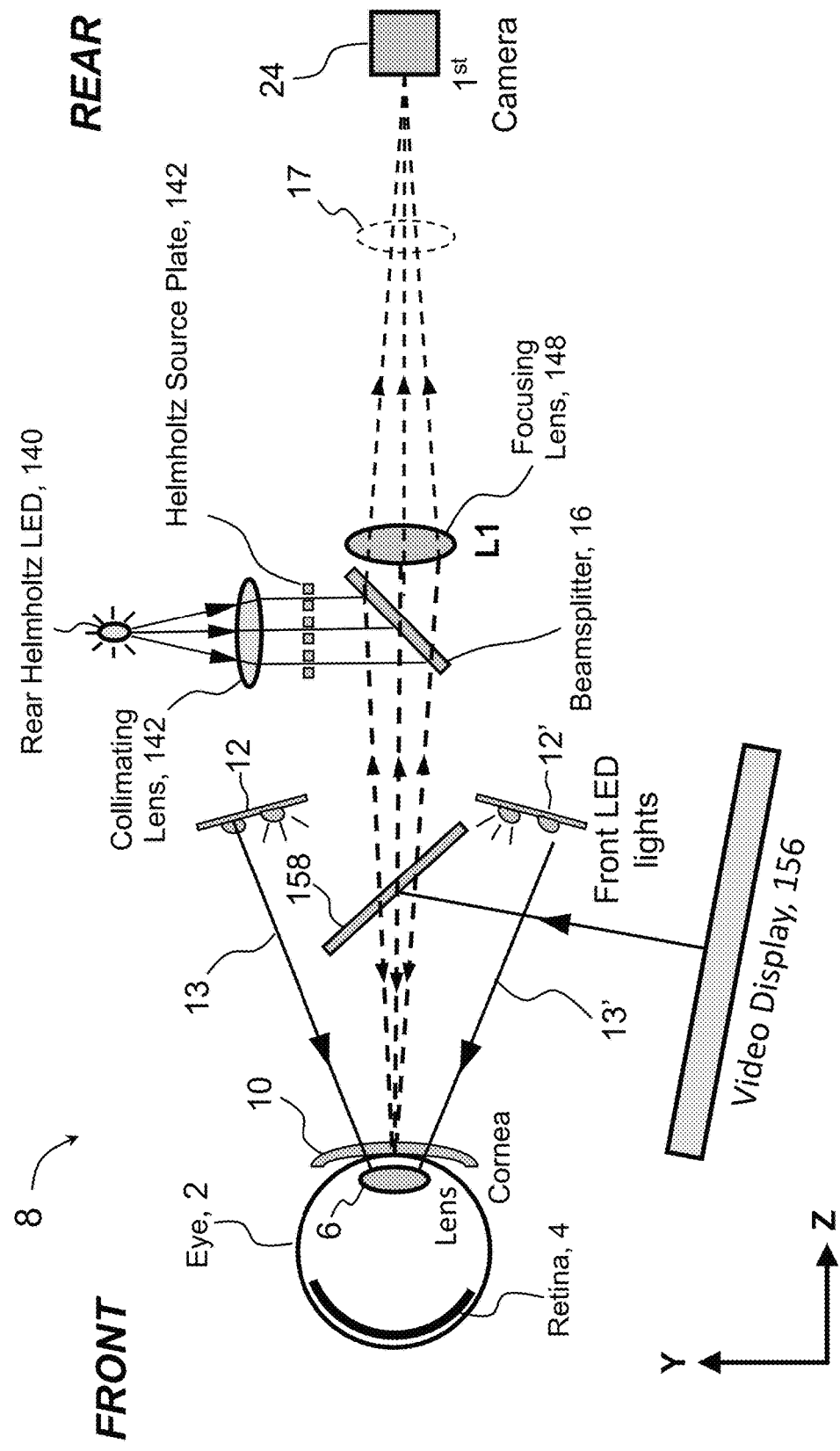
FIG. 41 shows a ninth embodiment of a schematic optical layout of a Purkinjenator™ eye-tracking device, according to the present invention.

FIG. 41 shows a ninth embodiment of a schematic optical layout of a Purkinjenator™ eye-tracking device, according to the present invention. The embodiment shown in FIG. 41 is similar to FIG. 39, with the exception being the addition of a video display monitor 156 that is oriented to shine a light pattern or image onto a second (front) beamsplitter 158, which reflects the incoming light from monitor 156 directly to eye 2 (i.e., without any intervening optical elements). The display can be a normal computer monitor, typically with a 15-inch diagonal screen.

In some embodiments of using a Purkinjenator™ device, the eye may be held nearly stationary by an applanation suction ring. Unfortunately, such systems use thin fluid layers that greatly reduce the strength of the first Purkinje reflections off the cornea and the effect of light-bending by the cornea. In this case, the front LED light source pattern 12, 12' can be modified with different spacing between LEDs and/or different brightness of the LEDs according to if an applanated or non-applanated eye is being measured.

Some novel aspects of the Purkinjenator™ optical system include, among other things:

(1) synchronizing the LED illumination with the CCD camera so that only one LED is imaged at a time; and
(2) projecting a pattern through a lens in the device to compute Z-motion of an IOL or natural lens.
(3) arranging the LED illumination pattern so there are distinct zones where pairs of LEDs are located, and on subsequent frames, only one of the LED in each pair is lit up so spot motion algorithms can be used to differentiate $P_3$ and $P_4$ images on sequential and synchronized images;
(4) simultaneously turning on LEDS in different zones when they are separated far enough apart so there is no chance of Purkinje image overlap;
(5) using LED brightness that place natural lens or IOL Purkinje spots ($P_3$, $P_4$) in the mid-sensitivity range of the camera, while leaving the corneal reflection ($P_1$, $P_2$) saturated on the camera so reflections from the cornea can be differentiated from those from the natural lens or an IOL (the software optionally could adjust the LED brightness to optimize the image); and
(6) turning ON a single LED at the start of a data acquisition sequence and analyzing the results to decide what is the most efficient pattern of illuminations to use during the subsequent sequential image captures.

Figure 42:
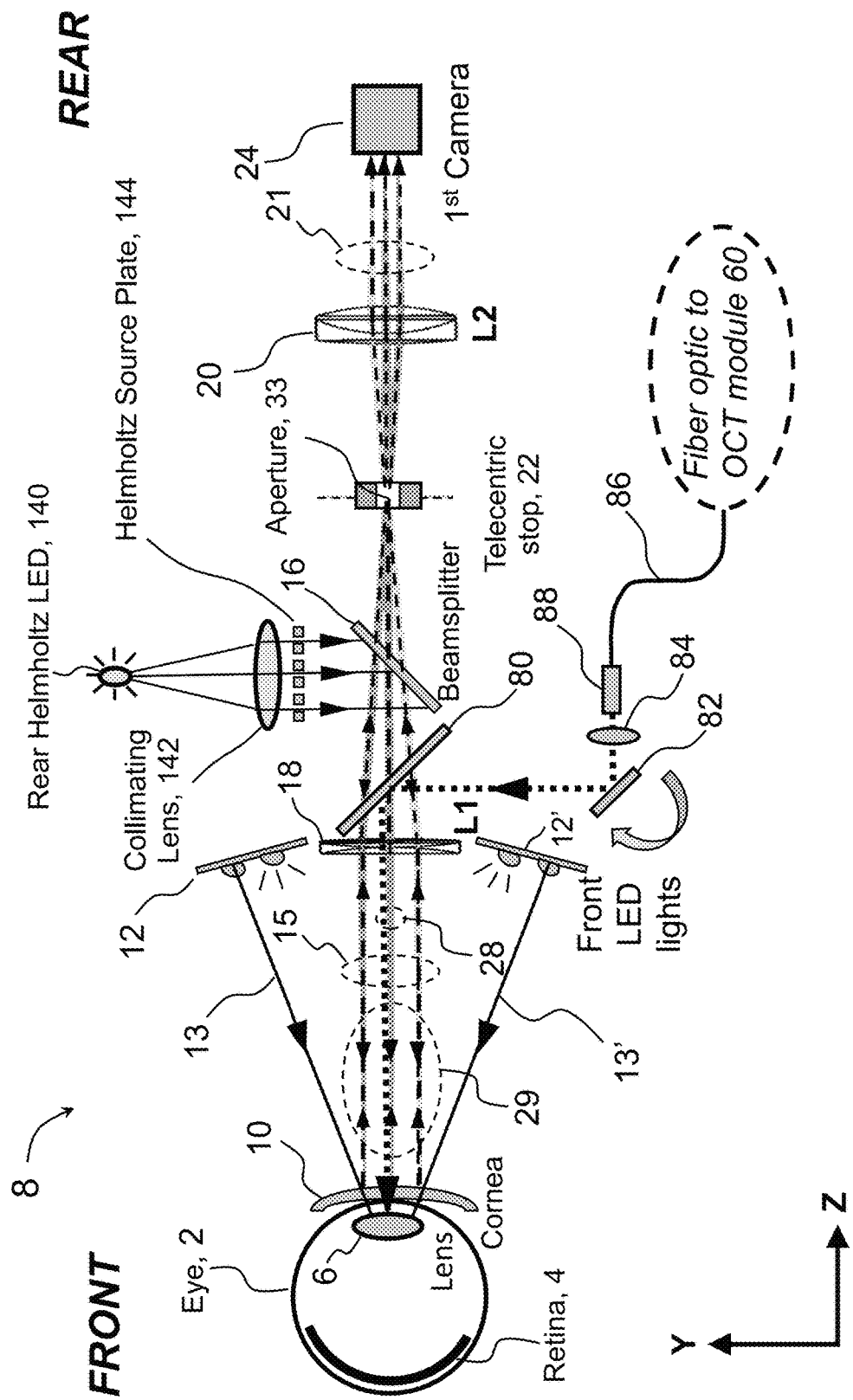
FIG. 42 shows a tenth embodiment of a schematic optical layout of a Purkinjenator™ eye-tracking device coupled to an OCT module, according to the present invention.

FIG. 42 shows a tenth embodiment of a schematic optical layout of a Purkinjenator™ eye-tracking device coupled to an OCT module, according to the present invention. This embodiment is similar to that shown in FIG. 32, with the exception being the addition of fiber optic 86 that is coupled to an adjacent OCT module 60 (not shown). Note: see FIG. 29 for a detailed schematic layout of a breadboarded OCT system 60. The distal end of fiber optic 86 in FIG. 42 connects to fiber optic cable 94 in FIG. 29 (which goes to sample 40). In FIG. 42, swept-wavelength laser light 30 from the OCT module 60 passes through a small collimating lens L3 and then onto a scanning mirror 82, which is nominally set at 45 degrees, but can scan+/−10 degrees, for example.

Figure 43:
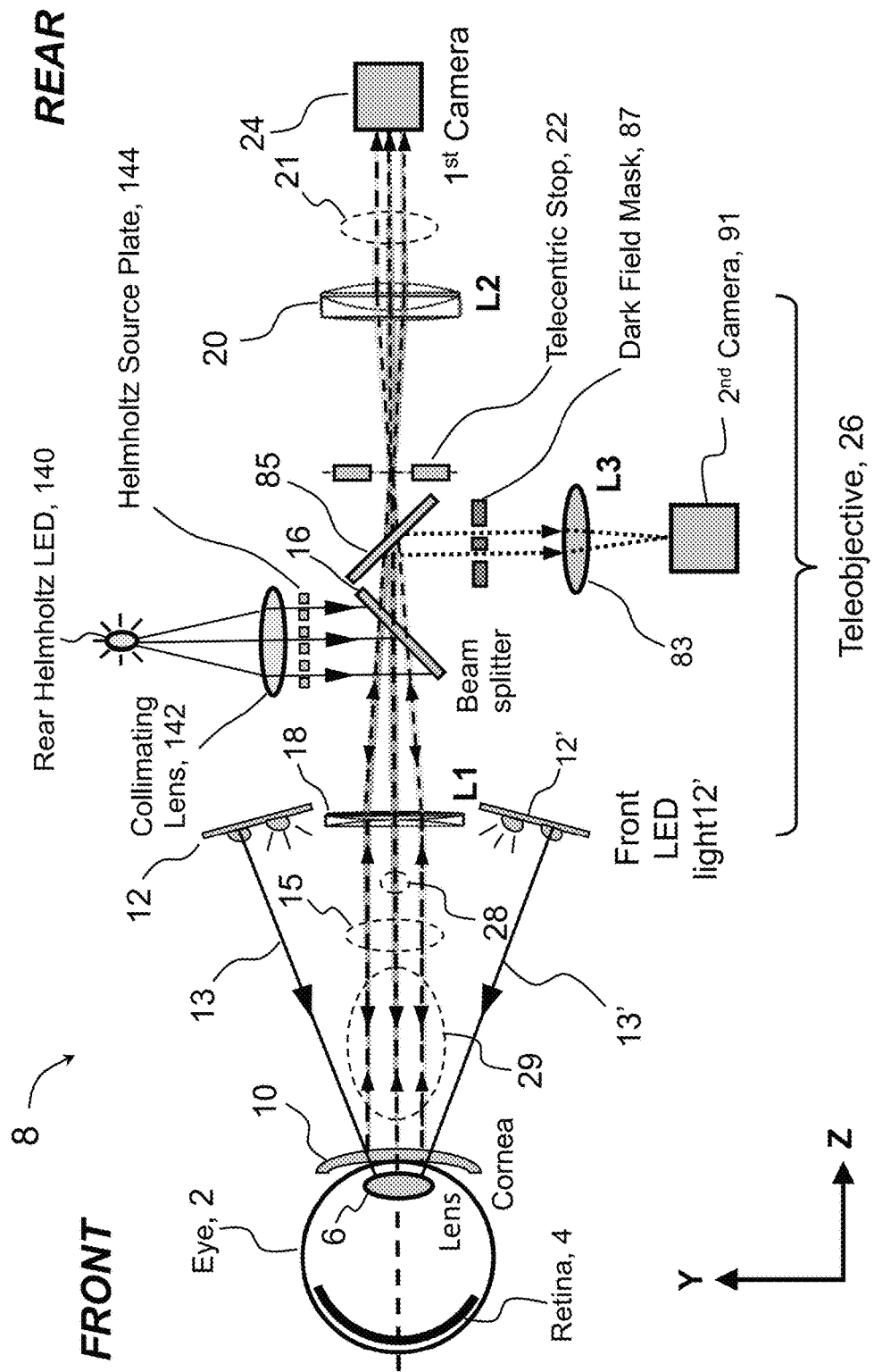
FIG. 43 shows an eleventh embodiment of a schematic optical layout of a Purkinjenator™ eye-tracking device coupled to an OCT module, according to the present invention.

FIG. 43 shows an eleventh embodiment of a schematic optical layout of a Purkinjenator™ eye-tracking device coupled to an OCT module, according to the present invention. Light emitted from eye 2 (i.e., Purkinje images) reflects off of beamsplitter mirror 85 and then passes through Dark Field mask 87, then through lens 83, which focuses the light onto a second camera 91.

Figure 44:
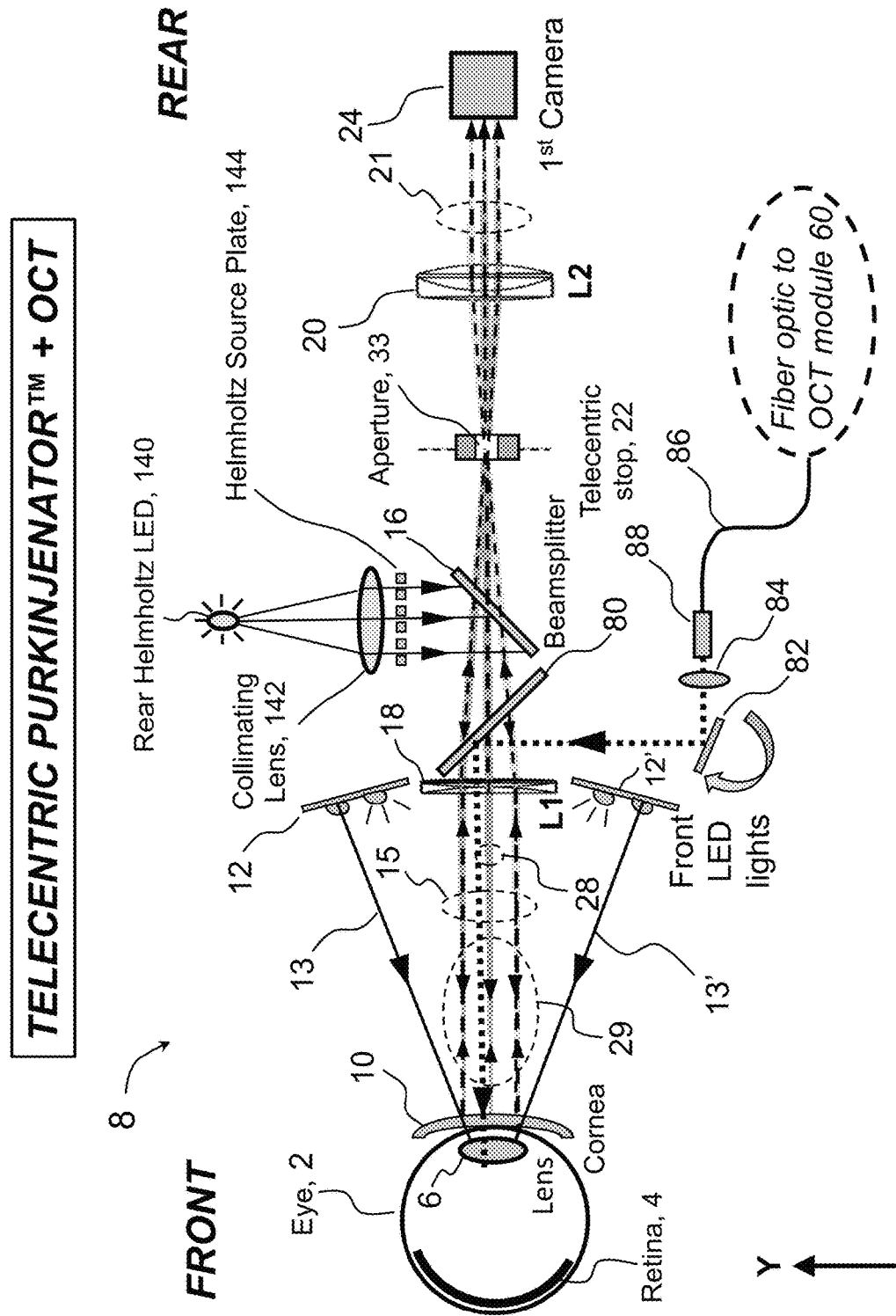
FIG. 44 shows the tenth embodiment of a schematic optical layout of a Purkinjenator™ eye-tracking device coupled to an OCT module, according to the present invention.

FIG. 44 shows the tenth embodiment shown previously of a schematic optical layout of a Purkinjenator™ eye-tracking device coupled to an OCT module, according to the present invention. Here, the scanning mirror 82 has been set at a smaller angle, for example, 43 degrees (instead of 45 degrees). This mirror rotation of 2 degrees (0.0035 radians), coupled with a focal length of 86 mm for front lens L1, produces an X-axis shift distance=3 mm for the point at which the laser spot impinges on the cornea 3 of eye 2.

Figure 31:
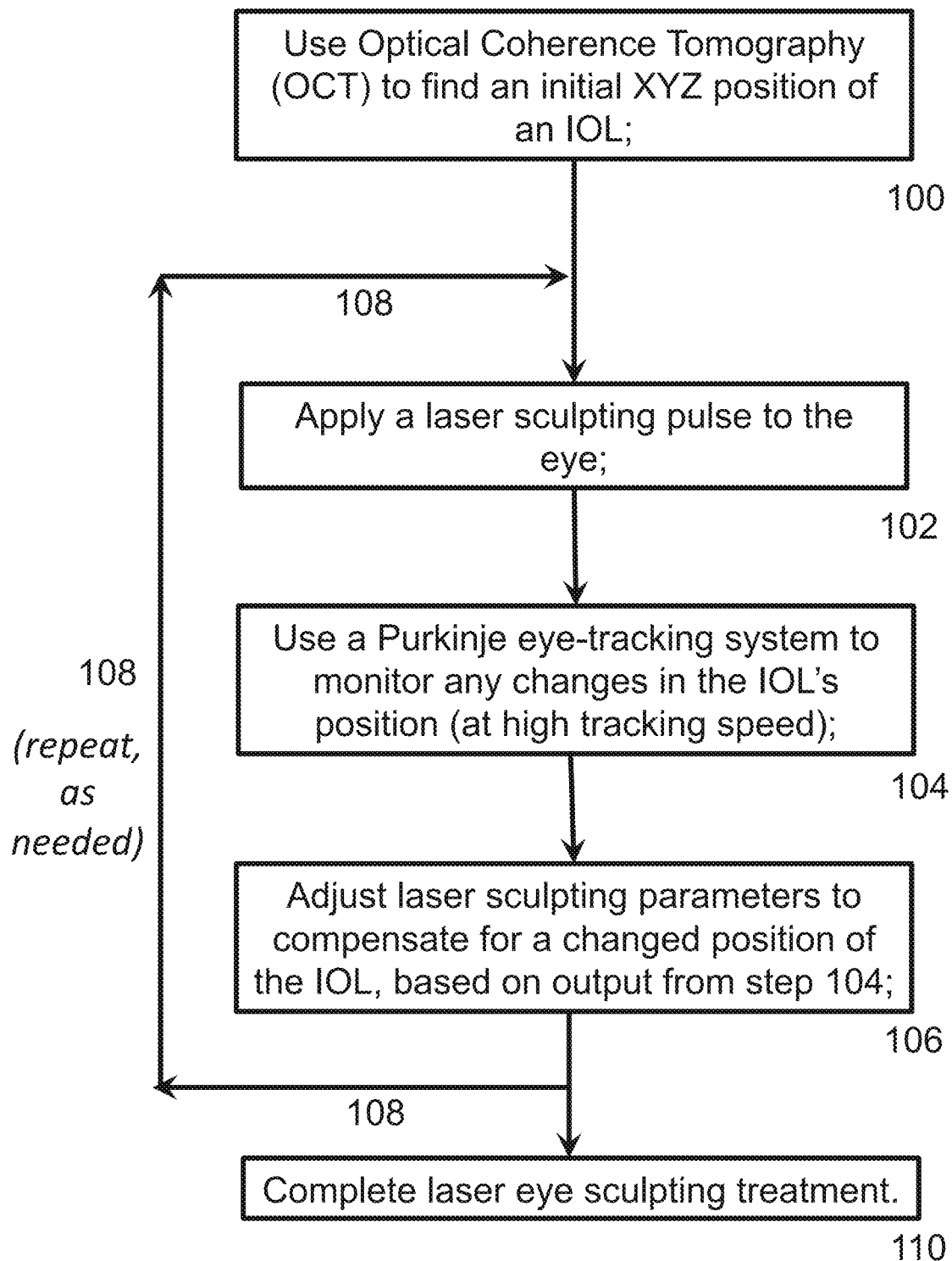
FIG. 31 show a process flow chart of steps for doing laser eye sculpting using a system comprising an OCT optical system combined with a Purkinjenator™ optical device, according to the present invention.

Before a laser sculpting treatment begins (e.g., LASIK), the OCT system would initially take several seconds to find the precise initial XYZ position of an IOL. Then the OCT system would be turned off, and the Purkinje tracking system would take over and be used to monitor changes in IOL position at high tracking speed (essentially, in real-time) during the laser sculpting treatment. FIG. 31 shows the steps used for this example of a preferred method of operation.

Figure 27:
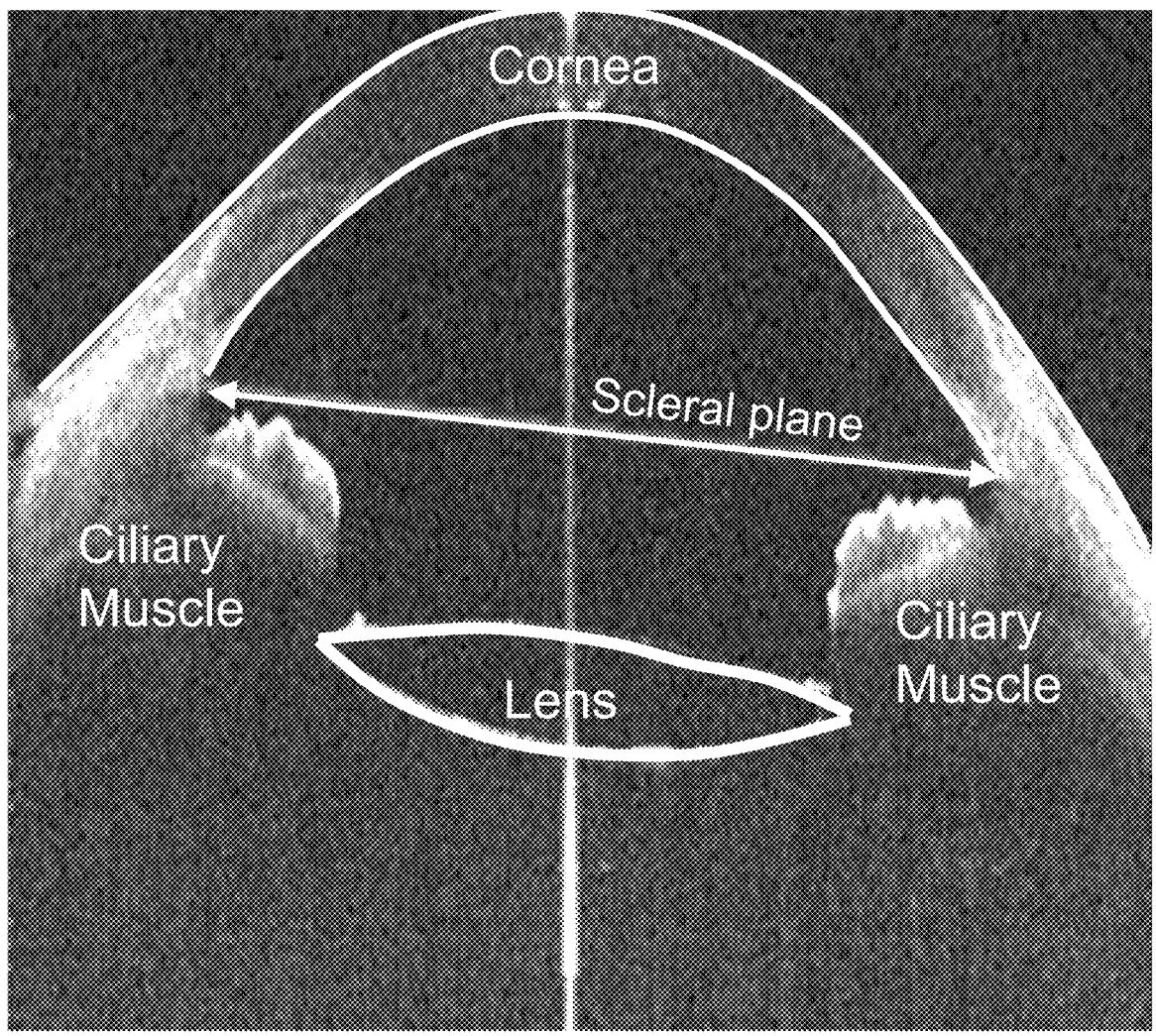
FIG. 27 shows a photograph of an OCT image of a cross-section view of an eye, highlighting the cornea and lens structures, along with the ciliary muscles, according to Xin et al. [65].
Figure 28:
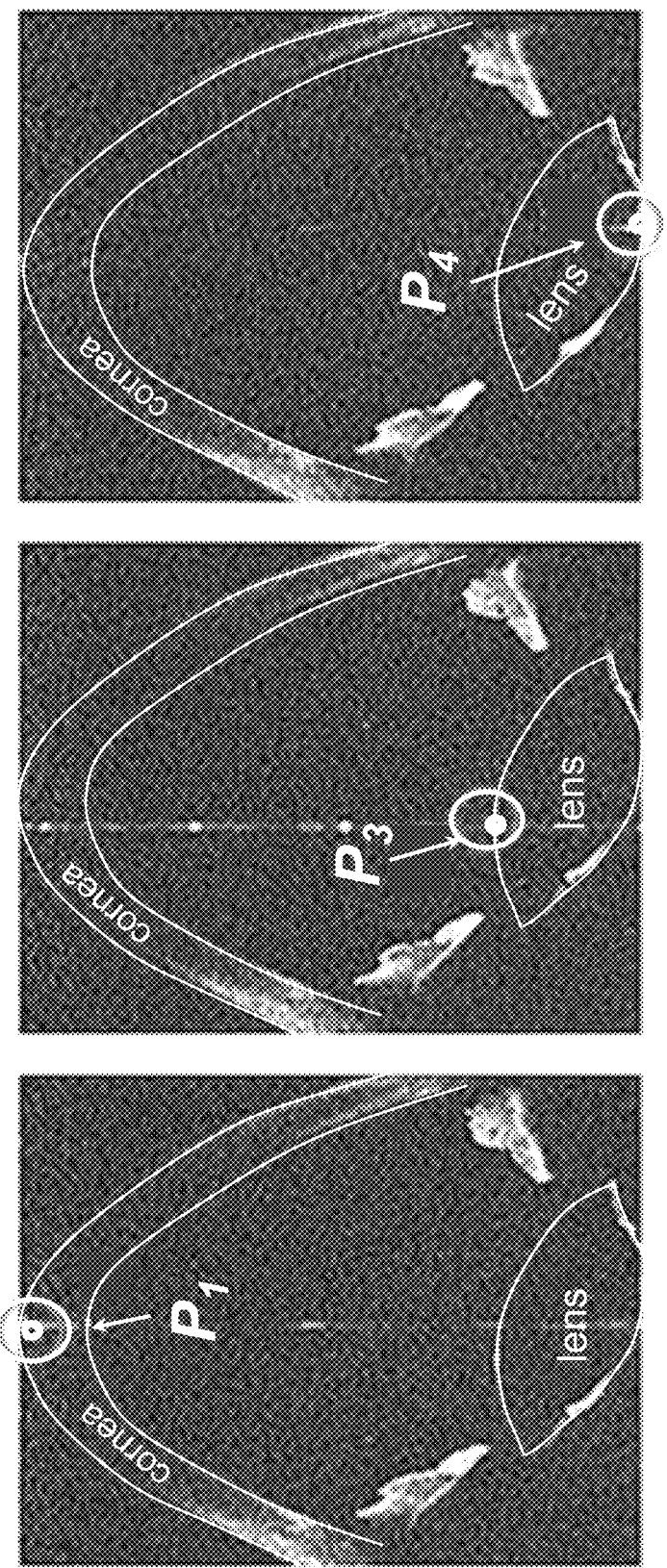
FIG. 28A shows a photograph of an OCT image of a cross-section view of an eye, where we can see an example of $P_1$, the first Purkinje image, originating from the front surface of the cornea, according to Sun et al [17].
FIG. 28B shows a photograph of an OCT image of a cross-section view of an eye, where we can see an example of $P_3$, the third Purkinje image, originating from the front surface of the lens, according to Sun et al [17].
FIG. 28C shows a photograph of an OCT image of a cross-section view of an eye, where we can see an example of $P_4$, the fourth Purkinje image, originating from the rear surface of the lens according to Sun et al [17].

An example of the results from an OCT analysis made by Xin et al. [65] is shown in FIG. 27, which illustrates a cross-section view of the lens, cornea, and ciliary muscles that shape the lens (while still being soft and elastic). The scleral shelf is also shown. In FIGS. 28A, 28B, and 28C we can see examples of $P_1$, $P_3$, and $P_4$ types of Purkinje images, respectively. In this embodiment, the OCT specular reflection from each surface is used to locate and align an IOL. This allows one to calculate the Z-axis position accurately and in real-time. This method may result in lower processing requirements than performing a full 3D OCT analysis.

Figure 29:
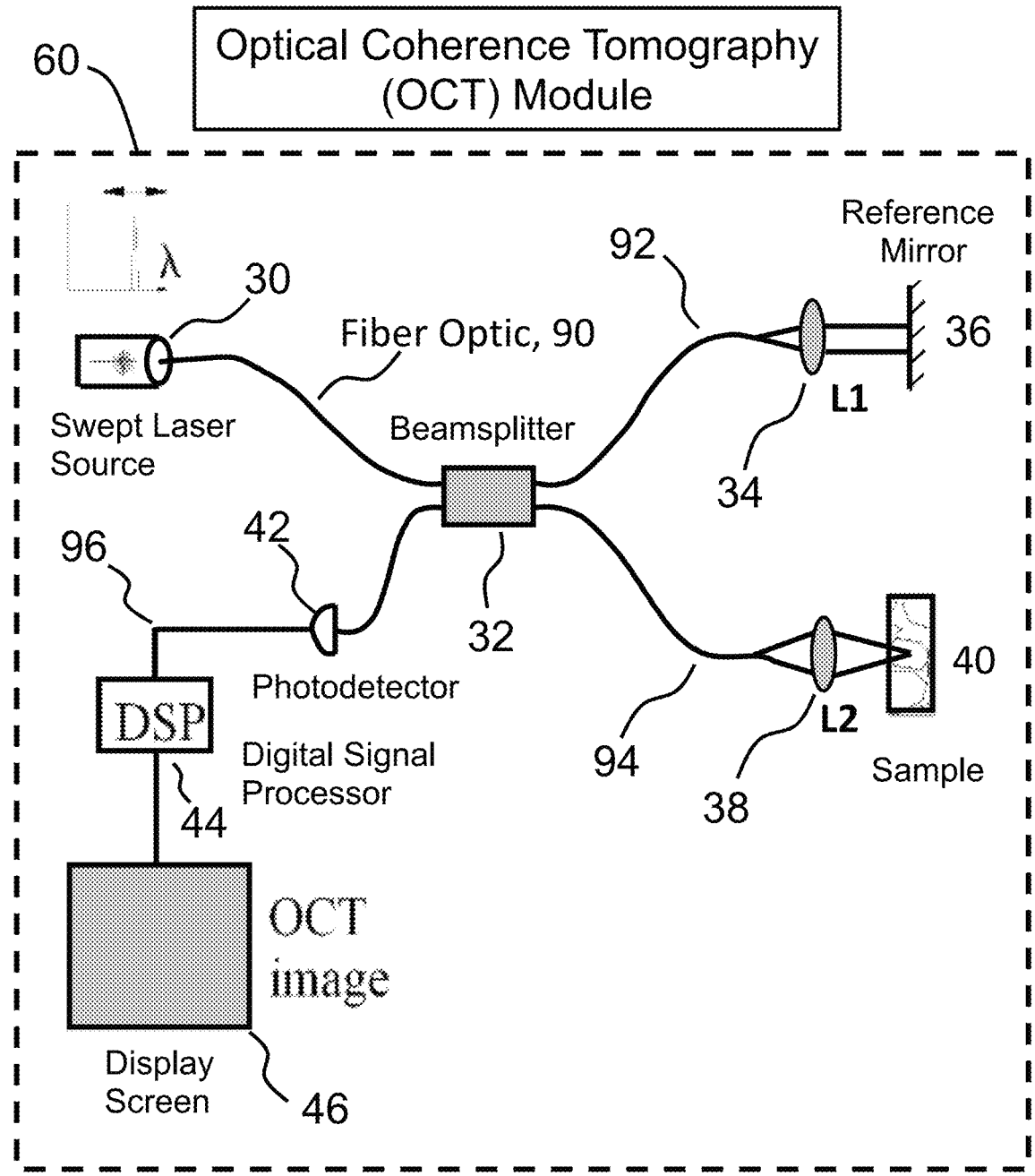
FIG. 29 shows a schematic view of a prototype OCT optical system, that can be breadboarded using off-the-shelf components, according to the present invention.

A prototype stand-alone OCT system, such as the schematic example shown in FIG. 29, can be breadboarded using off-the-shelf components. The breadboard setup 60 can consist of a swept laser source 30 with X-Y scanning and high-speed data acquisition. The breadboard 60 can be used to verify the required signal to noise needed to detect IOLs reliably and to verify the required optical power and detection efficiency. It will also allow testing of various scan profiles and IOL detection algorithms. The acronyms used in FIG. 29 stand for the following: SS is a swept source 30, referring to a laser that scans in wavelength instead of time; PD is a photo detector 42; BS is a beam splitting fiber coupler 32; DSP is a digital signal processor 44; REF is a mirror 36 that provides a reference signal by reflecting light back into the fiber optic cable; and SMP is the sample region 40. The SS laser 30 launches light into a fiber optic cable. The BS 32 sends some light to the REF mirror 36 and some light to the SMP sample 40. Some light reflects off the REF mirror 36, through the BS 32, and then onto the PD photodetector 42. Some light scatters off the different layers in the SMP sample 40, goes back into the fiber, back through the BS 32, and onto the photodetector 42. Over a period of about a millisecond, the SS laser 30 sweeps through a range of wavelengths. As it does, the signal on the photodetector varies rapidly with time. The cause is that light from the REF mirror and the SMP sample is either constructively or destructively interfering. The DSP digital signal processor analyzes the time series data using Fourier transforms techniques and converts the signal into a depth map of where there are scattering structures. This is a depth map over a single line through the sample. If the sample is moved across the beam, a cross sectional image can be created by the DSP 44 in conjunction with a recording device. The results can be displayed on a display screen 46.

A basic method used by a Purkinjenator™ optical system 8 is to control the illumination dynamically during the light acquisition process, which separates the various reflected images, even in the presence of complicating reflections.

Several technological features can be used (either alone or in combination) in another embodiment of a Purkinjenator™ optical system when multi-focal IOLs (MF-IOL) are measured, including, but not limited to:

A. OCT imaging: The cross-sectional OCT images could be combined with en-face OCT images to determine the position of the MF-IOL rings.

B. Darkfield imaging: Darkfield imaging can be used to detect those regions where there are abrupt changes in the light scattering. With the addition of a second beamsplitter 85, a darkfield mask 87, a third lens, 83, and a second camera 91, a darkfield image arrangement can readily be constructed (see FIG. 43). This configuration allows the Multi-Focal rings to be detected (but would not give direct information about the relative height of each ring).

C. Surface scanning: With the addition of a scanner (see FIGS. 42 and 44), a small beam of light could be projected onto the surface of the MF-IOL. This would provide for some profile information to be obtained.

D. Wavefront sensing: By projecting a small spot of light onto the retina, the MF-IOL can be illuminated from behind with light reflected off of the retina. This can be used in conjunction with a wavefront sensor to measure the phase directly. A wavefront system (WFS) with sufficient resolution would be needed. However, this option may be feasible using modern high-resolution cameras and Lenslet arrays, or other optical means.

Multi-focal IOLs are designed to correct presbyopia by creating multiple focal positions. This uses a diffractive optic (e.g., Fresnel Rings) to act as a beamsplitter to split some of the light and create focuses both for distant targets and for near targets. These diffractive optics operate at the central visible wavelength, typically 550 nm wavelength. However, nearly all wavefront aberrometers and other instruments use near-IR wavelengths in order to minimize visible light to the patient. This makes measurement of the two different focal positions inaccurate. To properly measure MF-IOLs in the eye, it may be advantageous to make the wavefront measurements at multiple wavelengths. These measurements can be compared to determine the proportion of light that is directed to each focal point.

Figure 30:
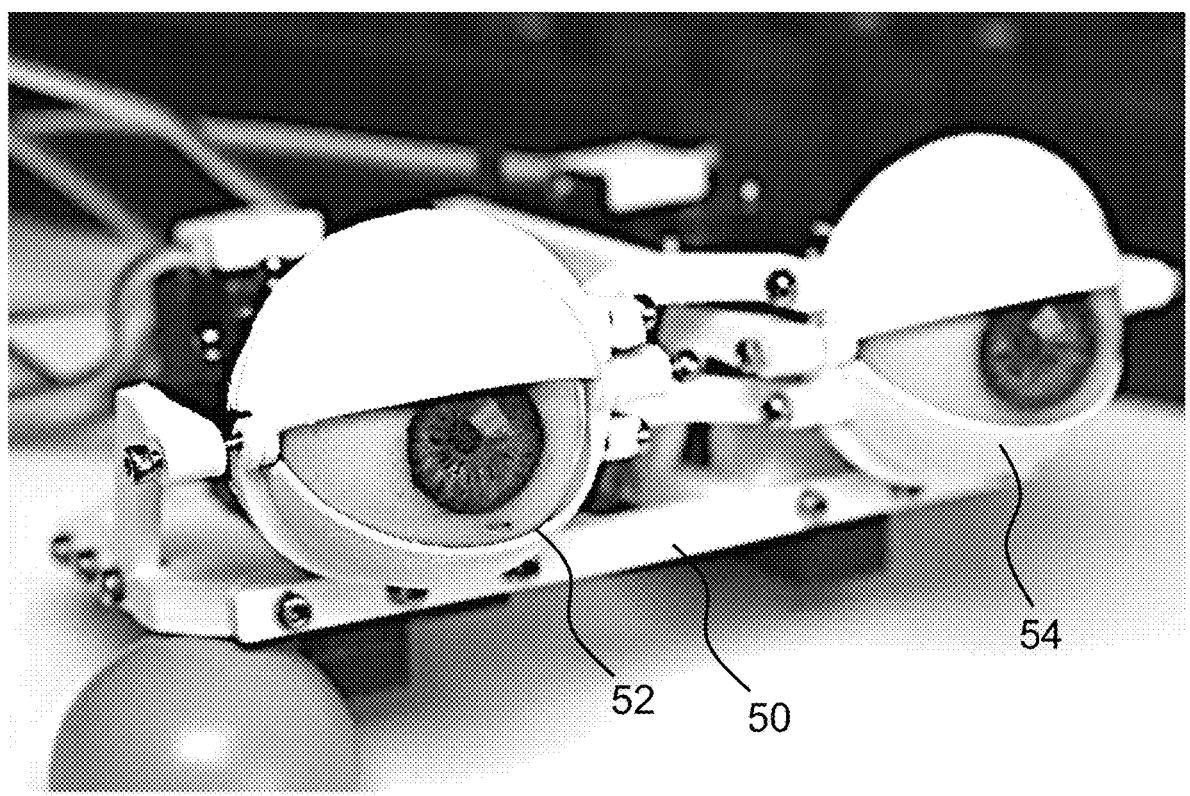
FIG. 30 shows a photograph of an animatronic pair of mechanical model eyes, according to the present invention.

A static eye model with different IOLs (not shown) can be used in breadboard testing. Alternatively, as shown in FIG. 30, to facilitate rapid testing of the various real-time measurement techniques, an animatronic mechanical eye 50 with two linked eyeballs 52 and 54 can be used. This model eye allows testing with realistic eye motion profiles to determine the level of tracking required; and for testing algorithms in close to real-world conditions.

FIG. 31 show a process flow chart for doing laser eye sculpting using a system comprising an OCT optical system combined with a Purkinjenator™ optical device, according to the present invention. In step 100, Optical Coherence Tomography (OCT) is used to find an initial XYZ position of an IOL prior to initial sculpting. In step 102, a laser sculpting pulse is applied to the eye (e.g., by a femtosecond laser). In step 104, a Purkinje eye-tracking system is used to monitor any changes in the IOL's position (at high tracking speed). In step 106, the laser sculpting parameters are adjusted to compensate for a changed position of the IOL, based on output of measurements from step 104. In step 108, the method returns back to step 102 and an additional laser sculpting pulse is applied to the eye, followed by repeating steps 102, 104 and 106 as often as needed until the process is completed in step 110.

REFERENCES

[1] H. D. Crane & C. M. Steele, "Generation-V Dual-Purkinje-Image Eyetracker", APPLIED OPTICS, Vol. 24, No. 4, pp. 527-537, February 1985.

[2] H. Duebel, B. Bridgeman, "Fourth Purkinje Image Signals Reveal Eye-Lens Deviations and Retinal image Distortions During Saccades", VISION RES., Vol. 35, No. 4, pp. 529-538, 1995.

[3] M. Almeida, "Detection of Purkinje Images for Automatic Positioning of Fixation Target and Interferometric Measurements of Anterior Eye Chamber", Master Dissertation, University Nova de Lisboa, Spain, April, 2012.

[4] P. Santos, et al., "System based on the contrast of Purkinje images to measure corneal and lens scattering", BIOMEDICAL OPTICS EXPRESS, VOL. 9, No. 10, October 2018, pp. 4907-4918.

[5] "Cassini Ambient"—product brochure, multi-color (700 LED's) Total Corneal Astigmatism LED topography based on $2^{nd}$ Purkinje raytracing technology, October, 2020.

[6] M. R. Clark, "A two-dimensional Purkinje eye tracker using the first and fourth Purkinje images", Behavior Research Methods & Instrumentation, Vol. 7 (2), pp. 215-219, 1975.

[7] D. H. Chang, "Centering IOLs Using Purkinje Images", CATARACT & REFRACTIVE SURGERY TODAY, pp. 35-38, June, 2011.

[8] unknown author, "Technical Challenges in Eye Tracking", pp. 1-43, ESSEM, 2014.

[9] E. Abdulin, et al., "Custom Video-Oculography Device and its Application to Fourth Purkinje Image Detection during Saccades", 2018.

[10] J. Tabernero, P. Artal, "Lens Oscillations in the Human Eye: Implications for Post-Saccadic Suppression of Vision", PLOS ONE, Vol. 9, Issue 4, e95764, April, 2014.

[11] S. Manzanera, et al., "Location of Achromatizing Pupil Position and First Purkinje Reflection in a Normal Population", Investigative Ophthalmology & Visual Science, Vol. 56, pp. 962-966, February, 2015.

[12] T. N. Cornsweet & H. D. Crane, "Accurate two-dimensional eye tracker using first and fourth Purkinje images", Journal of the Optical Society of America, Vol. 63, No. 8, pp. 921-928, August 1973.

[13] P. Santos, et al., "System based on the contrast of Purkinje images to measure corneal and lens scattering", Biomed Opt. Express, Vol. 9(10), pp. 4907-4918, October, 2018.

[14] J. Tabernero, et al., "Instrument for measuring the misalignment of ocular surfaces", OPTICS EXPRESS, Vol. 14(22), pp. 10945-10956, October, 2006.

[15] M. Bueno, et al., "Purkinje imaging system to measure anterior segment scattering in the human eye", OPTICS LETTERS, Vol. 32(23), pp. 3447-3449, December, 2007.

[16] D. W. Hansen, and Q. Ji, "In the Eye of the Beholder: A Survey of Models for Eyes and Gaze", IEEE Transactions on Pattern Analysis and Machine Intelligence, Vol, 32(3), pp. 478-500, March, 2010.

[17] M. Sun, et al., "Intraocular lens alignment from an en face optical coherence tomography image Purkinje-like method", Optical Engineering, Vol. 53(6), pp. 061704-061708, June, 2014.

[18] A. Chamberlain, "Dural Purkinje-Image Eyetracker", United States Naval Academy Trident Scholar Report 238, 65 pages, (1996).

[19] H. L. Hall, "Purkinje images for optical assessment of lenticular surfaces", Univ. of Arizona, Ph.D. Dissertation, 2001.

[20] J. Tabernero, et al., "The accommodative ciliary muscle function is preserved in older humans", www.nature.com/scientificreports/, 6:25551|DOI: 10.1038/srep25551, pp. 1-7, May, 2016.

[21] Book, Chapter 5: "Eye Tracking Techniques".

[22] M. Cognolato, et al., "Head-mounted eye gaze tracking devices: An overview of modern devices and advances", Wearable Technologies for Active Living and Rehabilitation, Creative Commons, https://doi.org/10.1177/2055668318773991, April, 2018.

[23] M. Sun, et al., "Intraocular lens alignment from an en face optical coherence tomography image Purkinje-like method", Optical Engineering, Vol. 53(6), pp. 061704-061708, June, 2014.

[24] E. R. Abdulin & O. V. Komogortsev, "Study of Additional Eye-Related Features for Future Eye-Tracking Techniques", CHI 2017, May 6-11, 2017, pp. 1457-1463, Denver, CO.

[25] A. Nolan, et al., "Model eye measurement with novel device combining Purkinje reflections and OLCR", Investigative Ophthalmology & Visual Science, Vol. 56(7), June, 2015.

[26] U.S. Pat. No. 3,536,383_Cornsweet_1967
[27] U.S. Pat. No. 4,287,410_Crane_1981
[28] U.S. Pat. No. 4,373,787_Crane_1983
[29] U.S. Pat. No. 4,834,528_Howland
[30] U.S. Pat. No. 4,836,670_Hutchinson
[31] U.S. Pat. No. 5,430,505_Katz
[32] U.S. Pat. No. 7,572,008_Elvesjo
[33] U.S. Pat. No. 7,963,652_Vertegaal
[34] U.S. Pat. No. 8,360,578_Nummela
[35] U.S. Pat. No. 8,678,591_Zhou
[36] U.S. Pat. No. 9,167,965_Jaeken
[37] U.S. Pat. No. 9,301,675_Kiderman
[38] U.S. Pat. No. 9,649,029_Blixt
[39] U.S. Pat. No. 9,918,873_Woodley
[40] U.S. Pat. No. 9,949,636_Kersting
[41] U.S. Pat. No. 9,999,348_Gao
[42] U.S. Pat. No. 10,080,493_Reimer
[43] U.S. Pat. No. 10,251,784_Woodley
[44] U.S. Pat. No. 10,278,576_Hwang
[45] U.S. Pat. No. 10,420,466_Cornsweet
[46] U.S. Pat. No. 10,463,248_Cornsweet
[47] U.S. Pat. No. 10,579,141_Aleem
[48] U.S. Pat. No. 10,606,072_Aleem
[49] 20180129041_Aleem
[50] U.S. Pat. No. 10,694,938_Janunts
[51] U.S. Pat. No. 10,718,942_Egea
[52] 2018/0003981_Urey
[53] 2018/0129279_Melman
[54] 2018/0207031_Woodley
[55] 2018/0249906_Gramatikov
[56] 2018/0344157_Ng
[57] 2019/0231590_Woodley
[58] 2020/0154996_Blixt
[59] 2004/0021826_Sarver
[60] 2011/0273669_Abitbol
[61] WO2004084719_Youssefi
[62] WO2012130818A1_Ng
[63] Andrew T. Duchowski, "Eye Tracking Methodology: Theory and Practice", Springer, 2003.
[64] 2018_VDC-Whitepaper_Eye_Tracking_Technologies_v01. https://www.slideshare.net/christophrunde/eye-tracking-technologies-vdcwhitepaper
[65] Xin et al. "Optical coherence tomography-based deep learning algorithm for quantification of the location of the intraocular lens", Ann Transl Med. 2020 Jul. 8(14):872.

What is claimed is:

1. A method of determining an XYZ position and tip/tilt orientation of an optical structure in a patient's eye by using an optical instrument, wherein the method comprises:

(a) providing an optical instrument with a main optical axis, a camera aligned with the main optical axis, and a plurality of front light sources disposed around the main optical axis;
(b) illuminating the patient's eye with a first front light source; then
(c) capturing, with the camera, a first image of the patient's eye, wherein the first image comprises one or more first front Purkinje reflection spots from the optical structure; then
(d) turning off the first front light source; then
(e) illuminating the patient's eye with a second front light source, wherein the second front light source is offset from the first front light source; then
(f) capturing, with the camera, a second image of the patient's eye, wherein the second image comprises one or more second front Purkinje reflection spots from the optical structure; then
(g) comparing the first image to the second image, and associating the one or more first and second front Purkinje reflection spots with one or more surfaces of the optical structure;
(h) measuring, using the first and second images, one or more positions of the one or more first and second front Purkinje reflection spots;
(i) calculating an XYZ position and/or tip/tilt angles of the optical structure by using the one or more positions of the one or more first and second front Purkinje reflection spots;
(j) illuminating the patient's eye with a first rear light source that is located at a rear Z-axis position along the main optical axis, wherein the first rear light source is located farther away from the patient's eye than the first front light source;
(k) generating one or more first rear Purkinje reflection spots on the patient's eye; then (l) turning off the first rear light source; then
(m) illuminating the patient's eye with a second rear light source that is located at the rear Z-axis position;
(n) generating one or more second rear Purkinje reflection spots on the patient's eye;
(o) measuring one or more first positions of the one or more first rear Purkinje reflection spots;
(p) measuring one or more second positions of the one or more second rear Purkinje reflection spots;
(q) comparing the one or more first positions to the one or more second positions;
(r) calculating a front position of a front surface of the optical structure; and
(s) calculating a rear position along a Z-axis of a rear surface of the optical structure;
wherein the first rear light source is offset from the second rear light source;
wherein the Z-axis coincides with the main optical axis of the optical instrument;
wherein light emitted by the first and second front light sources takes a single pass though the optical instrument;
wherein single-pass Purkinje images generated by the first and second front light sources are responsive to both movement and curvature of the optical structure;
wherein light emitted by the first and second rear light sources takes a double-pass though the optical instrument;
wherein double-pass Purkinje images generated by the first and second rear light sources are responsive only to the curvature of the optical structure and are not responsive to changes in an axial path distance along the main optical axis; and
wherein the method further comprises:
(t) determining a Z-axis distance from a patient's cornea to a front objective lens of the optical instrument; and
(u) determining a curvature of the optical structure by comparing the single-pass Purkinje images to the double-pass Purkinje images.

2. The method of claim 1, further comprising
using a motion-capture analysis algorithm to uniquely associate the first or second light source with one or more types of Purkinje reflection spots chosen from a set of four different Purkinje reflection spots: $P_1$, $P_2$, $P_3$, and $P_4$.

3. The method of claim 1, where the optical structure comprises a natural lens.

4. The method of claim 1, where the optical structure comprises an Intraocular Lens (IOL) or an Implanted Contact Lens (ICL).

5. The method of claim 1, where the optical structure comprises a cornea.

6. The method of claim 5, further comprising identifying one or more Purkinje reflection spots from the cornea of the patient's eye.

7. The method of claim 1, wherein the first and second front light sources comprise infrared LED light sources.

8. The method of claim 1, further comprising:
controlling activation of the first and second front light sources with a micro-controller using firmware, and
synchronizing activating the first and second front light sources with activating a camera.

9. The method of claim 1, further comprising identifying and separating overlapping Purkinje reflections from each other.

10. The method of claim 1, further comprising:
calculating an exterior surface shape of a patient's cornea;
calculating a first distance from an anterior surface of the patient's cornea to a front objective lens of the optical instrument;
calculating a front curvature and a back curvature of a patient's lens;
calculating a thickness of the patient's lens; and
calculating a second distance from the patient's lens to a posterior surface of the patient's cornea.

11. The method of claim 1, further comprising:
generating one or more illuminated video patterns with a video display unit or a micro-video display unit, and
using the video display unit or the micro-video display unit as a target to guide a fixation of a patient's gaze.

12. The method of claim 1,
further comprising synchronizing activating the first light source or the second light source with activating the camera so that only one of the first light source or the second light source is imaged one at a time.

13. The method of claim 12, further comprising:
adaptatively programming a first temporal activation sequence of the first front light source;
adaptatively programming a second temporal activation sequence of the second front light source;
identifying one or more overlapping Purkinje spots in one or more captured camera frames; and then
eliminating one or more corresponding front light sources that cause the one or more overlapping Purkinje spots to appear in the one or more captured camera frames.

14. The method of claim 12, further comprising:
recognizing locations of the one or more Purkinje reflection spots that have been captured by the camera; and
using a motion-capture analysis algorithm to uniquely associate a first or second front light source with one or more types of Purkinje reflection spots chosen from a set of four Purkinje reflection spots: $P_1$, $P_2$, $P_3$, and $P_4$.

15. The method of claim 1, wherein the first and second front light sources are physically arranged in a Cartesian grid to facilitate pattern recognition.

16. The method of claim 1, wherein the first and second front light sources are arranged in one or more rings disposed around a front objective lens in the optical instrument.

17. The method of claim 1, further comprising activating the first and second front light sources and activating the first and second rear light sources sequentially at different times.

18. The method of claim 1, further comprising using an aperture located at a telecentric stop in the optical instrument to reduce an intensity of the first and second front light sources that are transmitted to the camera.

19. The method of claim 1, further comprising:
using a first color for the first front light source; and
using a second color for the second front light source;
wherein the first color is different than the second color.

20. The method of claim 10, wherein calculating comprises solving a set of simultaneous equations algebraically using a thin-lens equation.

21. The method of claim 1, further comprising:
reducing an intensity of the first front light source so that an apparent brightness of $P_3$ and $P_4$ Purkinje spots lies in a middle of a sensitivity range of the camera; and
leaving corneal reflection spots $P_1$ and $P_2$ saturated on the camera; and
thereby differentiating $P_3$ and $P_4$ Purkinje spot reflections from $P_1$ and $P_2$ Purkinje spot reflections based on differences in brightness between different Purkinje spots.

22. The method of claim 1, further comprising:
defining a first pair of front light sources consisting of the first front light source and the second front light source; and
defining a second pair of front light sources consisting of a third front light source and a fourth front light source;
wherein the first pair of front light sources are physically separated from the second pair of front light sources by a defined distance; and
wherein the method further comprises sequentially illuminating the patient's eye with the first pair of light sources at a different time from illuminating the patient's eye with the second pair of light sources.

23. The method of claim 1, further comprising sequentially illuminating the patient's eye with from 10 to 100 pairs of individually-activatable, physically-separated front light sources.

24. The method of claim 1, further comprising:
turning ON one or more front light sources that are widely-separated apart in physical space; and then
using image analysis software to uniquely and accurately associate individual front light sources with at least two individual Purkinje spots located on different sides of the patient's eye.

* * * * *